(12) United States Patent
Velasco et al.

(10) Patent No.: US 11,030,922 B2
(45) Date of Patent: Jun. 8, 2021

(54) LAPAROSCOPIC TRAINING SYSTEM

(71) Applicant: Applied Medical Resources Corporation, Rancho Santa Margarita, CA (US)

(72) Inventors: Joel B. Velasco, Rancho Santa Margarita, CA (US); Jacob J. Filek, Rancho Santa Margarita, CA (US); Nico Slabber, Corona, CA (US); Samantha Chan, Rancho Santa Margarita, CA (US); Branden Carter, Rancho Santa Margarita, CA (US); Zachary Michaels, Rancho Santa Margarita, CA (US); Nathan Landino, Rancho Santa Margarita, CA (US); Brandon Pereles, Rancho Santa Margarita, CA (US); Eduardo Bolanos, Rancho Santa Margarita, CA (US); Cory S. Hague, Rancho Santa Margarita, CA (US); Gregory K. Hofstetter, Rancho Santa Margarita, CA (US); Sean Kenneday, Rancho Santa Margarita, CA (US); Timothy McMorrow, Trabuco Canyon, CA (US); Jigar Shah, Rancho Santa Margarita, CA (US); Jimmy Ho, Rancho Santa Margarita, CA (US); Lindsey Chase, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 457 days.

(21) Appl. No.: 15/895,707

(22) Filed: Feb. 13, 2018

(65) Prior Publication Data
US 2018/0233067 A1 Aug. 16, 2018

Related U.S. Application Data

(60) Provisional application No. 62/458,972, filed on Feb. 14, 2017.

(51) Int. Cl.
*G09B 23/28* (2006.01)
*A61B 34/00* (2016.01)
*G09B 23/30* (2006.01)

(52) U.S. Cl.
CPC ...... *G09B 23/285* (2013.01); *A61B 2034/258* (2016.02); *G09B 23/30* (2013.01)

(58) Field of Classification Search
CPC ...... G09B 23/285; G09B 23/30; G09B 23/28; A61B 2034/258
(Continued)

(56) References Cited

U.S. PATENT DOCUMENTS 184,573 A 11/1876 Becker
2,127,774 A 8/1938 Jacobs
(Continued)

FOREIGN PATENT DOCUMENTS

CN 2421706 Y 2/2001
CN 2751372 Y 1/2006
(Continued)

OTHER PUBLICATIONS

The International Bureau of WIPO, International Preliminary Report on Patentability for International Application No. PCT/US2016/055148, entitled "Hysterectomy Model," dated Apr. 12, 2018, 12 pgs.
(Continued)

*Primary Examiner* — James B Hull
*Assistant Examiner* — Lily M Del Valle
(74) *Attorney, Agent, or Firm* — Thomas D. Nguyen; Patrick Ikehara

(57) ABSTRACT

A sensorized surgical instrument for training users laparoscopic surgical procedures is provided. The instrument
(Continued)

includes at least one sensor selected from a group consisting of a strain gauge, accelerometer, magnetometer, and gyroscope. The sensor is attached directly to a handle of the instrument. A shaft assembly having a tool tip is interchangeably connectable to the handle. The sensor is connected to a computer configured to provide feedback useful to the user for improving the user's surgical skills. The feedback includes the time to complete a procedure, economy of motion, smoothness of motion and the force exerted at the tool tip.

27 Claims, 52 Drawing Sheets

(58) Field of Classification Search
USPC ............................................. 434/262
See application file for complete search history.

(56) References Cited

U.S. PATENT DOCUMENTS

| | | |
|---|---|---|
| 2,284,888 A | 6/1942 | Arneil, Jr. |
| 2,324,702 A | 7/1943 | Hoffman et al. |
| 2,345,489 A | 3/1944 | Lord |
| 2,495,568 A | 1/1950 | Coel |
| 3,766,666 A | 10/1973 | Stroop |
| 3,775,865 A | 12/1973 | Rowan |
| 3,789,518 A | 2/1974 | Chase |
| 3,921,311 A | 11/1975 | Beasley et al. |
| 3,991,490 A | 11/1976 | Markman |
| 4,001,951 A | 1/1977 | Fasse |
| 4,001,952 A | 1/1977 | Kleppinger |
| 4,321,047 A | 3/1982 | Landis |
| 4,323,350 A | 4/1982 | Bowden, Jr. |
| 4,332,569 A | 6/1982 | Burbank |
| 4,371,345 A | 2/1983 | Palmer et al. |
| 4,386,917 A | 6/1983 | Forrest |
| 4,459,113 A | 7/1984 | Boscaro Gatti et al. |
| 4,481,001 A | 11/1984 | Graham et al. |
| 4,596,528 A | 6/1986 | Lewis et al. |
| 4,726,772 A | 2/1988 | Amplatz |
| 4,737,109 A | 4/1988 | Abramson |
| 4,789,340 A | 12/1988 | Zikria |
| 4,832,978 A | 5/1989 | Lesser |
| 4,867,686 A | 9/1989 | Goldstein |
| 4,907,973 A | 3/1990 | Hon |
| 4,938,696 A | 7/1990 | Foster et al. |
| 4,940,412 A | 7/1990 | Blumenthal |
| 5,061,187 A | 10/1991 | Jerath |
| 5,083,962 A | 1/1992 | Pracas |
| 5,104,328 A | 4/1992 | Lounsbury |
| 5,149,270 A | 9/1992 | McKeown |
| 5,180,308 A | 1/1993 | Garito et al. |
| 5,230,630 A | 7/1993 | Burgett |
| 5,273,435 A | 12/1993 | Jacobson |
| 5,295,694 A | 3/1994 | Levin |
| 5,310,348 A | 5/1994 | Miller |
| 5,318,448 A | 6/1994 | Garito et al. |
| 5,320,537 A | 6/1994 | Watson |
| 5,358,408 A | 10/1994 | Medina |
| 5,368,487 A | 11/1994 | Medina |
| 5,380,207 A | 1/1995 | Siepser |
| 5,403,191 A | 4/1995 | Tuason |
| 5,425,644 A | 6/1995 | Szinicz |
| 5,425,731 A | 6/1995 | Daniel et al. |
| 5,472,345 A | 12/1995 | Eggert |
| 5,518,406 A | 5/1996 | Waters |
| 5,518,407 A | 5/1996 | Greenfield et al. |
| 5,520,633 A | 5/1996 | Costin |
| 5,541,304 A | 7/1996 | Thompson |
| 5,620,326 A | 4/1997 | Younker |
| 5,720,742 A | 2/1998 | Zacharias |
| 5,722,836 A | 3/1998 | Younker |
| 5,727,948 A | 3/1998 | Jordan |
| 5,743,730 A | 4/1998 | Clester et al. |
| 5,762,458 A | 6/1998 | Wang et al. |
| 5,769,640 A | 6/1998 | Jacobus et al. |
| 5,775,916 A | 7/1998 | Cooper et al. |
| 5,785,531 A | 7/1998 | Leung |
| 5,800,178 A | 9/1998 | Gillio |
| 5,803,746 A | 9/1998 | Barrie et al. |
| 5,807,378 A | 9/1998 | Jensen et al. |
| 5,810,880 A | 9/1998 | Jensen et al. |
| 5,814,038 A | 9/1998 | Jensen et al. |
| 5,850,033 A | 12/1998 | Mirzeabasov et al. |
| 5,855,583 A | 1/1999 | Wang et al. |
| 5,873,732 A | 2/1999 | Hasson |
| 5,873,863 A | 2/1999 | Komlosi |
| 5,908,302 A | 6/1999 | Goldfarb |
| 5,947,743 A | 9/1999 | Hasson |
| 5,951,301 A | 9/1999 | Younker |
| 6,080,181 A | 6/2000 | Jensen et al. |
| 6,083,008 A | 7/2000 | Yamada et al. |
| 6,113,395 A | 9/2000 | Hon |
| 6,234,804 B1 | 5/2001 | Yong |
| 6,271,278 B1 | 8/2001 | Park et al. |
| 6,336,812 B1 | 1/2002 | Cooper et al. |
| 6,398,557 B1 | 6/2002 | Hoballah |
| 6,413,264 B1 | 7/2002 | Jensen et al. |
| 6,474,993 B1 | 11/2002 | Grund et al. |
| 6,485,308 B1 | 11/2002 | Goldstein |
| 6,488,507 B1 | 12/2002 | Stoloff et al. |
| 6,497,902 B1 | 12/2002 | Ma |
| 6,511,325 B1 | 1/2003 | Lalka et al. |
| 6,517,354 B1 | 2/2003 | Levy |
| 6,568,941 B1 | 5/2003 | Goldstein |
| 6,589,057 B1 | 7/2003 | Keenan et al. |
| 6,620,174 B2 | 9/2003 | Jensen et al. |
| 6,654,000 B2 | 11/2003 | Rosenberg |
| 6,659,776 B1 | 12/2003 | Aumann et al. |
| 6,773,263 B2 | 8/2004 | Nicholls et al. |
| 6,780,016 B1 | 8/2004 | Toly |
| 6,817,973 B2 | 11/2004 | Merril et al. |
| 6,820,025 B2 | 11/2004 | Bachmann et al. |
| 6,854,976 B1 | 2/2005 | Suhr |
| 6,857,878 B1 | 2/2005 | Chosack et al. |
| 6,863,536 B1 | 3/2005 | Fisher et al. |
| 6,866,514 B2 | 3/2005 | Von Roeschlaub et al. |
| 6,887,082 B2 | 5/2005 | Shun |
| 6,929,481 B1 | 8/2005 | Alexander et al. |
| 6,939,138 B2 | 9/2005 | Chosack et al. |
| 6,950,025 B1 | 9/2005 | Nguyen |
| 6,960,617 B2 | 11/2005 | Omidian et al. |
| 6,997,719 B2 | 2/2006 | Wellman et al. |
| 7,008,232 B2 | 3/2006 | Brassel |
| 7,018,327 B1 | 3/2006 | Conti |
| 7,025,064 B2 | 4/2006 | Wang et al. |
| 7,056,123 B2 | 6/2006 | Gregorio et al. |
| 7,080,984 B1 | 7/2006 | Cohen |
| 7,118,582 B1 | 10/2006 | Wang et al. |
| 7,255,565 B2 | 8/2007 | Keegan |
| 7,269,532 B2 | 9/2007 | David et al. |
| 7,272,766 B2 | 9/2007 | Sakezles |
| 7,300,450 B2 | 11/2007 | Vleugels et al. |
| 7,364,582 B2 | 4/2008 | Lee |
| 7,404,716 B2 | 7/2008 | Gregorio et al. |
| 7,419,376 B2 | 9/2008 | Sarvazyan et al. |
| 7,427,199 B2 | 9/2008 | Sakezles |
| 7,431,189 B2 | 10/2008 | Shelton, IV et al. |
| 7,441,684 B2 | 10/2008 | Shelton, IV et al. |
| 7,465,168 B2 | 12/2008 | Allen et al. |
| 7,467,075 B2 | 12/2008 | Humphries et al. |
| 7,544,062 B1 | 6/2009 | Hauschild et al. |
| 7,549,866 B2 | 6/2009 | Cohen et al. |
| 7,553,159 B1 | 6/2009 | Arnal et al. |
| 7,575,434 B2 | 8/2009 | Palakodeti |
| 7,594,815 B2 | 9/2009 | Toly |
| 7,621,749 B2 | 11/2009 | Munday |
| 7,646,901 B2 | 1/2010 | Murphy et al. |
| 7,648,367 B1 | 1/2010 | Makower et al. |
| 7,648,513 B2 | 1/2010 | Green et al. |
| 7,651,332 B2 | 1/2010 | Dupuis et al. |
| 7,677,897 B2 | 3/2010 | Sakezles |

(56) References Cited

U.S. PATENT DOCUMENTS

| | | |
|---|---|---|
| 7,775,916 B1 | 8/2010 | Mahoney |
| 7,780,451 B2 | 8/2010 | Willobee et al. |
| 7,802,990 B2 | 9/2010 | Korndorffer et al. |
| 7,803,151 B2 | 9/2010 | Whitman |
| 7,806,696 B2 | 10/2010 | Alexander et al. |
| 7,819,799 B2 | 10/2010 | Merril et al. |
| 7,833,018 B2 | 11/2010 | Alexander et al. |
| 7,837,473 B2 | 11/2010 | Koh |
| 7,850,454 B2 | 12/2010 | Toly |
| 7,850,456 B2 | 12/2010 | Chosack et al. |
| 7,854,612 B2 | 12/2010 | Frassica et al. |
| 7,857,626 B2 | 12/2010 | Toly |
| 7,866,983 B2 | 1/2011 | Hemphill et al. |
| 7,931,470 B2 | 4/2011 | Alexander et al. |
| 7,931,471 B2 | 4/2011 | Senagore et al. |
| 7,988,992 B2 | 8/2011 | Omidian et al. |
| 7,993,140 B2 | 8/2011 | Sakezles |
| 7,997,903 B2 | 8/2011 | Hasson et al. |
| 8,007,281 B2 | 8/2011 | Toly |
| 8,007,282 B2 | 8/2011 | Gregorio et al. |
| 8,016,818 B2 | 9/2011 | Ellis et al. |
| 8,017,107 B2 | 9/2011 | Thomas et al. |
| 8,021,162 B2 | 9/2011 | Sui |
| 8,048,088 B2 | 11/2011 | Green et al. |
| 8,083,691 B2 | 12/2011 | Goldenberg et al. |
| 8,116,847 B2 | 2/2012 | Gattani et al. |
| 8,137,110 B2 | 3/2012 | Sakezles |
| 8,157,145 B2 | 4/2012 | Shelton, IV et al. |
| 8,197,464 B2 | 6/2012 | Krever et al. |
| 8,205,779 B2 | 6/2012 | Ma et al. |
| 8,221,129 B2 | 7/2012 | Parry et al. |
| 8,297,982 B2 | 10/2012 | Park et al. |
| 8,308,817 B2 | 11/2012 | Egilsson et al. |
| 8,323,028 B2 | 12/2012 | Matanhelia |
| 8,323,029 B2 | 12/2012 | Toly |
| 8,328,560 B2 | 12/2012 | Niblock et al. |
| 8,342,851 B1 | 1/2013 | Speeg et al. |
| 8,403,674 B2 | 3/2013 | Feygin et al. |
| 8,403,675 B2 | 3/2013 | Stoianovici et al. |
| 8,403,676 B2 | 3/2013 | Frassica et al. |
| 8,408,920 B2 | 4/2013 | Speller |
| 8,425,234 B2 | 4/2013 | Sakezles |
| 8,439,687 B1 | 5/2013 | Morriss et al. |
| 8,442,621 B2 | 5/2013 | Gorek et al. |
| 8,454,368 B2 | 6/2013 | Ault et al. |
| 8,459,094 B2 | 6/2013 | Yanni |
| 8,459,520 B2 | 6/2013 | Giordano et al. |
| 8,460,002 B2 | 6/2013 | Wang et al. |
| 8,465,771 B2 | 6/2013 | Wan et al. |
| 8,469,715 B2 | 6/2013 | Ambrozio |
| 8,469,716 B2 | 6/2013 | Fedotov et al. |
| 8,480,407 B2 | 7/2013 | Campbell et al. |
| 8,480,408 B2 | 7/2013 | Ishii et al. |
| 8,491,309 B2 | 7/2013 | Parry et al. |
| 8,500,753 B2 | 8/2013 | Green et al. |
| 8,512,044 B2 | 8/2013 | Sakezles |
| 8,517,243 B2 | 8/2013 | Giordano et al. |
| 8,521,252 B2 | 8/2013 | Diez |
| 8,535,062 B2 | 9/2013 | Nguyen |
| 8,544,711 B2 | 10/2013 | Ma et al. |
| 8,556,635 B2 | 10/2013 | Toly |
| 8,608,483 B2 | 12/2013 | Trotta et al. |
| 8,613,621 B2 | 12/2013 | Henderickson et al. |
| 8,636,520 B2 | 1/2014 | Iwasaki et al. |
| D699,297 S | 2/2014 | Bahsoun et al. |
| 8,641,423 B2 | 2/2014 | Gumkowski |
| 8,647,125 B2 | 2/2014 | Johns et al. |
| 8,678,831 B2 | 3/2014 | Trotta et al. |
| 8,679,279 B2 | 3/2014 | Thompson et al. |
| 8,696,363 B2 | 4/2014 | Gray et al. |
| 8,708,213 B2 | 4/2014 | Shelton, IV et al. |
| 8,708,707 B2 | 4/2014 | Hendrickson et al. |
| 8,764,449 B2 | 7/2014 | Rios et al. |
| 8,764,452 B2 | 7/2014 | Pravong et al. |
| 8,800,839 B2 | 8/2014 | Beetel |
| 8,801,437 B2 | 8/2014 | Mousques |
| 8,801,438 B2 | 8/2014 | Sakezles |
| 8,807,414 B2 | 8/2014 | Ross et al. |
| 8,808,004 B2 | 8/2014 | Misawa et al. |
| 8,808,311 B2 | 8/2014 | Heinrich et al. |
| 8,814,573 B2 | 8/2014 | Nguyen |
| 8,827,988 B2 | 9/2014 | Belson et al. |
| 8,840,628 B2 | 9/2014 | Green et al. |
| 8,870,576 B2 | 10/2014 | Millon et al. |
| 8,888,498 B2 | 11/2014 | Bisaillon et al. |
| 8,893,946 B2 | 11/2014 | Boudreaux et al. |
| 8,911,238 B2 | 12/2014 | Forsythe |
| 8,915,742 B2 | 12/2014 | Hendrickson et al. |
| 8,945,095 B2 | 2/2015 | Blumenkranz et al. |
| 8,961,190 B2 | 2/2015 | Hart et al. |
| 8,966,954 B2 | 3/2015 | Ni et al. |
| 8,968,003 B2 | 3/2015 | Hendrickson et al. |
| 9,008,989 B2 | 4/2015 | Wilson et al. |
| 9,017,080 B1 | 4/2015 | Placik |
| 9,026,247 B2 | 5/2015 | White |
| 9,050,201 B2 | 6/2015 | Egilsson et al. |
| 9,056,126 B2 | 6/2015 | Hersel et al. |
| 9,070,306 B2 | 6/2015 | Rappel et al. |
| 9,087,458 B2 | 7/2015 | Shim et al. |
| 9,096,744 B2 | 8/2015 | Wan et al. |
| 9,117,377 B2 | 8/2015 | Shim et al. |
| 9,119,572 B2 | 9/2015 | Gorek et al. |
| 9,123,261 B2 | 9/2015 | Lowe |
| 9,129,054 B2 | 9/2015 | Nawana et al. |
| 9,196,176 B2 | 11/2015 | Hager et al. |
| 9,226,799 B2 | 1/2016 | Lightcap et al. |
| 9,257,055 B2 | 2/2016 | Endo et al. |
| 9,265,587 B2 | 2/2016 | Vancamberg et al. |
| 9,295,468 B2 | 3/2016 | Heinrich et al. |
| 9,336,694 B2 | 5/2016 | Shim et al. |
| 9,351,714 B2 | 5/2016 | Ross et al. |
| 9,358,682 B2 | 6/2016 | Ruiz Morales |
| 9,364,224 B2 | 6/2016 | Nicholas et al. |
| 9,364,279 B2 | 6/2016 | Houser et al. |
| 9,370,361 B2 | 6/2016 | Viola et al. |
| 9,373,270 B2 | 6/2016 | Miyazaki |
| 9,387,276 B2 | 7/2016 | Sun et al. |
| 9,427,496 B2 | 8/2016 | Sun et al. |
| 9,439,649 B2 | 9/2016 | Shelton, IV et al. |
| 9,439,733 B2 | 9/2016 | Ha et al. |
| 9,449,532 B2 | 9/2016 | Black et al. |
| 9,468,438 B2 | 10/2016 | Baber et al. |
| 2001/0019818 A1 | 9/2001 | Yong |
| 2002/0168619 A1 | 11/2002 | Provenza |
| 2003/0031993 A1 | 2/2003 | Pugh |
| 2003/0091967 A1 | 5/2003 | Chosack et al. |
| 2003/0176770 A1 | 9/2003 | Merril et al. |
| 2004/0005423 A1 | 1/2004 | Dalton et al. |
| 2004/0126746 A1 | 7/2004 | Toly |
| 2004/0248072 A1 | 12/2004 | Gray et al. |
| 2005/0008997 A1 | 1/2005 | Herman |
| 2005/0026125 A1 | 2/2005 | Toly |
| 2005/0084833 A1 | 4/2005 | Lacey et al. |
| 2005/0131390 A1 | 6/2005 | Heinrich et al. |
| 2005/0142525 A1* | 6/2005 | Cotin ............... G09B 23/285 434/262 |
| 2005/0192595 A1 | 9/2005 | Green et al. |
| 2005/0196739 A1 | 9/2005 | Moriyama |
| 2005/0196740 A1 | 9/2005 | Moriyama |
| 2005/0214727 A1 | 9/2005 | Stoianovici et al. |
| 2006/0046235 A1 | 3/2006 | Alexander et al. |
| 2006/0252019 A1 | 11/2006 | Burkitt et al. |
| 2006/0275741 A1 | 12/2006 | Chewning et al. |
| 2007/0074584 A1 | 4/2007 | Talarico et al. |
| 2007/0077544 A1 | 4/2007 | Lemperle et al. |
| 2007/0078484 A1 | 4/2007 | Talarico et al. |
| 2007/0148626 A1 | 6/2007 | Ikeda |
| 2007/0166682 A1 | 7/2007 | Yarin et al. |
| 2007/0197895 A1 | 8/2007 | Nycz et al. |
| 2007/0225734 A1 | 9/2007 | Bell et al. |
| 2007/0275359 A1 | 11/2007 | Rotnes et al. |
| 2007/0282228 A1* | 12/2007 | Einav ............... A61B 5/16 601/33 |
| 2008/0032272 A1 | 2/2008 | Palakodeti |

(56) References Cited

U.S. PATENT DOCUMENTS

| | | |
|---|---|---|
| 2008/0032273 A1 | 2/2008 | Macnamara et al. |
| 2008/0052034 A1 | 2/2008 | David et al. |
| 2008/0064017 A1 | 3/2008 | Grundmeyer, III |
| 2008/0076101 A1 | 3/2008 | Hyde et al. |
| 2008/0097501 A1 | 4/2008 | Blier |
| 2008/0108869 A1 | 5/2008 | Sanders et al. |
| 2008/0187895 A1 | 8/2008 | Sakezles |
| 2008/0188948 A1 | 8/2008 | Flatt |
| 2008/0299529 A1 | 12/2008 | Schaller |
| 2008/0317818 A1 | 12/2008 | Griffith et al. |
| 2009/0068627 A1 | 3/2009 | Toly |
| 2009/0142739 A1 | 6/2009 | Wang et al. |
| 2009/0142741 A1 | 6/2009 | Ault et al. |
| 2009/0143642 A1 | 6/2009 | Takahashi et al. |
| 2009/0176196 A1 | 7/2009 | Niblock et al. |
| 2009/0187079 A1 | 7/2009 | Albrecht et al. |
| 2009/0246747 A1 | 10/2009 | Buckman, Jr. |
| 2009/0298034 A1 | 12/2009 | Parry et al. |
| 2009/0314550 A1 | 12/2009 | Layton |
| 2010/0047752 A1 | 2/2010 | Chan et al. |
| 2010/0087835 A1* | 4/2010 | Blumenkranz ........ A61B 34/76 606/130 |
| 2010/0094312 A1 | 4/2010 | Ruiz Morales et al. |
| 2010/0099067 A1 | 4/2010 | Agro |
| 2010/0167248 A1 | 7/2010 | Ryan |
| 2010/0167249 A1 | 7/2010 | Ryan |
| 2010/0167250 A1 | 7/2010 | Ryan et al. |
| 2010/0167253 A1* | 7/2010 | Ryan ................ G09B 23/30 434/272 |
| 2010/0167254 A1 | 7/2010 | Nguyen |
| 2010/0196867 A1 | 8/2010 | Geerligs et al. |
| 2010/0204713 A1 | 8/2010 | Ruiz Morales |
| 2010/0209899 A1 | 8/2010 | Park et al. |
| 2010/0248200 A1 | 9/2010 | Ladak |
| 2010/0258611 A1 | 10/2010 | Smith et al. |
| 2010/0273136 A1 | 10/2010 | Kandasami et al. |
| 2010/0279263 A1 | 11/2010 | Duryea |
| 2010/0285094 A1 | 11/2010 | Gupta |
| 2010/0324541 A1 | 12/2010 | Whitman |
| 2011/0020779 A1 | 1/2011 | Hannaford et al. |
| 2011/0046637 A1* | 2/2011 | Patel ................ A61B 17/29 606/130 |
| 2011/0046659 A1 | 2/2011 | Ramstein et al. |
| 2011/0087238 A1 | 4/2011 | Wang et al. |
| 2011/0091855 A1 | 4/2011 | Miyazaki |
| 2011/0137337 A1 | 6/2011 | van den Dool et al. |
| 2011/0200976 A1 | 8/2011 | Hou et al. |
| 2011/0207104 A1 | 8/2011 | Trotta |
| 2011/0218550 A1 | 9/2011 | Ma |
| 2011/0244436 A1 | 10/2011 | Campo |
| 2011/0269109 A2 | 11/2011 | Miyazaki |
| 2011/0281251 A1 | 11/2011 | Mousques |
| 2011/0301620 A1 | 12/2011 | Di Betta et al. |
| 2012/0015337 A1 | 1/2012 | Hendrickson et al. |
| 2012/0015339 A1 | 1/2012 | Hendrickson et al. |
| 2012/0016362 A1 | 1/2012 | Heinrich et al. |
| 2012/0028231 A1 | 2/2012 | Misawa et al. |
| 2012/0045743 A1 | 2/2012 | Okano et al. |
| 2012/0065632 A1 | 3/2012 | Shadduck |
| 2012/0082970 A1 | 4/2012 | Pravong et al. |
| 2012/0100217 A1 | 4/2012 | Green et al. |
| 2012/0115117 A1 | 5/2012 | Marshall |
| 2012/0115118 A1 | 5/2012 | Marshall |
| 2012/0116391 A1 | 5/2012 | Houser et al. |
| 2012/0148994 A1 | 6/2012 | Hori et al. |
| 2012/0164616 A1 | 6/2012 | Endo et al. |
| 2012/0165866 A1 | 6/2012 | Kaiser et al. |
| 2012/0172873 A1 | 7/2012 | Artale et al. |
| 2012/0179072 A1 | 7/2012 | Kegreiss |
| 2012/0202180 A1 | 8/2012 | Stock et al. |
| 2012/0203067 A1* | 8/2012 | Higgins ............... G06K 9/6289 600/117 |
| 2012/0264096 A1 | 10/2012 | Taylor et al. |
| 2012/0264097 A1 | 10/2012 | Newcott et al. |
| 2012/0282583 A1 | 11/2012 | Thaler et al. |
| 2012/0282584 A1 | 11/2012 | Millon et al. |
| 2012/0283707 A1 | 11/2012 | Giordano et al. |
| 2012/0288839 A1 | 11/2012 | Crabtree |
| 2012/0308977 A1 | 12/2012 | Tortola |
| 2013/0087597 A1 | 4/2013 | Shelton, IV et al. |
| 2013/0101973 A1 | 4/2013 | Hoke et al. |
| 2013/0105552 A1 | 5/2013 | Weir et al. |
| 2013/0116668 A1 | 5/2013 | Shelton, IV et al. |
| 2013/0157240 A1 | 6/2013 | Hart et al. |
| 2013/0171288 A1 | 7/2013 | Harders |
| 2013/0177890 A1 | 7/2013 | Sakezles |
| 2013/0192741 A1 | 8/2013 | Trotta et al. |
| 2013/0218166 A1 | 8/2013 | Elmore |
| 2013/0224709 A1 | 8/2013 | Riojas et al. |
| 2013/0245681 A1 | 9/2013 | Straehnz et al. |
| 2013/0253480 A1 | 9/2013 | Kimball et al. |
| 2013/0267876 A1 | 10/2013 | Leckenby et al. |
| 2013/0282038 A1 | 10/2013 | Dannaher et al. |
| 2013/0288216 A1 | 10/2013 | Parry, Jr. et al. |
| 2013/0302771 A1 | 11/2013 | Alderete |
| 2013/0324991 A1 | 12/2013 | Clem et al. |
| 2013/0324999 A1 | 12/2013 | Price et al. |
| 2014/0011172 A1 | 1/2014 | Lowe |
| 2014/0017651 A1 | 1/2014 | Sugimoto et al. |
| 2014/0030682 A1 | 1/2014 | Thilenius |
| 2014/0038151 A1 | 2/2014 | Hart |
| 2014/0051049 A1 | 2/2014 | Jarc et al. |
| 2014/0072941 A1 | 3/2014 | Hendrickson et al. |
| 2014/0087345 A1 | 3/2014 | Breslin et al. |
| 2014/0087346 A1 | 3/2014 | Breslin et al. |
| 2014/0087347 A1 | 3/2014 | Tracy et al. |
| 2014/0087348 A1 | 3/2014 | Tracy et al. |
| 2014/0088413 A1 | 3/2014 | Von Bucsh et al. |
| 2014/0093852 A1 | 4/2014 | Poulsen et al. |
| 2014/0093854 A1 | 4/2014 | Poulsen et al. |
| 2014/0099858 A1 | 4/2014 | Hernandez |
| 2014/0106328 A1 | 4/2014 | Loor |
| 2014/0107471 A1 | 4/2014 | Haider et al. |
| 2014/0156002 A1 | 6/2014 | Thompson et al. |
| 2014/0162016 A1 | 6/2014 | Matsui et al. |
| 2014/0170623 A1 | 6/2014 | Jarstad et al. |
| 2014/0186809 A1 | 7/2014 | Hendrickson et al. |
| 2014/0187855 A1 | 7/2014 | Nagale et al. |
| 2014/0200561 A1 | 7/2014 | Ingmanson et al. |
| 2014/0212861 A1 | 7/2014 | Romano |
| 2014/0220527 A1 | 8/2014 | Li et al. |
| 2014/0220530 A1 | 8/2014 | Merkle et al. |
| 2014/0220532 A1 | 8/2014 | Ghez et al. |
| 2014/0242564 A1 | 8/2014 | Pravong et al. |
| 2014/0246479 A1 | 9/2014 | Baber et al. |
| 2014/0248596 A1 | 9/2014 | Hart et al. |
| 2014/0263538 A1 | 9/2014 | Leimbach et al. |
| 2014/0272878 A1 | 9/2014 | Shim et al. |
| 2014/0272879 A1 | 9/2014 | Shim et al. |
| 2014/0275795 A1 | 9/2014 | Little et al. |
| 2014/0275981 A1 | 9/2014 | Selover et al. |
| 2014/0277017 A1 | 9/2014 | Leimbach et al. |
| 2014/0303643 A1 | 10/2014 | Ha et al. |
| 2014/0303646 A1 | 10/2014 | Morgan et al. |
| 2014/0303660 A1 | 10/2014 | Boyden et al. |
| 2014/0308643 A1 | 10/2014 | Trotta et al. |
| 2014/0342334 A1 | 11/2014 | Black et al. |
| 2014/0349266 A1 | 11/2014 | Choi |
| 2014/0350530 A1 | 11/2014 | Ross et al. |
| 2014/0357977 A1 | 12/2014 | Zhou |
| 2014/0370477 A1 | 12/2014 | Black et al. |
| 2014/0371761 A1 | 12/2014 | Juanpera |
| 2014/0378995 A1 | 12/2014 | Kumar et al. |
| 2015/0031008 A1 | 1/2015 | Black et al. |
| 2015/0037773 A1 | 2/2015 | Quirarte Catano |
| 2015/0038613 A1 | 2/2015 | Sun et al. |
| 2015/0076207 A1 | 3/2015 | Boudreaux et al. |
| 2015/0086955 A1 | 3/2015 | Poniatowski et al. |
| 2015/0132732 A1 | 5/2015 | Hart et al. |
| 2015/0132733 A1 | 5/2015 | Garvik et al. |
| 2015/0135832 A1 | 5/2015 | Blumenkranz et al. |
| 2015/0148660 A1 | 5/2015 | Weiss et al. |
| 2015/0164598 A1 | 6/2015 | Blumenkranz et al. |
| 2015/0187229 A1 | 7/2015 | Wachli et al. |

(56) References Cited

U.S. PATENT DOCUMENTS

| | | |
|---|---|---|
| 2015/0194075 A1 | 7/2015 | Rappel et al. |
| 2015/0202299 A1 | 7/2015 | Burdick et al. |
| 2015/0209035 A1 | 7/2015 | Zemlock |
| 2015/0209059 A1 | 7/2015 | Trees et al. |
| 2015/0209573 A1 | 7/2015 | Hibner et al. |
| 2015/0228206 A1 | 8/2015 | Shim et al. |
| 2015/0262511 A1 | 9/2015 | Lin et al. |
| 2015/0265431 A1 | 9/2015 | Egilsson et al. |
| 2015/0272571 A1 | 10/2015 | Leimbach et al. |
| 2015/0272574 A1 | 10/2015 | Leimbach et al. |
| 2015/0272580 A1 | 10/2015 | Leimbach et al. |
| 2015/0272581 A1 | 10/2015 | Leimbach et al. |
| 2015/0272583 A1 | 10/2015 | Leimbach et al. |
| 2015/0272604 A1 | 10/2015 | Chowaniec et al. |
| 2015/0332609 A1 | 11/2015 | Alexander |
| 2015/0356891 A1* | 12/2015 | Will ................. G09B 23/285 434/272 |
| 2015/0358426 A1 | 12/2015 | Kimball et al. |
| 2015/0371560 A1 | 12/2015 | Lowe |
| 2015/0374378 A1 | 12/2015 | Giordano et al. |
| 2015/0374449 A1 | 12/2015 | Chowaniec et al. |
| 2016/0000437 A1 | 1/2016 | Giordano et al. |
| 2016/0022374 A1 | 1/2016 | Haider et al. |
| 2016/0030240 A1 | 2/2016 | Gonenc et al. |
| 2016/0031091 A1 | 2/2016 | Popovic et al. |
| 2016/0058534 A1 | 3/2016 | Derwin et al. |
| 2016/0066909 A1 | 3/2016 | Baber et al. |
| 2016/0070436 A1 | 3/2016 | Thomas et al. |
| 2016/0073928 A1 | 3/2016 | Soper et al. |
| 2016/0074103 A1 | 3/2016 | Sartor |
| 2016/0098933 A1 | 4/2016 | Reiley et al. |
| 2016/0104394 A1 | 4/2016 | Miyazaki |
| 2016/0117956 A1 | 4/2016 | Larsson et al. |
| 2016/0125762 A1 | 5/2016 | Becker et al. |
| 2016/0133158 A1* | 5/2016 | Sui .................. G09B 23/285 434/262 |
| 2016/0140876 A1 | 5/2016 | Jabbour et al. |
| 2016/0194378 A1 | 7/2016 | Cass et al. |
| 2016/0199059 A1 | 7/2016 | Shelton, IV et al. |
| 2016/0220150 A1 | 8/2016 | Sharonov |
| 2016/0220314 A1 | 8/2016 | Huelman et al. |
| 2016/0225288 A1 | 8/2016 | East et al. |
| 2016/0232819 A1 | 8/2016 | Hofstetter et al. |
| 2016/0235494 A1 | 8/2016 | Shelton, IV et al. |
| 2016/0256187 A1 | 9/2016 | Shelton, IV et al. |
| 2016/0256229 A1 | 9/2016 | Morgan et al. |
| 2016/0262736 A1 | 9/2016 | Ross et al. |
| 2016/0262745 A1 | 9/2016 | Morgan et al. |
| 2016/0293055 A1 | 10/2016 | Hofstetter |
| 2016/0296144 A1 | 10/2016 | Gaddam et al. |
| 2018/0247560 A1* | 8/2018 | Mackenzie ............ G09B 23/28 |

FOREIGN PATENT DOCUMENTS

| | | |
|---|---|---|
| CN | 2909427 Y | 6/2007 |
| CN | 101313842 A | 12/2008 |
| CN | 101528780 A | 9/2009 |
| CN | 201364679 Y | 12/2009 |
| CN | 201955979 U | 8/2011 |
| CN | 102458496 A | 5/2012 |
| CN | 202443680 U | 9/2012 |
| CN | 202563792 U | 11/2012 |
| CN | 202601055 U | 12/2012 |
| CN | 202694651 U | 1/2013 |
| CN | 103050040 A | 4/2013 |
| CN | 203013103 U | 6/2013 |
| CN | 203038549 U | 7/2013 |
| CN | 203338651 U | 12/2013 |
| CN | 203397593 U | 1/2014 |
| CN | 203562128 U | 4/2014 |
| CN | 102596275 B | 6/2014 |
| CN | 103845757 A | 6/2014 |
| CN | 103886797 A | 6/2014 |
| CN | 103396562 B | 7/2015 |
| CN | 105194740 A | 12/2015 |
| CN | 105504166 A | 4/2016 |
| DE | 9102218 U1 | 5/1991 |
| DE | 41 05 892 A1 | 8/1992 |
| DE | 44 14 832 A1 | 11/1995 |
| DE | 19716341 A1 | 9/2000 |
| EP | 1 024 173 A1 | 8/2000 |
| EP | 2 218 570 A1 | 8/2010 |
| FR | 2 691 826 A1 | 12/1993 |
| FR | 2 917 876 A1 | 12/2008 |
| GB | 2488994 A | 9/2012 |
| JP | 10 211160 A | 8/1998 |
| JP | 2001005378 A | 1/2001 |
| JP | 2009236963 A | 10/2009 |
| JP | 3162161 U | 8/2010 |
| JP | 2013127496 A | 6/2013 |
| KR | 101231565 B1 | 2/2013 |
| MX | PA 02004422 A | 11/2003 |
| PT | 106230 | 9/2013 |
| WO | WO 1994/06109 A1 | 3/1994 |
| WO | WO 1996/042076 A1 | 12/1996 |
| WO | WO 1998/58358 A1 | 12/1998 |
| WO | WO 1999/01074 A1 | 1/1999 |
| WO | WO 2000/36577 A1 | 6/2000 |
| WO | WO 2002/38039 A2 | 5/2002 |
| WO | WO 2002/038039 A3 | 5/2002 |
| WO | WO 2004/032095 A1 | 4/2004 |
| WO | WO 2004/082486 A1 | 9/2004 |
| WO | WO 2005/071639 A1 | 8/2005 |
| WO | WO 2006/083963 A2 | 8/2006 |
| WO | WO 2007/068360 A1 | 6/2007 |
| WO | WO 2008/021720 A2 | 2/2008 |
| WO | WO 2008/103383 A1 | 8/2008 |
| WO | WO 2009/000939 A1 | 12/2008 |
| WO | WO 2009/089614 A2 | 7/2009 |
| WO | WO 2010/094730 A1 | 8/2010 |
| WO | WO 2011/035410 A1 | 3/2011 |
| WO | WO 2011/046606 A1 | 4/2011 |
| WO | WO 2011/127379 A2 | 10/2011 |
| WO | WO 2011/151304 A1 | 12/2011 |
| WO | WO 2012/149606 A1 | 11/2012 |
| WO | WO 2012/168287 A1 | 12/2012 |
| WO | WO 2012/175993 A1 | 12/2012 |
| WO | WO 2013/048978 A1 | 4/2013 |
| WO | WO 2013/103956 A1 | 7/2013 |
| WO | WO 2014/022815 A1 | 2/2014 |
| WO | WO 2014/093669 A1 | 6/2014 |
| WO | WO 2014/197793 A1 | 12/2014 |
| WO | WO 2015/148817 A1 | 10/2015 |
| WO | WO 2016/138528 A1 | 9/2016 |
| WO | WO 2016/183412 A1 | 11/2016 |
| WO | WO 2016/198238 A1 | 12/2016 |
| WO | WO 2016/201085 A1 | 12/2016 |
| WO | WO 2017/031214 A1 | 2/2017 |
| WO | WO 2017/042301 A1 | 3/2017 |

OTHER PUBLICATIONS

European Patent Office, The International Search Report and Written Opinion for International Application No. PCT/US2018/018895, entitled "Synthetic Tissue Structures for Electrosurgical Training and Simulation," dated May 17, 2018, 12 pgs.

The International Bureau of WIPO, International Preliminary Report on Patentability for International Application No. PCT/US2016/062669, entitled "Simulated Dissectible Tissue," dated May 31, 2018, 11 pgs.

European Patent Office, The International Search Report and Written Opinion for International Application No. PCT/US2018/018036, entitled "Laparoscopic Training System," dated Jun. 8, 2018, 13 pgs.

European Patent Office, The International Search Report and Written Opinion for International Application No. PCT/US2017/039113, entitled "Simulated Abdominal Wall," dated Aug. 7, 2017, 13 pgs.

Society of Laparoendoscopic Surgeons, "Future Technology Session; The Edge of Innovation in Surgery, Space, and Business," http://www.laparoscopytoday.com/endourology/page/2/, Figure 1B:

(56) References Cited

OTHER PUBLICATIONS http://laparoscopy.blogs.com/laparoscopy_today/images/6-1/6-1VlaovicPicB.jpg , Sep. 5-8, 2007, 10 pgs.
European Patent Office, International Search Report for International Application No. PCT/US2011/053859 A3, dated Apr. 5, 2012, entitled "Portable Laparoscopic Trainer," 8 pgs.
European Patent Office, The International Search Report and Written Opinion for International Application No. PCT/US2012/60997, entitled "Simulated Tissue Structure for Surgical Training," dated Mar. 7, 2013, 8 pgs.
European Patent Office, The International Search Report and Written Opinion for International Application No. PCT/US2012/070971, entitled "Advanced Surgical Simulation," dated Mar. 18, 2013, 10 pgs.
Human Patient Simulator, Medical Education Technologies, Inc., http://www.meti.com (1999) all, printed Apr. 12, 2013, 24 pgs.
The International Bureau of WIPO, International Preliminary Report on Patentability and Written Opinion for International Application No. PCT/US2011/053859, entitled "Portable Laparoscopic Trainer," dated Apr. 2, 2013, 9 pgs.
European Patent Office, The International Search Report and Written Opinion for International Application No. PCT/US2013/062363, entitled "Surgical Training Model for Laparoscopic Procedures," dated Jan. 22, 2014, 11 pgs.
European Patent Office, The International Search Report and Written Opinion for International Application No. PCT/US2013/061949, entitled "Surgical Training Model for Laparoscopic Procedures," dated Feb. 17, 2014, 7 pgs.
Anonymous: Realsim Systems—LTS2000, Sep. 4, 2005, pp. 1-2, XP055096193, Retrieved from the Internet: URL:https://web.archive.org/web/2005090403;3030/http://www.realsimsystems.com/exersizes.htm (retrieved on Jan. 14, 2014).
European Patent Office, The International Search Report and Written Opinion for International Application No. PCT/US2013/062269, entitled "Surgical Training Model for Transluminal Procedures," dated Feb. 17, 2014, 8 pgs.
European Patent Office, The International Search Report and Written Opinion for International Application No. PCT/US2013/061557, entitled "Surgical Training Model for Laparoscopic Procedures," dated Feb. 10, 2014, 9 pgs.
European Patent Office, The International Search Report and Written Opinion for International Application No. PCT/US2013/061728, entitled "Surgical Training Model for Laparoscopic Procedures," dated Oct. 18, 2013, 9 pgs.
Limps and Things, EP Guildford MATTU Hernia Trainer, http://limbsandthings.com/us/products/tep-guildford-mattu-hernia-trainer/, printed May 29, 2014, 11 pgs.
Simulab, Hernia Model, http://www.simulab.com/product/surgery/open/hernia model, printed May 29, 2014, 4 pgs.
McGill Laparoscopic Inguinal Hernia Simulator, Novel Low-Cost Simulator for Laparoscopic Inguinal Hernia Repair, Feb. 8, 2011, 1 pg.
University of Wisconsin-Madison Biomedical Engineering, Inguinal Hernia Model, http://bmedesign.engr.wisc.edu/projects/s10/hernia_model/, printed May 29, 2014, 62 pgs.
The International Bureau of WIPO, International Preliminary Report on Patentability for International Application No. PCT/US2012/070971, entitled "Advanced Surgical Simulation," dated Jun. 24, 2014, 7 pgs.
European Patent Office, The International Search Report and Written Opinion of the International Searching Authority for International Application No. PCT/US2014/038195, entitled "Hernia Model", dated Oct. 15, 2014, 20 pgs.
European Patent Office, The International Search Report and Written Opinion of the International Searching Authority for International Application No. PCT/US2014/048027, entitled "First Entry Model", dated Oct. 17, 2014, 10 pgs.

The International Bureau of WIPO, International Preliminary Report on Patentability for International Application No. PCT/US2012/060997, entitled "Simulated Tissue Structure for Surgical Training" dated Apr. 22, 2014, 6 pgs.
European Patent Office, The International Search Report and Written Opinion for International Application No. PCT/US2014/019840, entitled "Advanced Surgical Simulation Constructions and Methods," dated Jul. 4, 2014, 8 pgs.
Kurashima, et al, "A tool for training and evaluation of Laparoscopic inguinal hernia repair; the Global Operative Assessment of Laparoscopic Skills-Groin Hernia" American Journal of Surgery, Paul Hoeber, New York, NY, US vol. 201, No. 1, Jan. 1, 2011, pp. 54-61 XP027558745.
European Patent Office, The International Search Report and Written Opinion for International Application No. PCT/US2014/042998, entitled "Gallbladder Model," dated Jan. 7, 2015, 20 pgs.
The International Bureau of WIPO, International Preliminary Report on Patentability, for PCT application No. PCT/US2013/053497, entitled Simulated Stapling and Energy Based Ligation for Surgical Training, dated Feb. 12, 2015, 6 pgs.
The International Bureau of WIPO, International Preliminary Report on Patentability for International Application No. PCT/US2013/062363, entitled "Surgical Training Model for Laparoscopic Procedures," dated Apr. 9, 2015, 9 pgs.
The International Bureau of WIPO, International Preliminary Report on Patentability for International Application No. PCT/US2013/062269, entitled "Surgical Training Model for Laparoscopic Procedures," dated Apr. 9, 2015, 6 pgs.
The International Bureau of WIPO, International Preliminary Report on Patentability for International Application No. PCT/US2013/061557, entitled "Surgical Training Model for Laparoscopic Procedures," dated Apr. 9, 2015, 6 pgs.
The International Bureau of WIPO, International Preliminary Report on Patentability for International Application No. PCT/US2013/061728, entitled "Surgical Training Model for Laparoscopic Procedures," dated Apr. 9, 2015, 7 pgs.
The International Bureau of WIPO, International Preliminary Report on Patentability for International Application No. PCT/US2013/061949, entitled "Surgical Training Model for Laparoscopic Procedures," dated Apr. 9, 2015, 6 pgs.
The International Bureau of WIPO, International Preliminary Report on Patentability for International Application No. PCT/US2014/019840, entitled "Simulated Tissue Structure for Surgical Training," dated Sep. 11, 2015, 8 pgs.
European Patent Office, The International Search Report and Written Opinion for International Application No. PCT/US2015/020574, entitled "Advanced First Entry Model for Surgical Simulation," dated Jun. 1, 2015, 12 pgs.
European Patent Office, The International Search Report and Written Opinion for International Application No. PCT/US2015/022774, entitled "Simulated Dissectible Tissue," dated Jun. 11, 2015, 13 pgs.
Anonymous: Silicone rubber-from Wikipedia, the free encyclopedia, pp. 1-6, XP055192375, Retrieved from the Internet: URL:http://en.wikipedia.org/w.index.php?title=Silicone_rubber&oldid=596456058 (retrieved on May 29, 2015).
Lamouche, et al., "Review of tissue simulating phantoms with controllable optical, mechanical and structural properties for use in optical coherence tomography," Biomedical Optics Express, Jun. 1, 2012, 18 pgs., vol. 3, No. 6.
The International Bureau of WIPO, International Preliminary Report on Patentability for International Application No. PCT/US2014/038195, entitled "Hernia Model," dated Nov. 26, 2015, 16 pgs.
The International Bureau of WIPO, International Preliminary Report on Patentability for International Application No. PCT/US2014/042998, entitled "Gallbladder Model," dated Dec. 30, 2015, 15 pgs.
European Patent Office, International Search Report and Written Opinion for International Application No. PCT/US2013/053497, titled "Simulated Stapling and Energy Based Ligation for Surgical Training," dated Nov. 5, 2013, 8 pgs.
The International Bureau of WIPO, International Preliminary Report on Patentability for International Application No. PCT/US2014/048027, entitled "First Entry Model," dated Feb. 4, 2016, 8 pgs.

(56) References Cited

OTHER PUBLICATIONS

European Patent Office, International Search Report and Written Opinion for International Application No. PCT/US2015/059668, entitled "Simulated Tissue Models and Methods," dated Apr. 26, 2016, 20 pgs.
Australian Patent Office, Patent Examination Report No. 1 for Australian Application No. 2012358851, titled "Advanced Surgical Simulation," dated May 26, 2016, 3 pgs.
Miyazaki Enterprises, "Miya Model Pelvic Surgery Training Model and Video," www.miyazakienterprises, printed Jul. 1, 2016, 1 pg.
European Patent Office, International Search Report and Written Opinion for International Application No. PCT/US2016/032292, entitled "Synthetic Tissue Structures for Electrosurgical Training and Simulation," dated Jul. 14, 2016, 11 pgs.
European Patent Office, International Search Report and Written Opinion for International Application No. PCT/US2016/018697, entitled "Simulated Tissue Structures and Methods," dated Jul. 14, 2016, 21 pgs.
European Patent Office, International Search Report and Written Opinion for International Application No. PCT/US2016/034591, entitled "Surgical Training Model for Laparoscopic Procedures," dated Aug. 8, 2016, 18 pgs.
European Patent Office, The International Search Report and Written Opinion of the International Searching Authority for International Application No. PCT/US2016/036664, entitled "Hysterectomy Model", dated Aug. 19, 2016, 15 pgs.
The International Bureau of WIPO, International Preliminary Report on Patentability for International Application No. PCT/US2015/020574, entitled "Advanced First Entry Model for Surgical Simulation," dated Sep. 22, 2016, 9 pgs.
European Patent Office, The International Search Report and Written Opinion of the International Searching Authority for International Application No. PCT/US2016/0043277 titled "Appendectomy Model", dated Oct. 4, 2016, 12 pgs.
The International Bureau of WIPO, International Preliminary Report on Patentability for International Application No. PCT/US2015/022774, titled "Simulated Dissectible Tissue," dated Oct. 6, 2016, 9 pgs.
European Patent Office, The International Search Report and Written Opinion of the International Searching Authority for International Application No. PCT/US2016/041852 titled "Simulated Dissectible Tissue", dated Oct. 13, 2016, 12 pgs.
European Patent Office, Invitation to Pay Additional Fees for International Application No. PCT/US2016/062669, titled "Simulated Dissectible Tissue", dated Feb. 10, 2017, 8 pgs.
European Patent Office, The International Search Report and Written Opinion of the International Searching Authority for International Application No. PCT/US2016/055148 titled "Hysterectomy Model", dated Feb. 28, 2017, 12 pgs.
European Patent Office, The International Search Report and Written Opinion of the International Searching Authority for International Application No. PCT/US2016/062669 titled "Simulated Dissectible Tissue", dated Apr. 5, 2017, 19 pgs.
European Patent Office, Examination Report for European Application No. 14733949.3 titled "Gallbladder Model," dated Dec. 21, 2016, 6 pgs.
European Patent Office, The International Search Report and Written Opinion of the International Searching Authority for International Application No. PCT/US2017/020389 titled "Simulated Tissue Cartridge", dated May 24, 2017, 13 pgs.

The International Bureau of WIPO, International Preliminary Report on Patentability for International Application No. PCT/US2015/059668, entitled "Simulated Tissue Models and Methods," dated May 26, 2017, 16 pgs.
The International Bureau of WIPO, International Preliminary Report on Patentability for International Application No. PCT/US2016/018697, entitled "Simulated Tissue Structures and Methods," dated Aug. 31, 2017, 14 pgs.
The International Bureau of WIPO, International Preliminary Report on Patentability for International Application No. PCT/US2016/0032292, entitled "Synthetic Tissue Structures for Electrosurgical Training and Simulation," dated Nov. 23, 2017, 8 pgs.
The International Bureau of WIPO, International Preliminary Report on Patentability for International Application No. PCT/US2016/034591, entitled "Surgical Training Model for Laparoscopic Procedures," dated Dec. 7, 2017, 14 pgs.
The International Bureau of WIPO, International Preliminary Report on Patentability for International Application No. PCT/US2016/036664, entitled "Hysterectomy Model," dated Dec. 21, 2017, 10 pgs.
The International Bureau of WIPO, International Preliminary Report on Patentability for International Application No. PCT/US2016/041852, entitled "Simulated Dissectible Tissue," dated Jan. 25, 2018, 12 pgs.
European Patent Office, Extended European Search Report for European Patent Application No. Ep 17202365.7, titled "Gallbladder Model", dated Jan. 31, 2018, 8 pgs.
The International Bureau of WIPO, International Preliminary Report on Patentability for International Application No. PCT/US2016/043277, entitled "Appendectomy Model," dated Feb. 1, 2018, 9 pgs.
3D-MED Corporation, "Validated Training Course for Laparoscopic Skills", https://www.3-dmed.com/sites/default/files/product-additional/product-spec/Validated%20Training%20Course%20for%20Laparoscopie%20Skills.docx_3.pdf , printed Aug. 23, 2016, pp. 1-6.
3D-Med Corporation, "Loops and Wire #1," https://www.3-dmed.com/product/loops-and-wire-1 , printed Aug. 23, 2016, 4 pgs.
Barrier, et al., "A Novel and Inexpensive Vaginal Hysterectomy Simulatory, "Simulation in Healthcare: The Journal of the Society for Simulation in Healthcare, vol. 7, No. 6, Dec. 1, 2012, pp. 374-379.
European Patent Office, Extended European Search Report for European Patent Application No. EP 18177751.7, titled "Portable Laparoscopic Trainer," dated Jul. 13, 2018, 8 pgs.
European Patent Office, The International Search Report and Written Opinion for International Application No. PCT/US2018/034705, entitled "Laparoscopic Training System," dated Aug. 20, 2018, 14 pgs.
The International Bureau of WIPO, International Preliminary Report on Patentability for International Application No. PCT/US2017/020389, entitled "Simulated Tissue Cartridge," dated Sep. 13, 2018, 8 pgs.
European Patent Office, Extended European Search Report for European Patent Application No. EP 18184147.9, titled "First Entry Model," dated Nov. 7, 2018, 7 pgs.
The International Bureau of WIPO, International Preliminary Report on Patentability for International Application No. PCT/US2017/039113, entitled "Simulated Abdominal Wall," dated Jan. 10, 2019, 8 pgs.

* cited by examiner

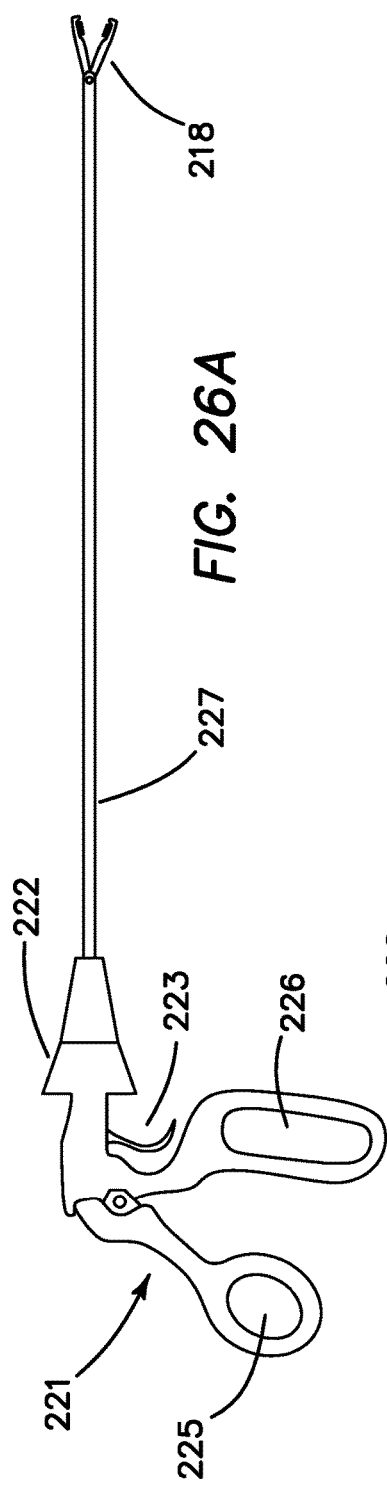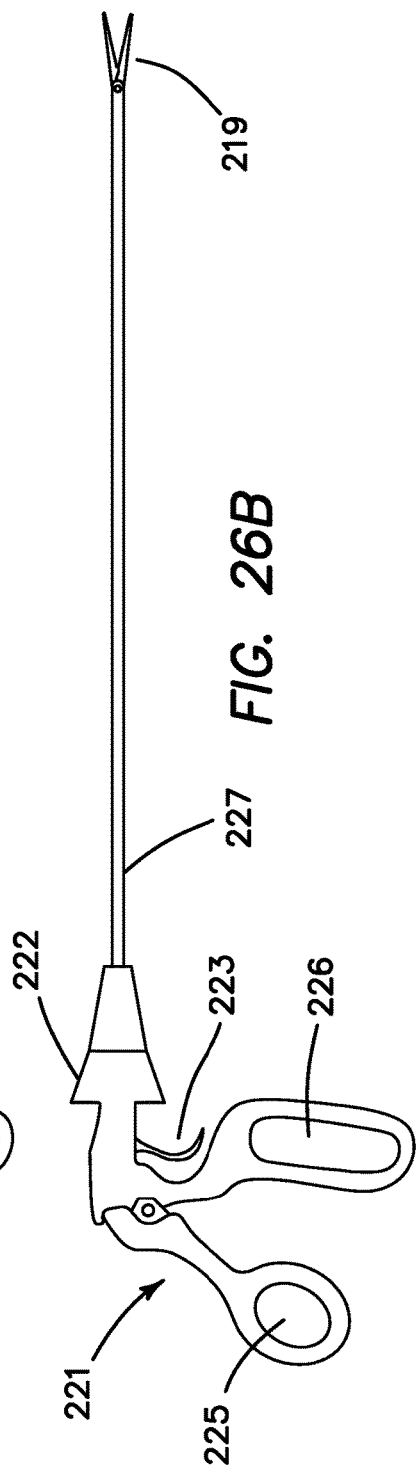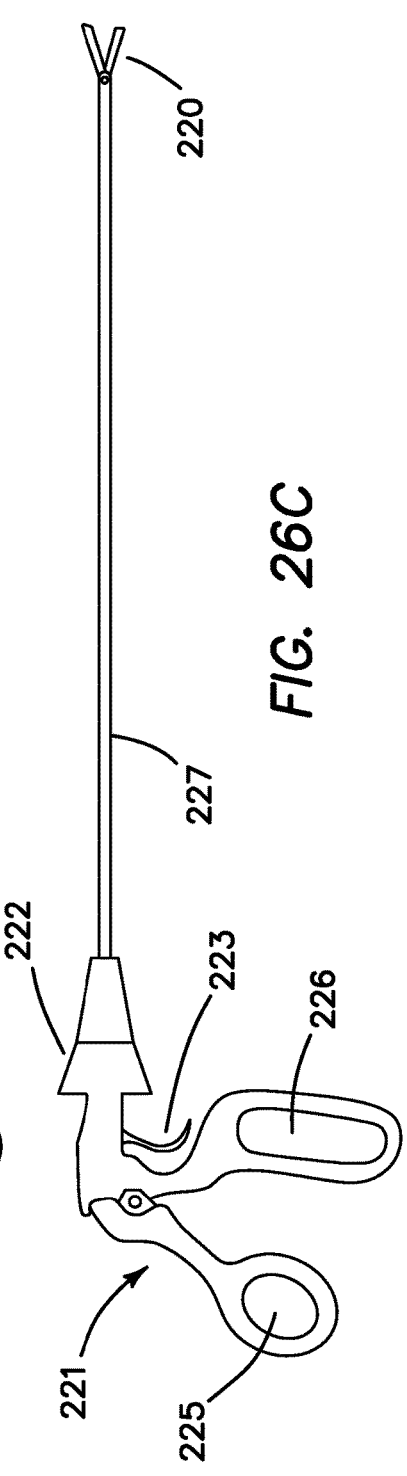

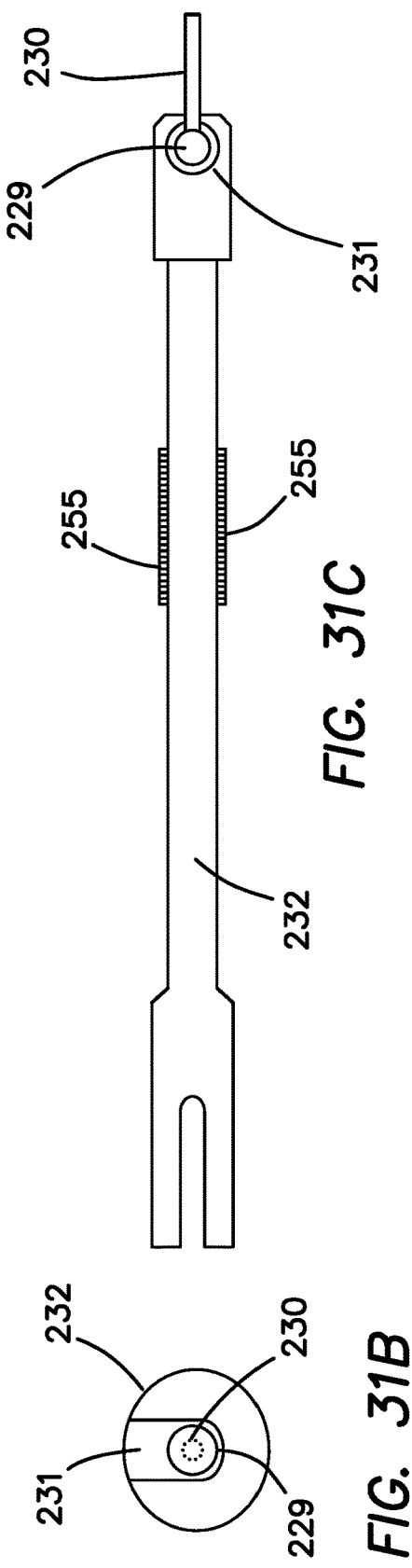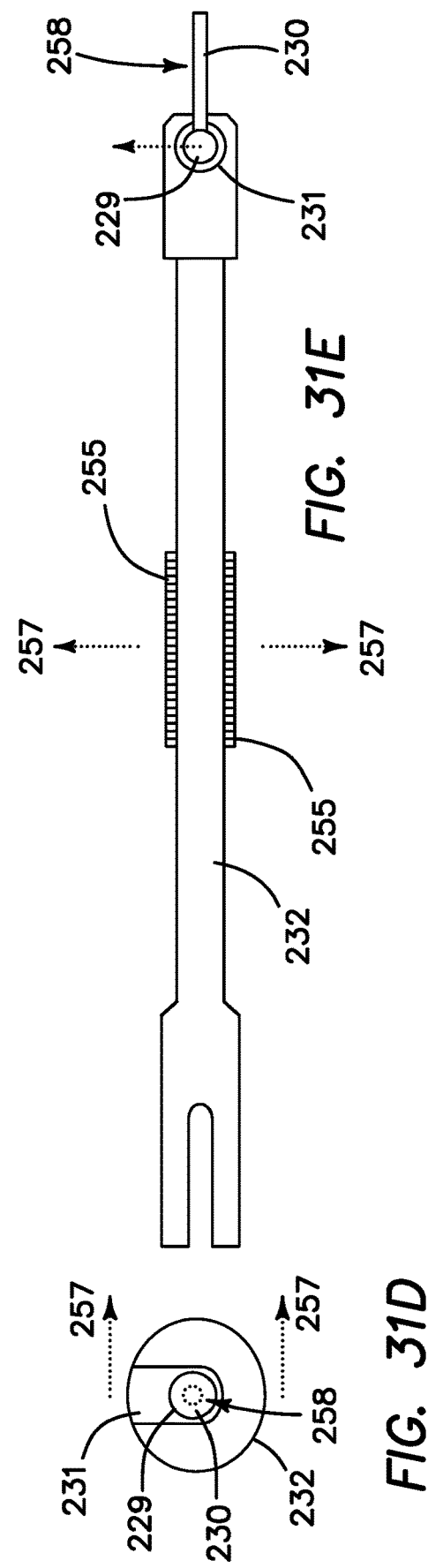

ACCELEROMETER CALIBRATION

Calibration Offset Values:

$Acc_{calibration\_x} = Avg(gravity_{pos\_x}, gravity_{neg\_x})$
$Acc_{calibration\_y} = Avg(gravity_{pos\_y}, gravity_{neg\_y})$
$Acc_{calibration\_z} = Avg(gravity_{pos\_z}, gravity_{neg\_z})$ Smoothness

*Curvature of 2D curve:*

$$K = \frac{|x'y'' - y'x''|}{(x'^2 - y'^2)^{3/2}}$$  513

*Smoothness of Curvature, κ:*

$$smoothness = \frac{stdev(diff(K))}{|mean(diff(K))|}$$  514

FIG. 40

QUESTIONNAIRE

BEFORE WE BEGIN

What is your title?

| Student | PGY 1-2 | PGY 3-5 | Fellow | Attending | Other |

Whay has been your experience with assisting and performing laparoscopic procedures? Number of procedures assisted? [100], performed? [10]

How many laparoscopic procedures have you performed in the last year, Excluding assists?

| Less than 10 | 11-20 | 21-50 | 51-100 | More than 100 |

Which is your dominant hand?

| Left | Right | Ambidextrous |

NEXT

LAPAROSCOPIC TRAINING SYSTEM

CROSS-REFERENCE TO RELATED APPLICATIONS

This application claims priority to and benefit of U.S. Provisional Patent Application Ser. No. 62/458,972 entitled "Laparoscopic training system" filed on Feb. 14, 2017 and incorporated herein by reference in its entirety.

FIELD OF THE INVENTION

This application relates to surgical training, and in particular, to laparoscopic training wherein a simulated torso is used to practice surgical procedures and techniques and an evaluative system provides feedback on the user's performance.

BACKGROUND OF THE INVENTION

Laparoscopic surgery requires several small incisions in the abdomen for the insertion of trocars or small cylindrical tubes approximately 5 to 10 millimeters in diameter through which surgical instruments and a laparoscope are placed into the abdominal cavity. The laparoscope illuminates the surgical field and sends a magnified image from inside the body to a video monitor giving the surgeon a close-up view of the organs and tissues. The surgeon watches the live video feed and performs the operation by manipulating the surgical instruments placed through the trocars.

Minimally invasive surgical techniques performed laparoscopically can greatly improve patient outcomes because of greatly reduced trauma to the body. There is, however, a steep learning curve associated with minimally invasive surgery, which necessitates a method of training surgeons on these challenging techniques. There are a number of laparoscopic simulators on the market, most of which consist of some type of enclosure, and some type of barrier which can be pierced by surgical instruments in order to gain access to the interior. A simulated organ or practice station is placed inside the interior and surgical techniques are practiced on the simulated organ or practice station.

SUMMARY OF THE INVENTION

According to one aspect of the invention, an instrument for surgical training is provided. The instrument includes a handle assembly and a shaft assembly. The handle assembly includes a movement arm having a distal end and a proximal end mechanically connected to a handle, trigger or other appropriate control mechanism. The shaft assembly is removable and interchangeable with the handle assembly. The shaft assembly has a proximal end and a distal end and defines a lumen therebetween. The shaft assembly includes a tool element at the distal end and a rod having a proximal end and a distal end mechanically connected to the tool element. The rod is located inside the lumen. The proximal end of the shaft assembly is removably connectable to the handle assembly such that the proximal end of the rod is connected to the distal end of the movement arm. Actuation at the handle assembly moves the movement arm and rod to operate the tool element. At least one sensor is attached directly to the handle assembly and configured to acquire and transmit at least one relational data of the instrument with respect to a training environment during a training procedure. A computer system is connected to the at least one sensor and is configured to receive, store and process the data and to output at least one feedback information to a user on a computer screen after the training procedure is completed.

According to another aspect of the invention, a method for surgical training is provided. The method includes the step of providing at least one surgical instrument having a handle assembly connected to an interchangeable shaft assembly. The surgical instrument includes a strain gauge, an accelerometer, a gyroscope and a magnetometer all directly attached to the handle assembly, operably connected to a computer, and configured to acquire at least one data. The method includes the step of providing a laparoscopic trainer and at least one simulated tissue located inside the laparoscopic trainer. The method includes the step of providing to the user a group of predefined surgical procedures on the computer screen. The method includes the step of selecting a predefined surgical procedure from the group of predefined surgical procedures. The method includes the step of performing the selected predefined surgical procedure by at least one user using the at least one surgical instrument upon the at least one simulated tissue located inside the laparoscopic trainer. The method includes the step of collecting data from one or more of the strain gauge, accelerometer, gyroscope, and magnetometer. The data is related to the selected predefined surgical procedure. The method includes the step of calculating at least one information from the data. The method includes the step of providing on the computer screen the at least one information and/or data to the user upon completion of the selected predefined surgical procedure. The at least one information and/or data is based on data collected for the at least one user.

According to another aspect of the invention, a laparoscopic trainer is provided. The trainer includes a bottom, at least one sidewall encompassing the bottom and a penetrable simulated abdominal wall defining at least a portion of a top of the trainer. The top is spaced apart from the bottom to define an interior bounded by the at least one sidewall. The at least one sidewall includes a door configured to open and close to provide access to the interior. The door has an aperture extending from the outside of the trainer to the interior to provide access to the interior via the aperture and an interchangeable adapter extending between the top and bottom and fixedly yet removably connected to the trainer in the location of the aperture.

BRIEF DESCRIPTION OF THE DRAWINGS

FIG. 26A is a side elevational view of a laparoscopic grasper instrument according to the present invention.

FIG. 26B is a side elevational view of a laparoscopic scissor instrument according to the present invention.

FIG. 26C is a side elevational view of a laparoscopic dissector instrument according to the present invention.

FIG. 31B is an end view of a movement arm and section of a rod of a surgical instrument according to the present invention.

FIG. 31C is a top, section view of a movement arm and rod of a surgical instrument according to the present invention.

FIG. 31D is an end view of a movement arm and section of a rod of a surgical instrument according to the present invention.

FIG. 31E is a top, section view of a movement arm and rod of a surgical instrument according to the present invention.

FIG. 40 illustrates a smoothness algorithm and an equation used for curvature calculations according to the present invention.

FIG. 46 is a computer screen shot view of a user interface questionnaire screen according to the present invention.

DETAILED DESCRIPTION OF THE INVENTION

Figure 1:
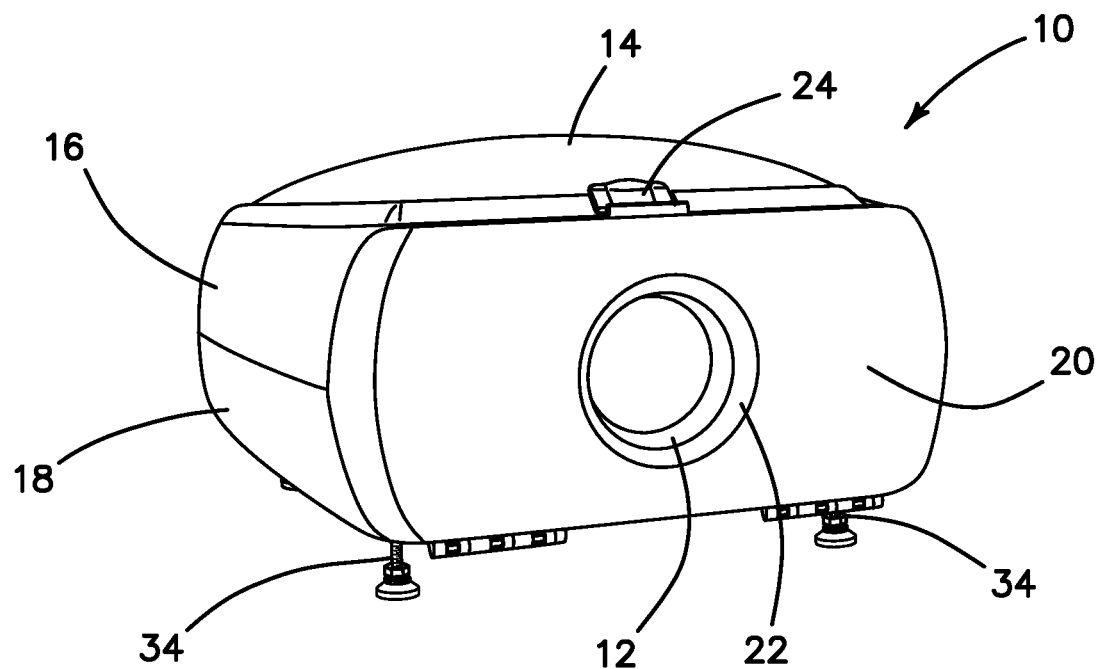
FIG. 1 is a perspective view of a surgical training device according to the present invention.
Figure 2:
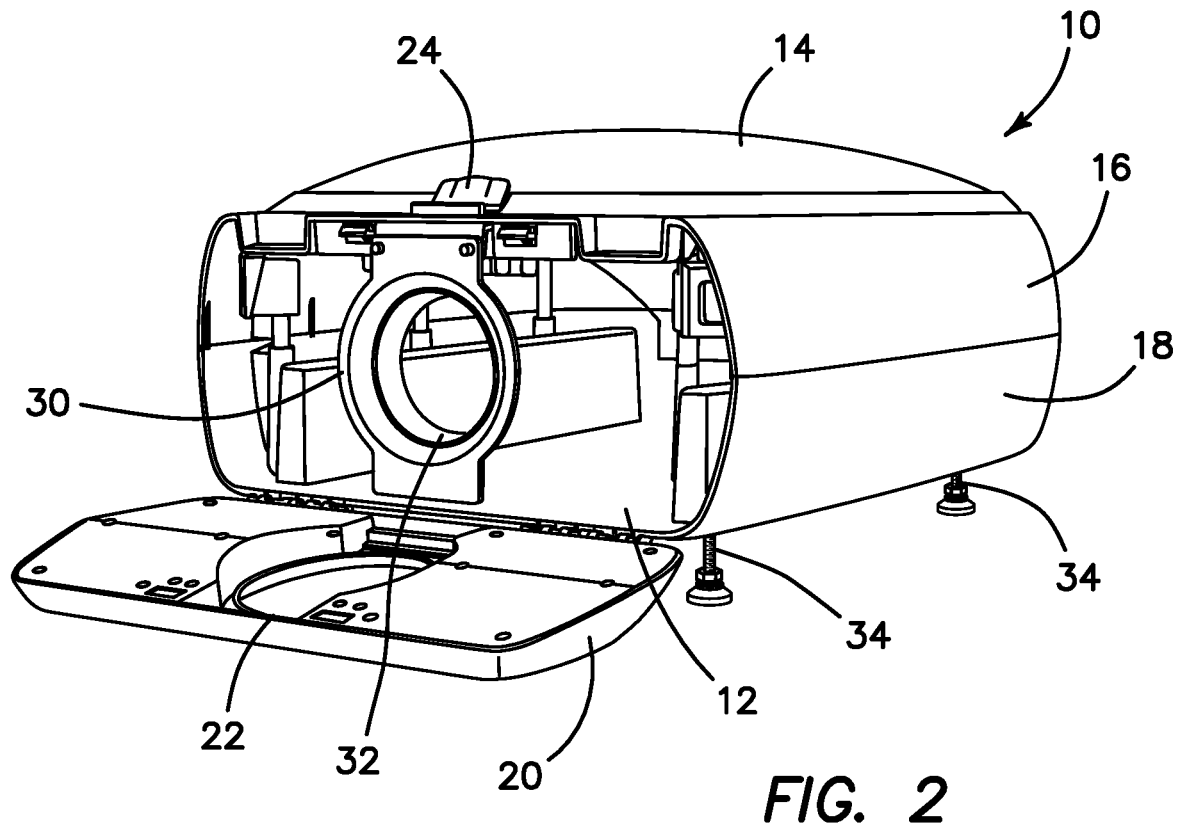
FIG. 2 is a perspective view of a surgical training device according to the present invention.
Figure 3:
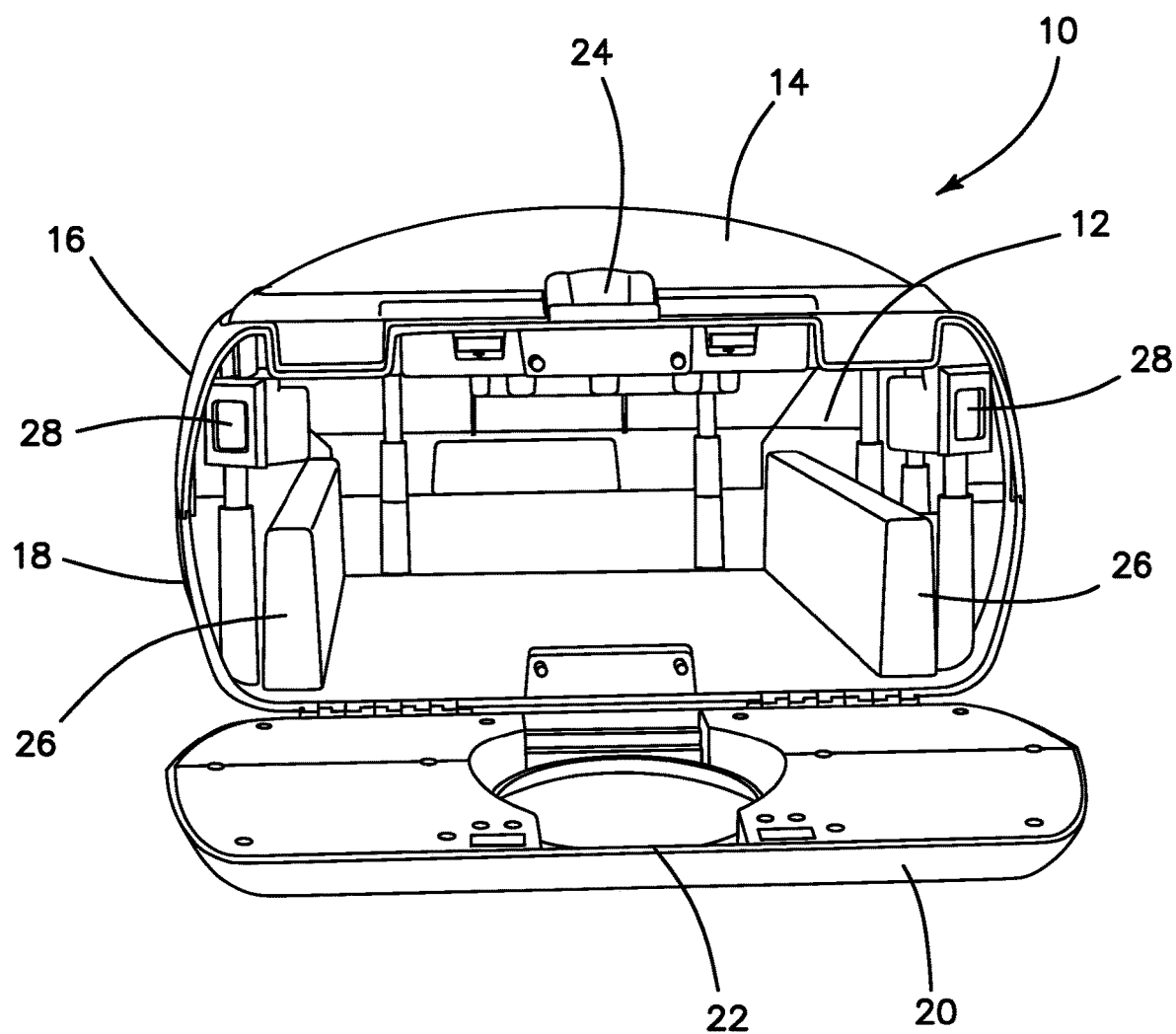
FIG. 3 is a perspective view of a surgical training device according to the present invention.

Turning now to FIGS. 1-3, there is shown a surgical training device 10 that allows a trainee to practice intricate surgical maneuvers in an environment that is safe and inexpensive. The device 10 is generally configured to mimic the torso of a patient, specifically the abdominal region. The surgical training device 10 provides an enclosure for simulating a body cavity 12 that is substantially obscured from the user. The cavity 12 is sized and configured for receiving simulated or live tissue or model organs or skill training models and the like. The body cavity 12 and the enclosed simulated organs and/or models are accessed via a penetrable tissue simulation region 14 that is penetrated by the user employing devices such as trocars to practice surgical techniques and procedures using real surgical instruments such as but not limited to graspers, dissectors, scissors and energy-based fusion and cutting devices on the simulated tissue or models found located in the body cavity 12. The surgical training device 10 is particularly well suited for practicing laparoscopic or other minimally invasive surgical procedures.

Still referencing FIG. 1, the surgical training device 10 includes a top cover 16 connected to and spaced apart from a base 18. The top cover 16 includes an integrally formed depending portion and the base 18 includes an upwardly extending portion both of which cooperate to form the sidewalls and backwall of the surgical training device 10. The surgical training device 10 includes a frontwall 20 that is hinged to the base 18 to form a door that opens to the cavity 12. The frontwall 20 includes a front opening 22 that provides lateral, side access to the cavity 12 which is useful for practicing vaginal hysterectomies and transanal procedures. The frontwall 20 is shown in a closed position in FIG. 1 and in an open position in FIGS. 2-3. A latch 24 is provided and configured to release the tissue simulation region 14 from the top cover 16. Another release button is configured to open the door. The tissue simulation region 14 is representative of the anterior surface of the patient and the cavity 12 between the top cover 16 and the base 18 is representative of an interior abdominal region of the patient where organs reside. The top cover 16 includes an opening that is configured to receive the tissue simulation region 14. The tissue simulation region 14 is convex from the outside to simulate an insufflated abdomen. The tissue simulation region 14 includes numerous layers representing muscle, fat and other layers as described in U.S. Pat. No. 8,764,452 issued to Applied Medical Resources Corporation and incorporated herein by reference in its entirety. The tissue simulation region 14 will be described in greater detail below. The base 18 includes rails 26 shown in FIG. 3 that extend upwardly from the bottom surface inside the cavity 12. The rails 26 are configured to receive a tray (not shown) that carries simulated or live tissue. The tray is useful for an arrangement comprising a plurality of organs and/or retaining fluid or simulated organs made of hydrogel and the like. The tray is placed through the front opening and onto the rails upon which it can then slide into the cavity 12. The tray includes a base on which artificial organs are supported. This base is located above the bottom floor of the laparoscopic trainer. A customized tray having a certain depth allows the height of the organs to be adjusted with respect to the rails by selecting the appropriate depth tray according to the demands of selected surgical procedure. The rails advantageously permit deeper trays to carry more artificial organs or to customize the distance between the top of the artificial organs and the simulated abdominal wall. A shorter distance such as provided by a shallower tray provides a smaller working space for surgical instruments and may increase the difficulty and/or increase the realism of the procedure. Hence, the rails permit a second platform for artificial organs other than the bottom floor of the trainer which is considered as the first platform for artificial organs. The second platform is adjustable by interchanging trays placing the artificial organs therein and sliding the tray onto the rails 26. Lights such as a strip of light emitting diodes (LEDs), sensors and video cameras all generally designated by reference number 28 may also be provided within the cavity 12. The surgical training device 10 is also provided with a removable adapter 30. The adapter 30 extends between and connects with the top cover 16 and base 18. The adapter 30 includes an aperture 32 that is cylindrical in shape and is sized and configured for connecting with a simulated organ such as a simulated vagina or colon and particularly useful for practicing lateral access procedures including but not limited to vaginal hysterectomies and transanal procedures. When a lumen-shaped artificial organ is connected to the adapter the aperture 32 is in communication with the lumen interior. The opening 22 in the frontwall 20 is also in communication with the lumen interior providing access into the lumen from outside the trainer. The adapter 30 connects to prongs in both the top cover 16 and the base 18. When connected, the aperture of the adapter 30 aligns with the opening 22 in the frontwall 20 and is located behind the frontwall 20. The backside of the frontwall 20 may include a recess sized and configured to receive the adapter 30 making it substantially flush with the front side of the frontwall 20. The frontwall 20 when closed and locked also aids in keeping the adapter secure especially when a procedure requires significant force to be applied on the artificial organ. The adapter 30 is interchangeable with an adapter that does not have an aperture 32 and is blank such that, when it is connected to the surgical training device, the opening 22 in the frontwall 20 is covered and light is not permitted to enter the cavity. The blank adapter is employed when the simulation does not require lateral access to the cavity. The base 18 further includes height adjustable legs 34 to accommodate common patient positioning, patient height and angles. In one variation, the legs 34 are made of soft silicone molded around hardware. The hardware includes a cap screw, tee nut and a spacer. The spacer made of nylon provides a hard stop that contacts the bottom of the base once the legs are screwed in so that each leg is the same length. The tee nut is used to grip the silicone foot to prevent it from spinning independently from the cap screw. The distal end of each of the legs is provided with silicone molded foot. The silicone feet are semi-spherical and allow the unit to self-level and dampen vibrations because of the soft silicone composition.

The surgical training device 10 has an elegant and simple design with the ability to simulate different body types such as patients with high body mass index. The trainer 10 can be used by one or more people at the same time and has a large area in the tissue simulation region to accommodate trocar/port placement for a variety of common procedures. The device 10 is configured to resemble a pre-insufflated abdomen and, therefore, more anatomically accurate than other trainers that are simply box-like or do not have large tissue simulation regions curved to simulated an insufflated abdomen. The interior cavity 12 is configured to receive a tray that can slide on the rails 26 into the cavity 12 such that moist/wet live or simulated organs made of hydrogel material can be utilized in the practice of electrosurgical techniques. The rails 26 also advantageously permit the floor of the inserted tray to be closer to the tissue simulation region reducing the vertical distance therebetween. The device 10 is also conveniently portable by one person.

The surgical trainer 10 is a useful tool for teaching, practicing and demonstrating various surgical procedures and their related instruments in simulation of a patient undergoing a surgical procedure. Surgical instruments are inserted into the cavity 12 through the tissue simulation region 14. Various tools and techniques may be used to penetrate the top cover 16 to perform mock procedures on simulated organs or practice models placed between the top cover 16 and the base 18. An external video display monitor connectable to a variety of visual systems for delivering an image to the monitor may be provided. For example, a laparoscope inserted through the tissue simulation region 14 connected to a video monitor or computer can be used to observe record and analyze the simulated procedure. The surgical instruments used in the procedure may also be sensorized and connected to a computer. Also, video recording is provided via the laparoscope to record the simulated procedure.

There are a number of ways that the tissue simulation region can be made. One exemplary variation is the tissue simulation region being simulated as an abdominal wall. Previous versions have used layers of different types of flat foam and/or silicone sheets to simulate the look and/or feel of the different types of tissue present in the human abdominal wall. The sheets simulating an abdominal wall are curved in one or more direction.

One problem with previous versions is that the simulated abdominal wall requires some type of support structure to prevent collapse or buckling of the simulated abdominal wall during use. The support structure holding the simulated abdominal wall generally detracts from the overall feel and visual effect of the simulated abdominal wall, and often gets in the way during simulated procedures, especially during trocar placement.

An aesthetic shortcoming of this type of simulated abdominal wall is that the foam can only be made to curve in one direction, which greatly detracts from its realism. An actual insufflated abdomen curves in multiple directions, and it is a goal of the present invention to create a more lifelike simulation.

An abdominal wall with realistic curvature and landmarks is desirable for the training of proper port placement. Proper port placement allows safe access to the abdominal cavity and adequate triangulation for accessing the key anatomical structures throughout a simulated surgical procedure.

The simulated abdominal wall for use with the surgical training device 10 and its method of manufacture will now be described in greater detail. The simulated abdominal wall is a layered foam abdominal wall that has no need for additional internal or external support structures, and has the visual appeal of a truly convex surface with appropriate landmarks. The method of making the simulated abdominal wall involves laminating multiple layers of foam with the use of adhesive. As each subsequent layer of foam is added, the overall structure becomes more rigid. After several layers have been added, the simulated abdominal wall will tend to spring back to its original shape, even after being severely deformed, and retain enough rigidity to allow realistic puncture by trocars. The simulated abdominal wall has the convex visual appearance of an insufflated human abdomen. Also, the simulated abdominal wall of the present invention allows the user to place a trocar anywhere through its surface without interference from unrealistic underlying support structures. The simulated abdominal wall can withstand repeated use. Previous simulated abdomens have a rubber-like skin layer that is not bonded to the supporting foam materials, resulting in a simulated abdominal wall that appears worn only after one or two uses. A skin layer comprised of silicone mechanically bonded to an underlying foam layer has been created and integrated into the simulated abdominal wall. Because the silicone is securely bonded to the underlying foam, a much more durable skin layer is realized, and costs are driven down by reducing the frequency of abdominal wall replacement. Furthermore, in previous versions where the outer skin layer is not bound to the underlying layers, unrealistic spaces open up between the simulated abdominal wall layers during port placement. The present invention eliminates this issue. A method has been developed to give shape to the simulated abdominal wall. This method meets the aforementioned goals, and is described in reference to the figures.

The method involves the use of a vacuum mold to form and join convex foam sheets. In the process, a foam sheet is placed on the vacuum mold and held in place with a frame. The vacuum pump is then turned on, and heat is applied to the foam. The heat relaxes the foam, allowing it to yield and stretch into and conform to the shape of the mold cavity due to the suction of the vacuum. Spray adhesive is applied to the foam in the mold and/or to a new sheet of foam. Next, a multitude of holes are poked through the first layer of foam so that the vacuum can act on the second layer of foam through the first. The order of hole-poking and glue application can be reversed and the process will still work. The frame is removed, the next sheet of foam is placed glue side down onto the vacuum mold (with the first foam layer still in place, glue side up), and the frame is replaced. Again, the vacuum pump is turned on and heat is applied to the top foam layer. As the two foam layers come into contact they are bonded together. This process is then repeated for each desired foam layer. With the addition of each foam layer, the simulated abdominal wall gains strength.

Once the desired foam layer configuration is completed, the simulated abdominal wall is then inserted into the abdominal wall frame. The abdominal wall frame is a two-piece component that secures the simulated abdominal wall around the perimeter by compressing it between the top and bottom frame parts, and allows the user to easily install and remove the wall from the surgical simulator enclosure. The geometry of the abdominal wall frame adds further support to the convex form and feel of the simulated abdominal wall by utilizing an angled channel along the perimeter that the simulated abdominal wall is compressed between.

The method described hereinbelow relies on a bent lamination mechanism formed, in part, by successively gluing surfaces together that have been made to curve. A structure that maintains the desired curvature emerges with each additional layer.

The method uses vacuum forming to achieve curved surfaces. In this second method, flat sheets of foam are placed over a negative cavity vacuum mold, a frame is placed over the foam to make an air-tight seal, and the vacuum mold is evacuated. As the vacuum is pulled, heat is applied to the foam, which allows the foam to yield and stretch into the mold cavity. When a new layer is to be added, a multitude of holes are poked through the previously formed foam layers. Adhesive is applied between the layers so that they form a bond across the entire curved surface.

After several layers of foam have been laminated together, the work-piece begins to maintain the curved shape of the mold. By adding or removing layers, the tactile response of the foam layers can be tailored for more lifelike feel.

Once the desired foam layer configuration is completed, the simulated abdominal wall is then inserted into the abdominal wall frame, which is a two-piece system consisting of a top and bottom frame that secures the simulated abdominal wall along the perimeter by compressing the foam layers in an angled channel created by the top and bottom frame components in a friction-fit or compression fit engagement or the like. The design of the frame allows the user to easily install and remove the frame from the surgical simulator enclosure by snapping the perimeter of the frame to the surgical simulator enclosure. The geometry of the abdominal wall frame adds further support to the convex form of the simulated abdominal wall by utilizing an angled channel along the perimeter that the simulated abdominal wall is compressed between. The angled channel of the frame follows the natural shape of the simulated abdominal wall. Simply compressing the simulated abdominal wall between two flat frame pieces results in significantly increased support for the convex form and produces a realistic feel of the simulated abdominal wall and advantageously prevents unwanted inversion of the simulated abdominal wall during normal use.

Figure 4:
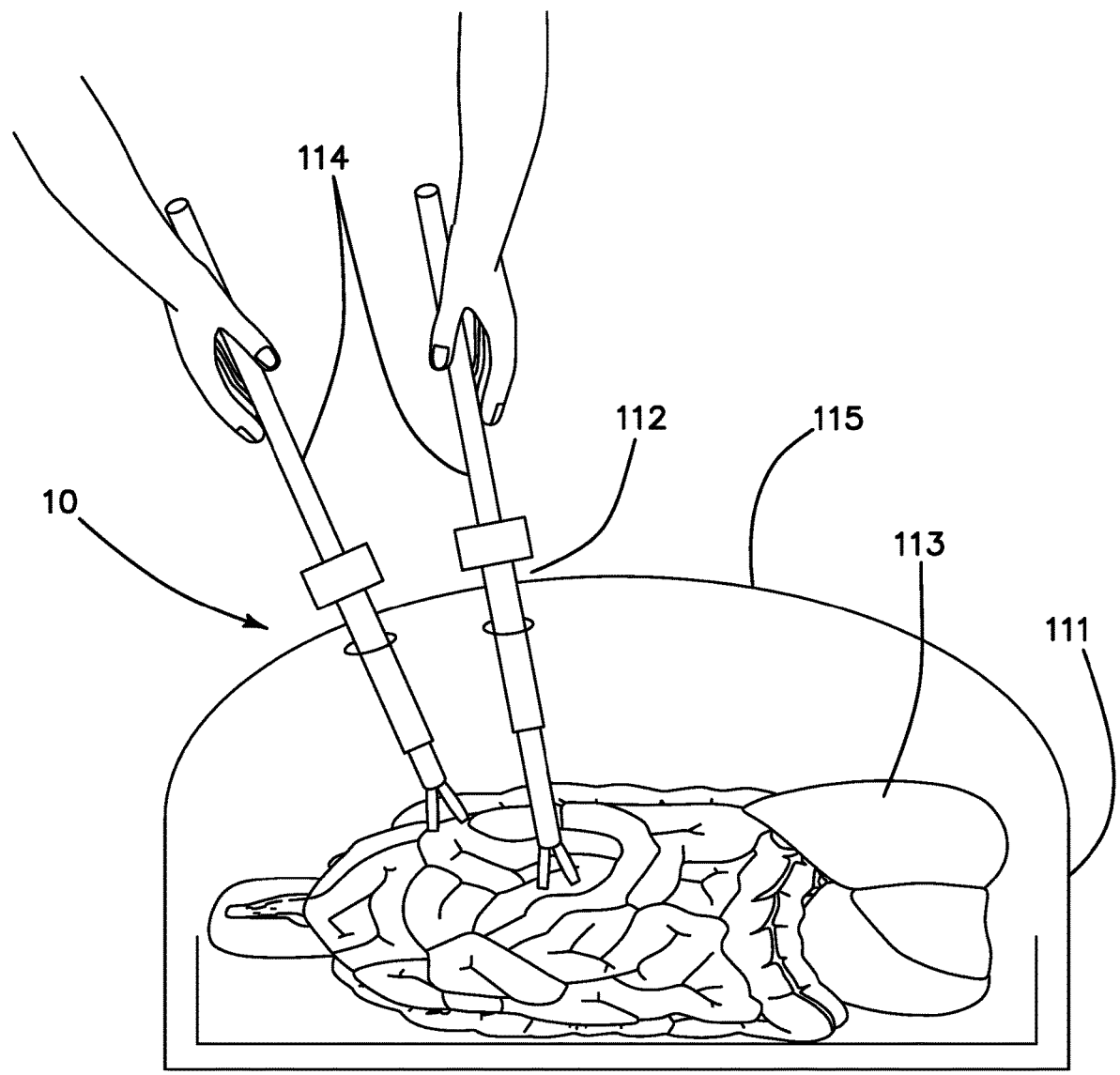
FIG. 4 is a side view of someone performing a simulated procedure in a laparoscopic trainer.

With reference to FIG. 4, a surgical training device also called a trainer or surgical simulator 10 for laparoscopic procedures is shown that allows a trainee to practice intricate surgical maneuvers in an environment that is safe and inexpensive. These simulators 10 generally consist of an enclosure 111 comprising an illuminated environment as described above that can be accessed through surgical access devices commonly referred to as trocars 112. The enclosure is sized and configured to replicate a surgical environment. For instance, the simulator may appear to be an insufflated abdominal cavity and may contain simulated organs 113 capable of being manipulated and "operated on" using real surgical instruments 114, such as but not limited to graspers, dissectors, scissors and even energy-based fusion and cutting devices. Additionally, the enclosure 10 may contain a simulated abdominal wall 115 to improve the realism of the simulation. The simulated abdominal wall 115 facilitates the practice of first entry and trocar 112 placement and advantageously provides a realistic tactile feel for the instruments moving through the simulated abdominal wall.

Figure 5:
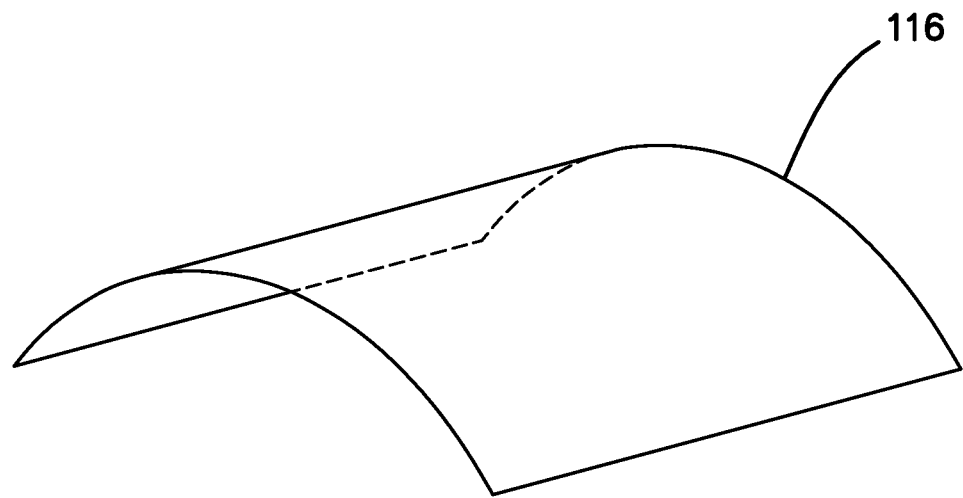
FIG. 5 is a top perspective view of a surface curved in one direction only.
Figure 6:
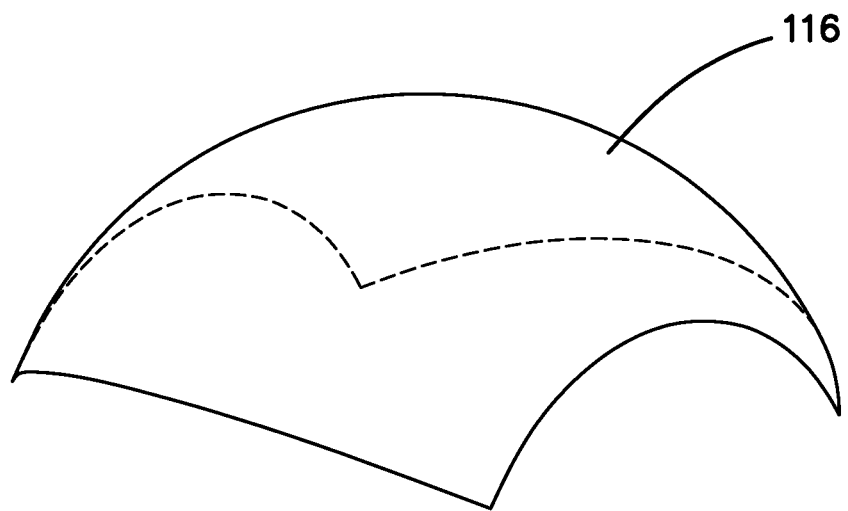
FIG. 6 is a top perspective view of a surface curved in two directions.

Turning to FIG. 5, a surface 116 curved in one direction is shown. Many of the current products on the market make use of a simulated abdominal wall that curves in only one direction as shown in FIG. 5. This shape is an approximation of the real shape of an insufflated abdomen that is curved in several directions. Furthermore, a simulated abdominal wall curved in one direction as shown in FIG. 5 is not as structurally sound as a shape that curves in two directions. Simulated abdominal wall designs that are curved in only one direction often necessitate the use of additional internal support structures beyond a perimeter frame such as crisscrossing reinforcing spine or buttress. FIG. 6 shows a surface 116 that curves in two directions which is more realistic and also more structurally sound than a surface that curves in only one direction. The simulated abdominal wall 14 of the present invention is curved in two directions as shown in FIG. 6.

In view of the foregoing, the present invention aims to eliminate the need for internal support structures while creating a shape that has a visual look and tactile feel that more closely mimic the real abdominal wall.

Figure 7:
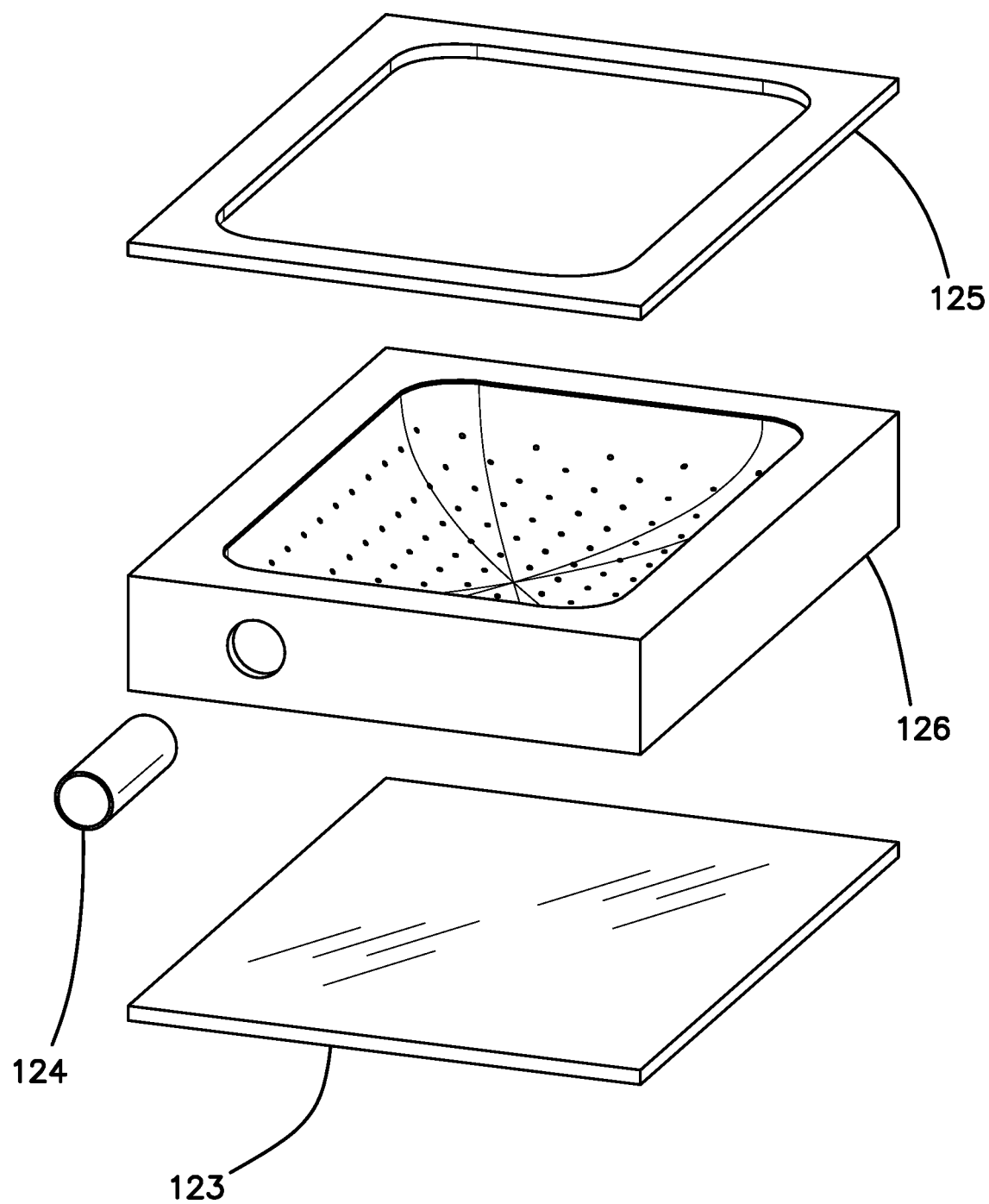
FIG. 7 is a top perspective, exploded view of a negative cavity vacuum mold according to the present invention.
Figure 8:
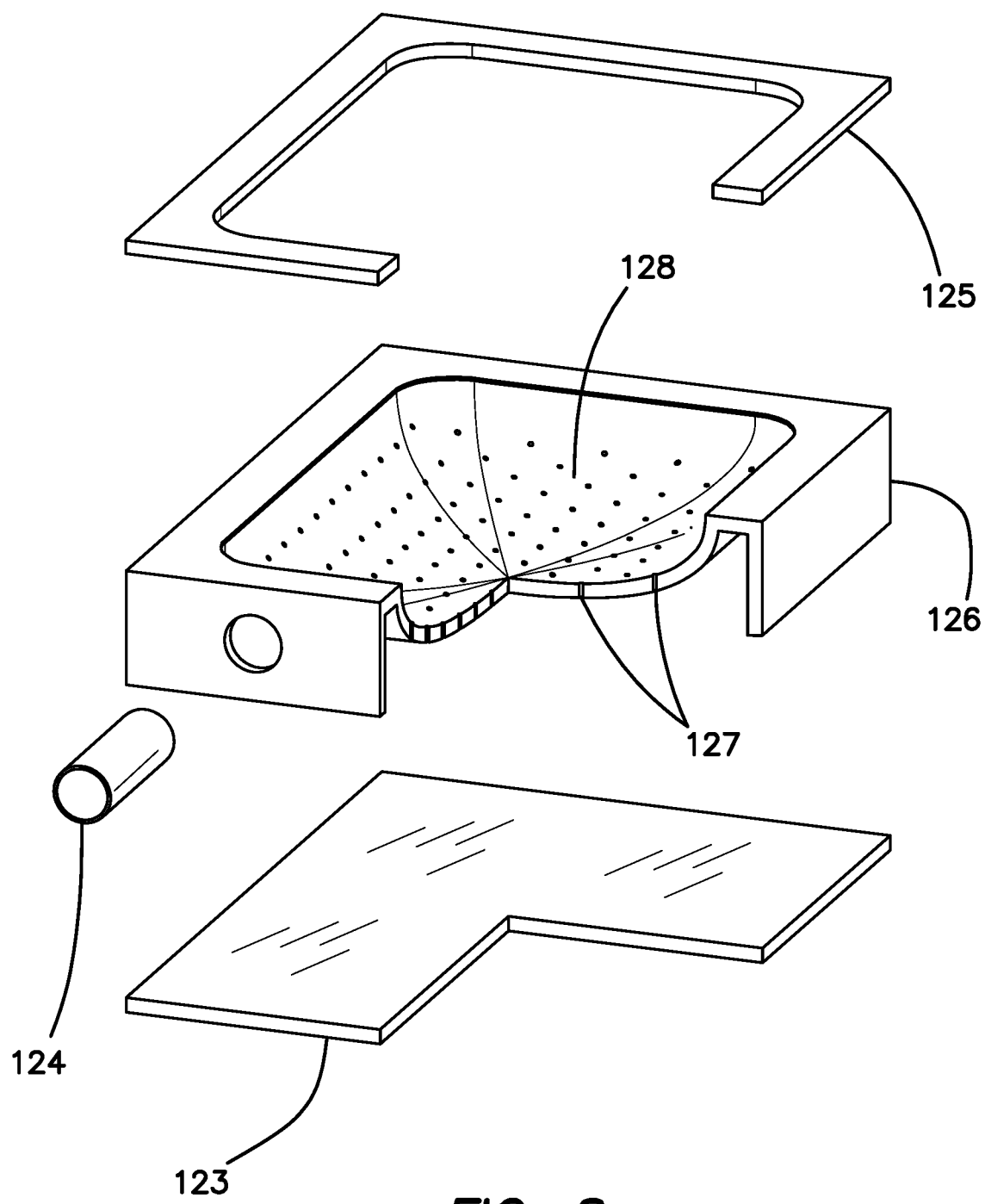
FIG. 8 is a top perspective, exploded section view of a negative cavity vacuum mold according to the present invention.
Figure 9:
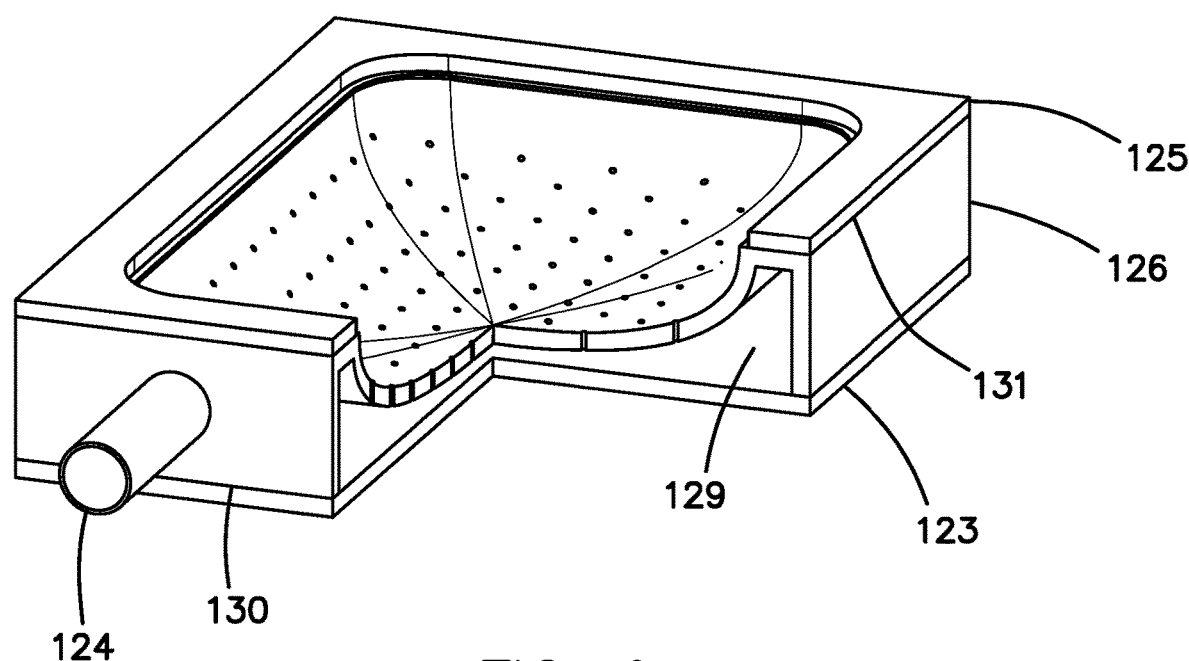
FIG. 9 is a top perspective, section view of a negative cavity vacuum mold according to the present invention.

Turning now to FIG. 7, an exploded view of a negative cavity vacuum mold is shown, consisting of a base 123, air outlet 124, frame 125, and main body 126. FIG. 8 shows an exploded section view of the same vacuum mold. In this view, air-holes 127 are seen to pierce the cavity 128. FIG. 9 shows an assembled section view of the vacuum mold, showing the plenum 129 created between the base 123 and main body 126, the frame seal 130 between the base 123 and main body 126, as well as the plenum seal 131 between the main body 126 and frame 125.

Figure 10:
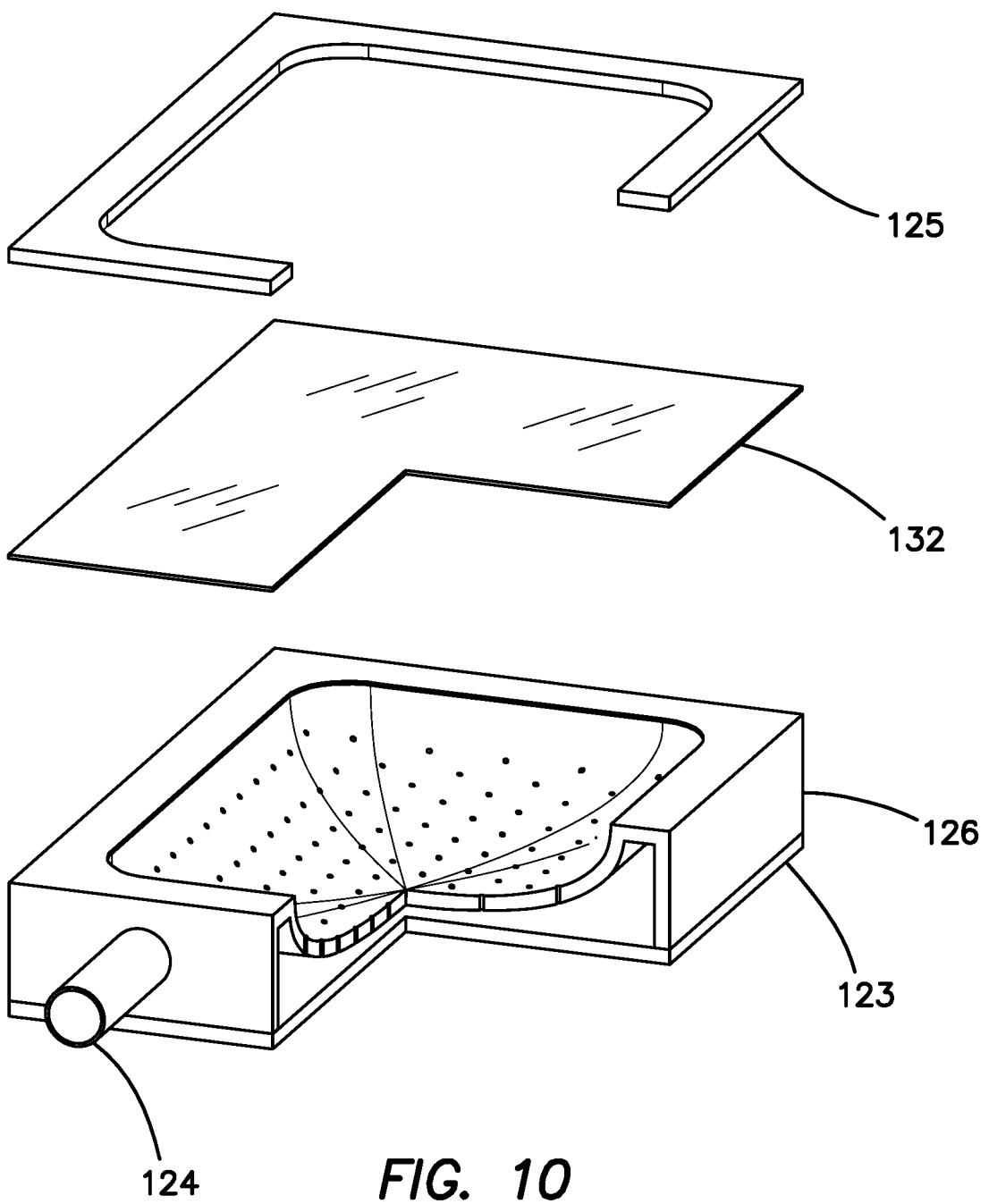
FIG. 10 is a top perspective, exploded section view of a frame, piece of foam and vacuum mold according to the present invention.
Figure 11A:
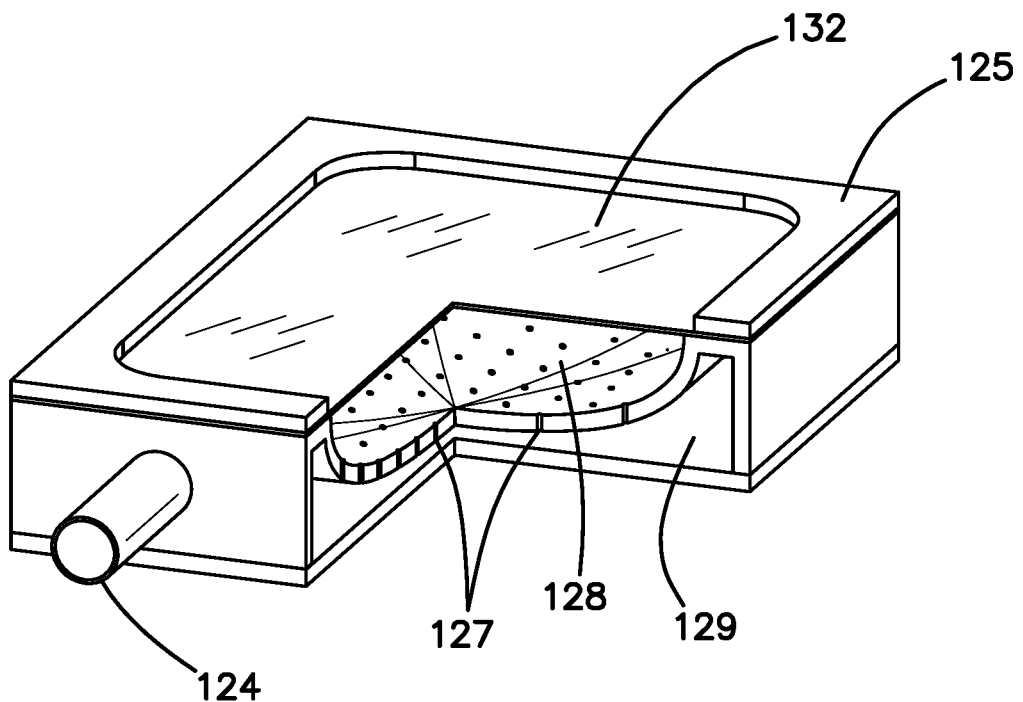
FIG. 11A is a top perspective view of a piece of foam in place on a vacuum mold according to the present invention.
Figure 11B:
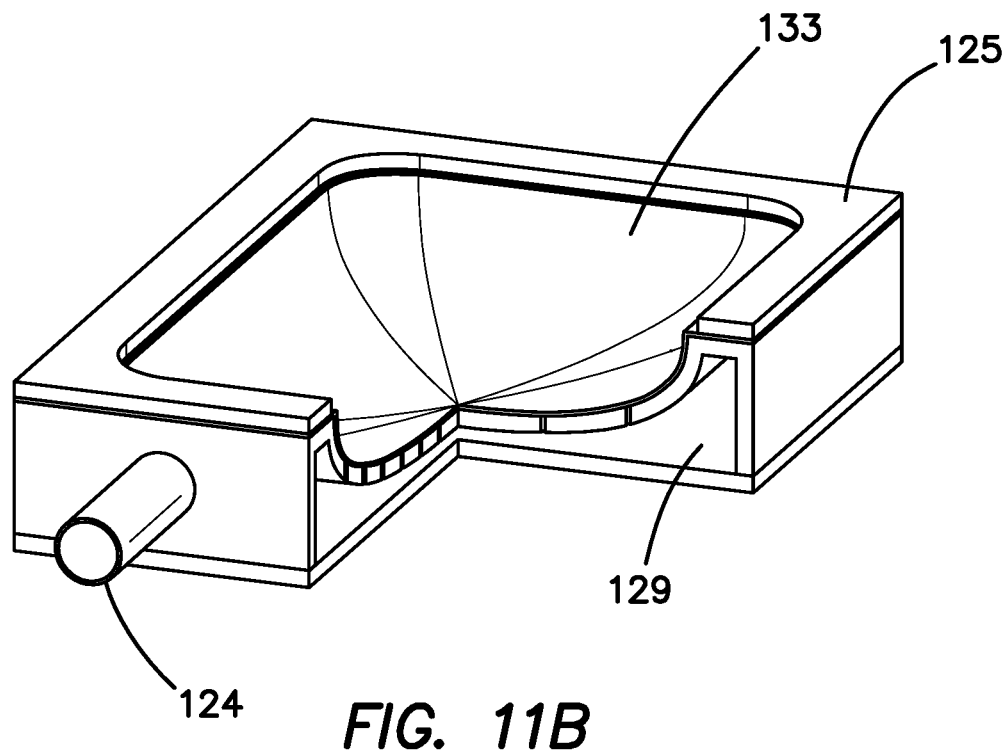
FIG. 11B is a top perspective view of a piece of foam formed on a vacuum mold according to the present invention.

Looking now to FIG. 10, the vacuum mold is shown with a foam sheet 132 ready to be placed on the main body 126, and held in place with frame 125. FIG. 11A shows the flat foam sheet 132 prior to forming located inside the main body and covered by the frame 125. FIG. 11B shows the formed foam sheet 133 after application of vacuum across the plenum. During the forming process, air is evacuated through outlet 124, which creates negative pressure in the plenum 129. This negative pressure acts through air holes 127, and sucks the flat foam sheet 132 towards the inner surface of the cavity 128. While air is being evacuated through outlet 24, heat is applied to the top of the foam, which allows the foam to stretch and make complete contact with the surface of the cavity.

Figure 12:
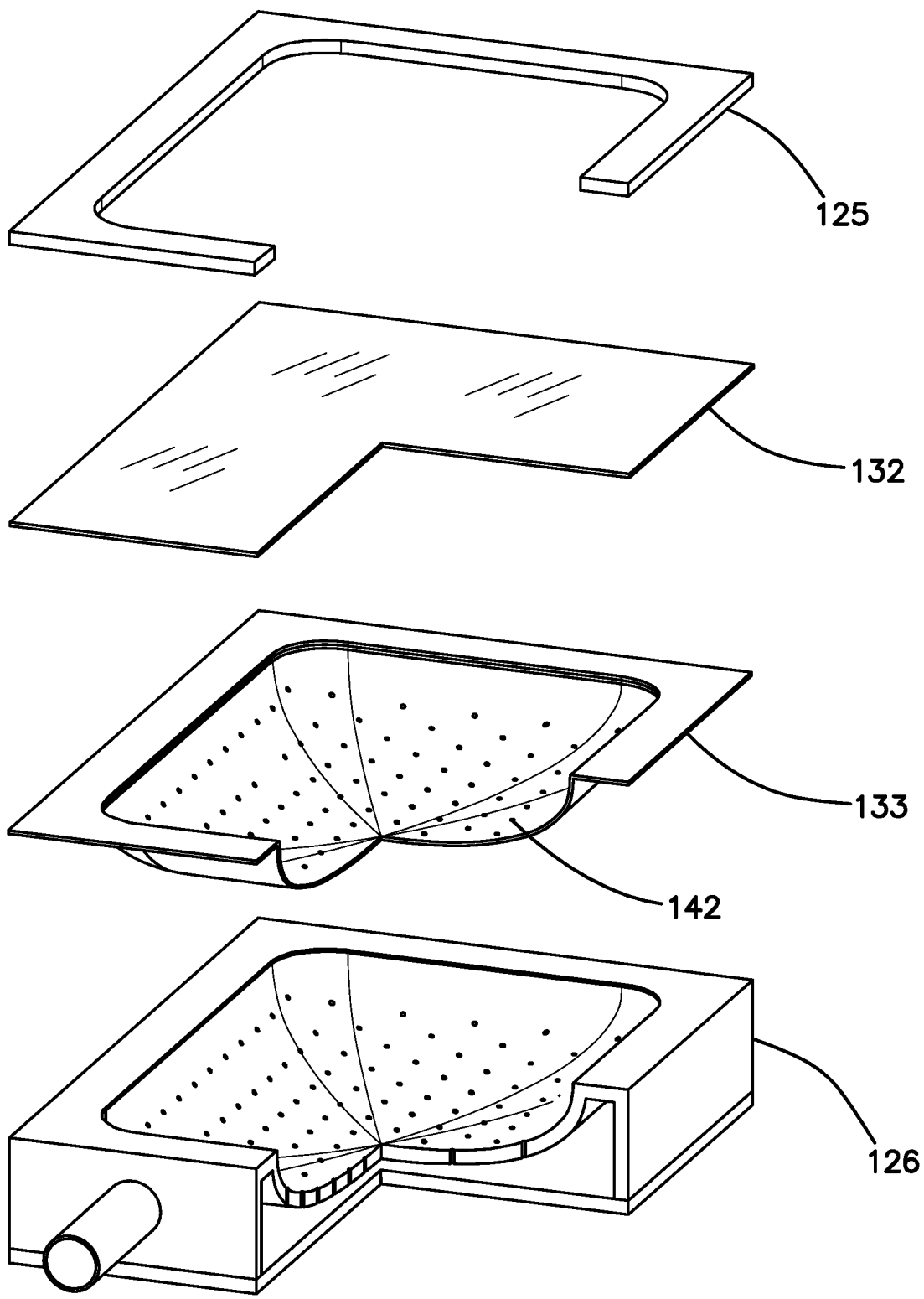
FIG. 12 is a top perspective, exploded section view of a frame, unformed layer, formed layers and vacuum mold according to the present invention.
Figure 13A:
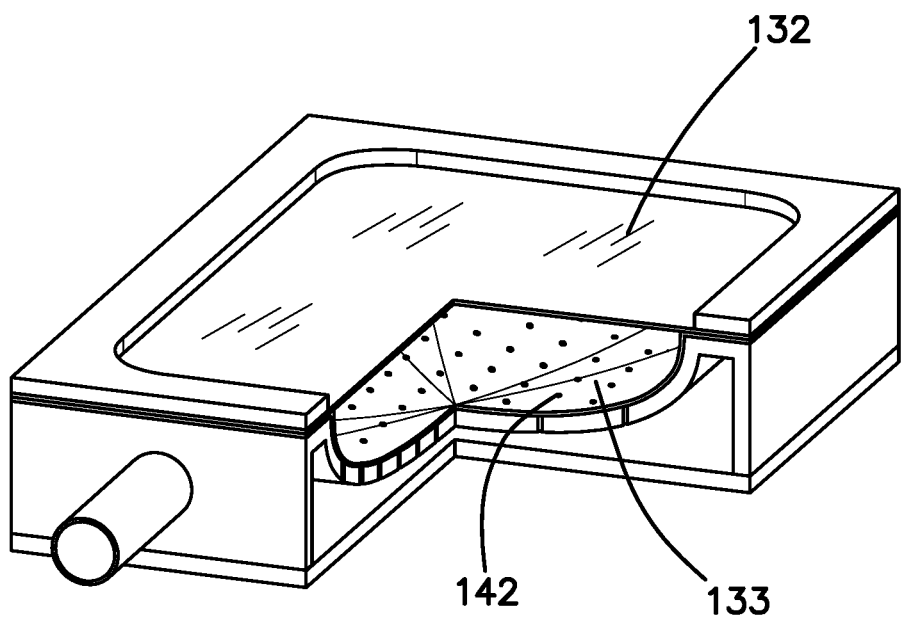
FIG. 13A is a top perspective, section view of a piece of foam in place on a vacuum before forming according to the present invention.
Figure 13B:
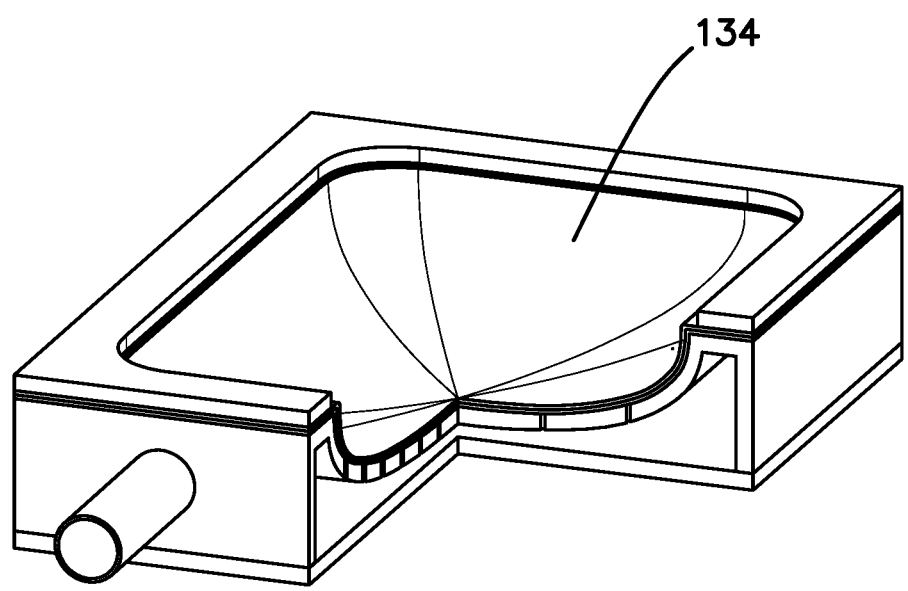
FIG. 13B is a top perspective, section view of layers of foam on a vacuum mold after forming according to the present invention.

FIG. 12 shows an exploded section view of a foam layer 132 being added to the work-piece. Prior to forming in the vacuum mold, a multitude of holes 142 must be poked through the formed foam layer 133 to allow the suction to act through its thickness, thus pulling the flat foam sheet 132 into the cavity. Also prior to placement in the vacuum mold, adhesive must be applied to the top side of the formed foam layer 133, as well as to the underside of the flat foam sheet 132. FIGS. 13A-13B show the flat foam sheet 132 being simultaneously formed and laminated to the formed foam sheet 133, and thus beginning to form the pre-made foam layers 134. Again, different types and colors of foam may be used to simulate the colors and textures present in a real abdominal wall.

Figure 14:
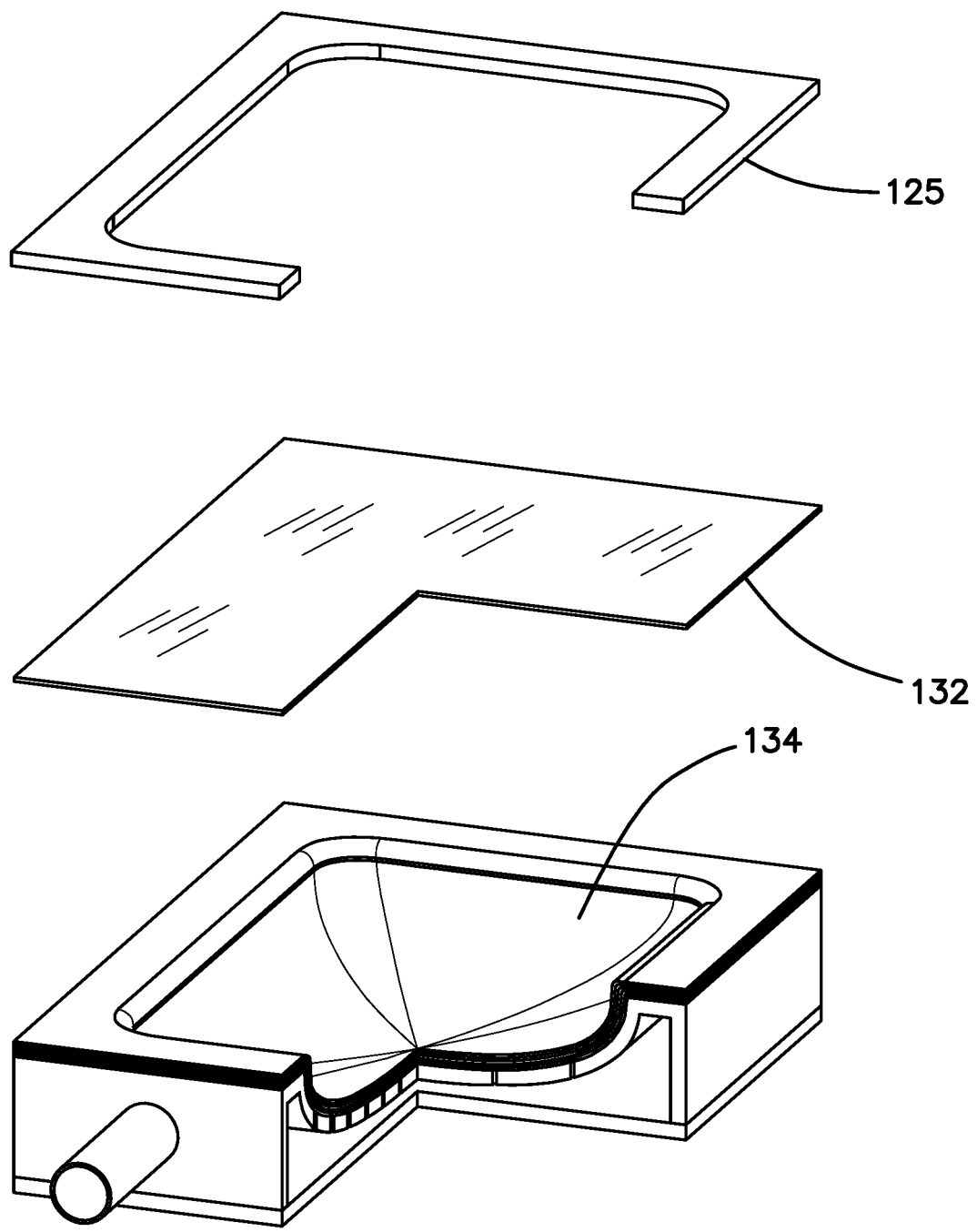
FIG. 14 is a top perspective, exploded section view of a frame, a layer of foam before forming, a plurality of foam layers after forming and a vacuum mold according to the present invention.
Figure 15A:
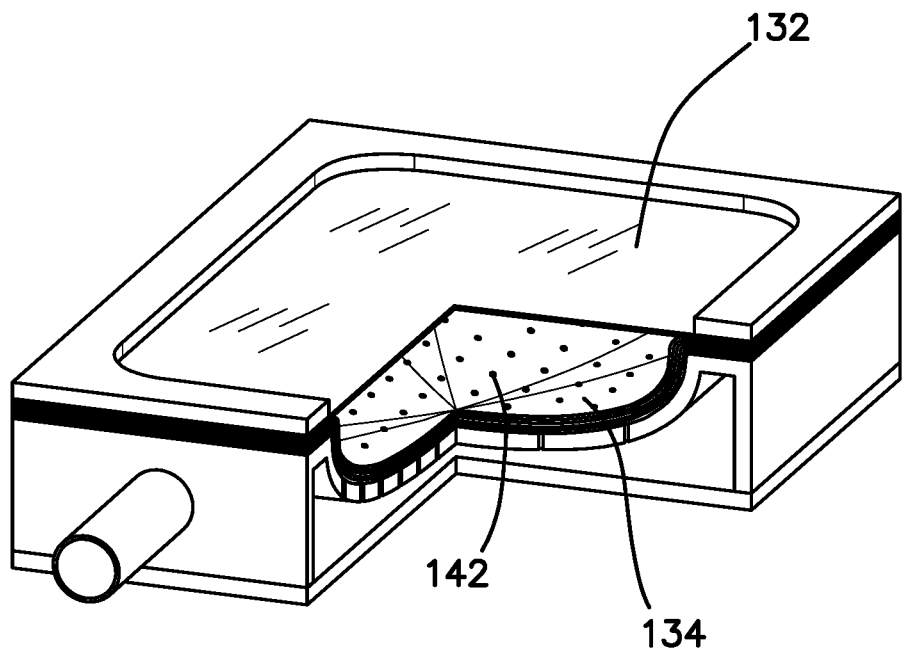
FIG. 15A is a top perspective, section view of a frame, a layer of foam before forming, a plurality of foam layers after forming and a vacuum mold according to the present invention.
Figure 15B:
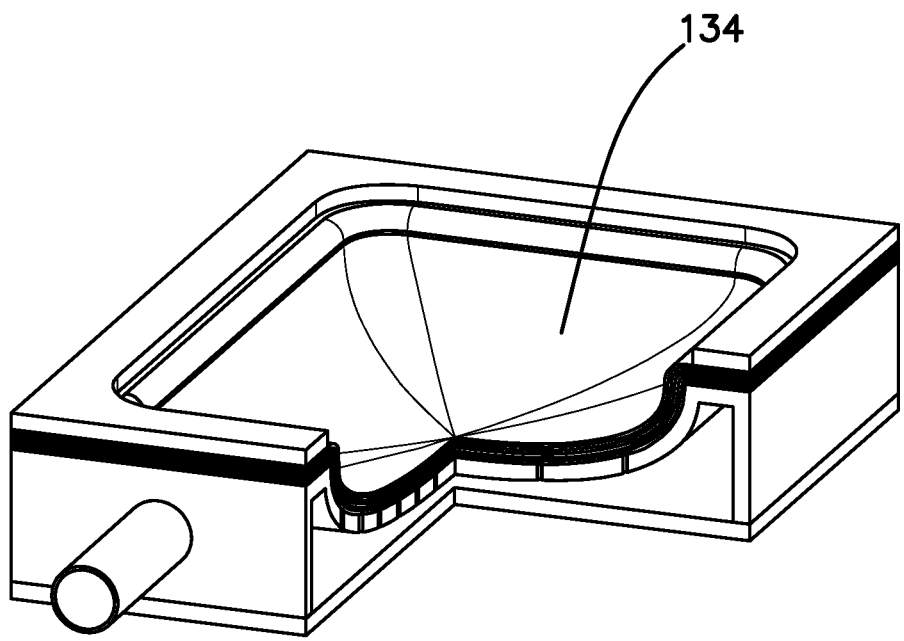
FIG. 15B is a top perspective, section view of a frame and a plurality of foam layers after forming and a vacuum mold according to the present invention.

An exploded view of this process is shown after several repetitions in FIG. 14, where a flat foam sheet 132 will be pressed against a plurality of pre-made foam layers 134 using frame 125. FIG. 15A shows a collapsed view of the aforementioned setup before and, in FIG. 15B, after vacuum forming. Again, between adding layers, it is essential to poke a plurality of small holes 142 through the pre-made foam layers 134, as well as to apply adhesive to the top of the pre-made foam layers 134 and to the underside of the next flat foam layer 132.

Figure 16:
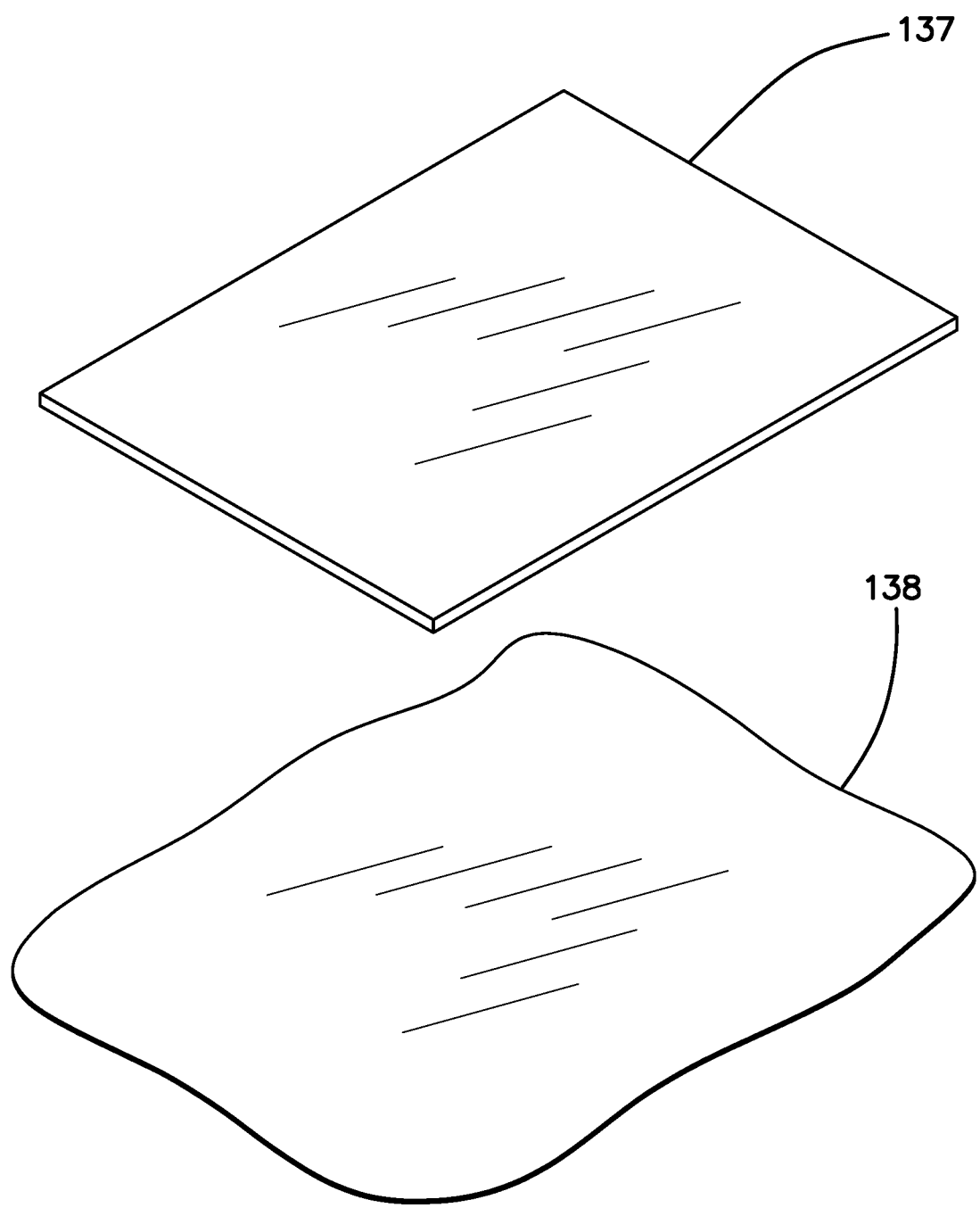
FIG. 16 is a top perspective view of a foam layer and an uncured sheet of silicone to make an artificial skin layer according to the present invention.
Figure 17A:
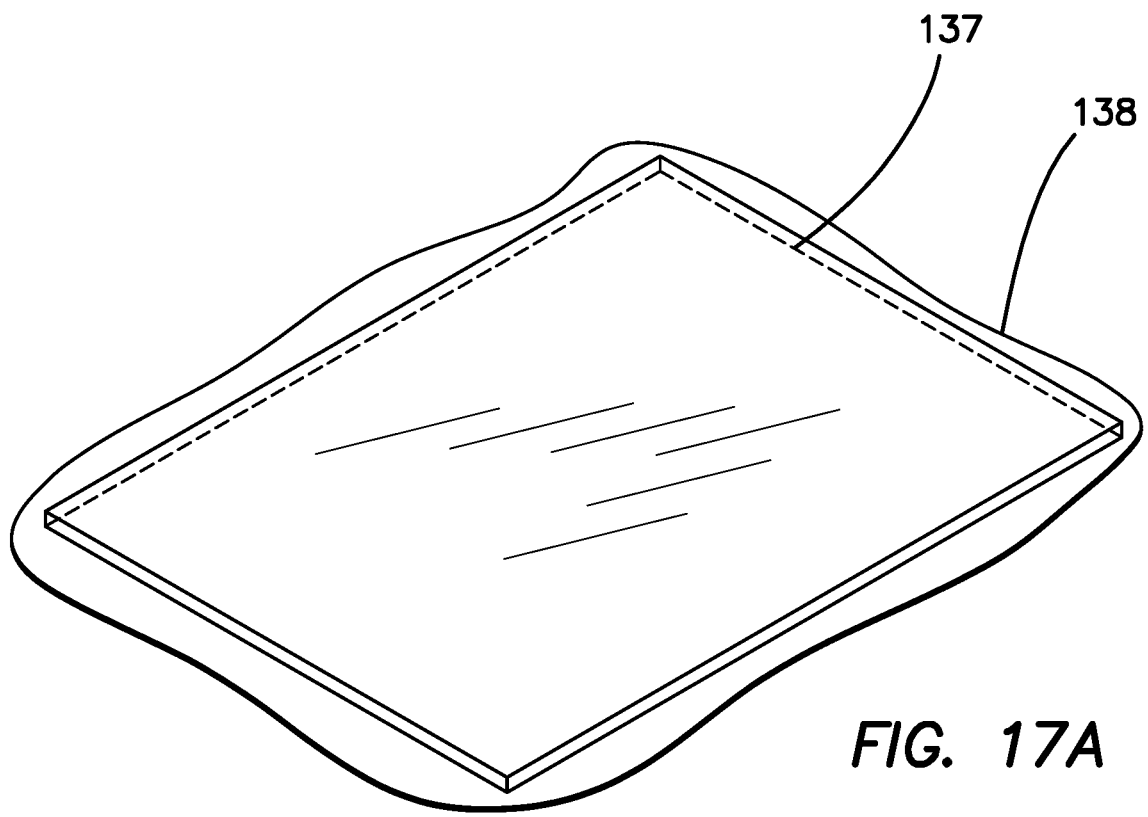
FIG. 17A is a top perspective view of a foam layer in place on a layer of silicone to form an artificial skin layer according to the present invention.
Figure 17B:
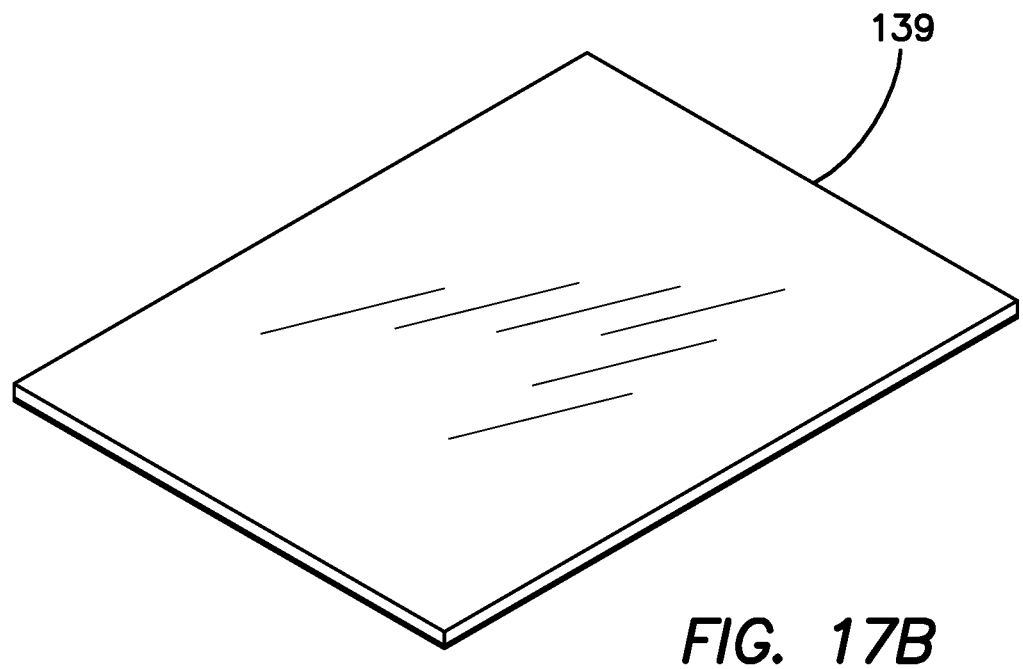
FIG. 17B is a top perspective view of a foam layer adhered to a trimmed layer of silicone forming an artificial skin layer according to the present invention.

Turning now to FIG. 16, an exploded view of the skin layer is observed, showing skin foam layer 137, and uncured silicone layer 138. FIG. 17A shows the skin foam layer 137 in place on the uncured silicone layer 138. When the silicone cures on the foam, it creates a mechanical bond with the slightly porous foam material. Once the silicone is fully cured, the excess is trimmed resulting in the trimmed skin layer 139 shown in FIG. 17B.

Figure 18:
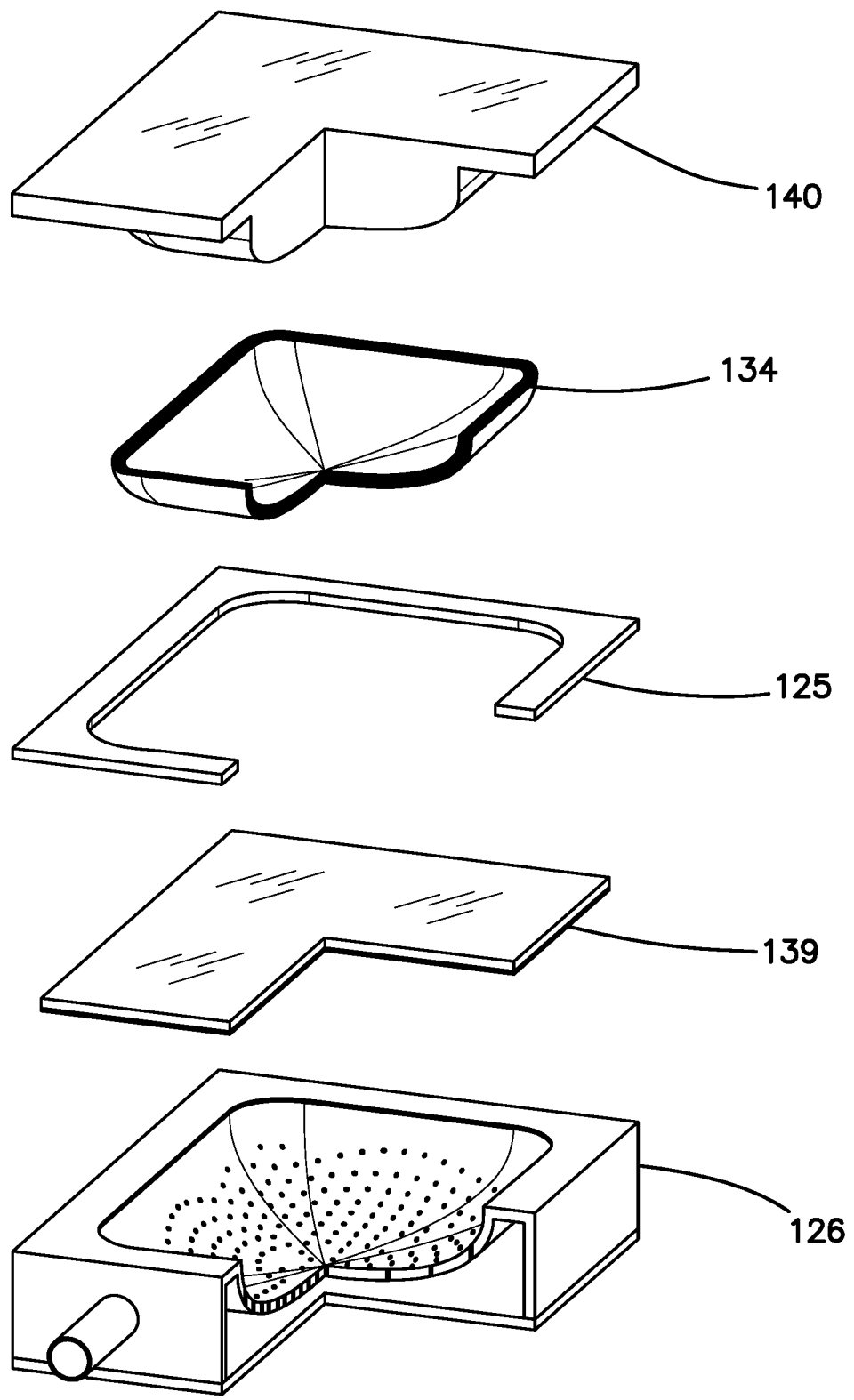
FIG. 18 is a top perspective, exploded section view of a weighted plug, a plurality of adhered foam layers after forming, a frame, a flat artificial skin layer and a the vacuum mold according to the present invention.
Figure 19A:
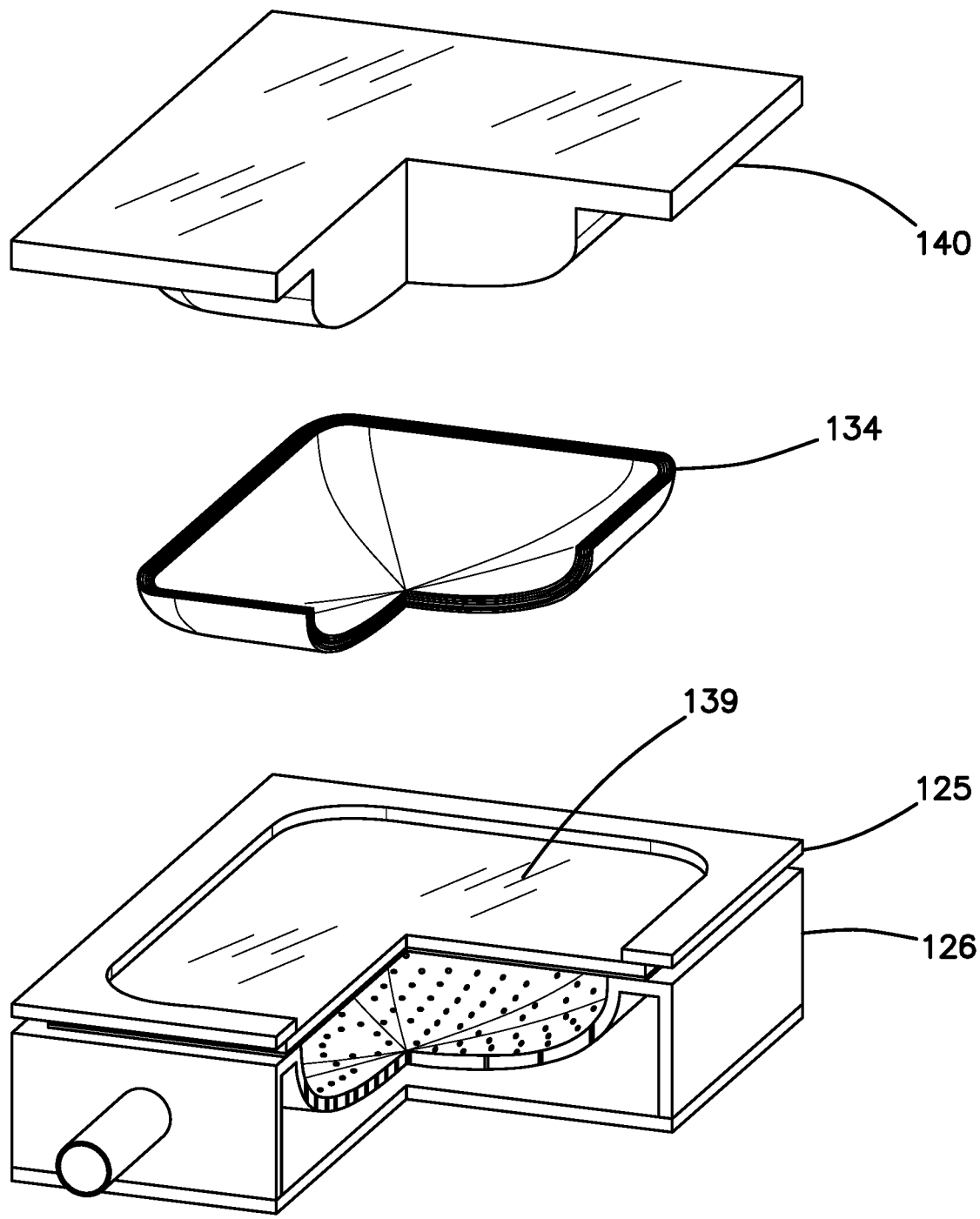
FIG. 19A is a top perspective, exploded section view of a weighted plug, a plurality of adhered foam layers after forming, and a skin layer before forming in place under a frame on a vacuum mold according to the present invention.
Figure 19B:
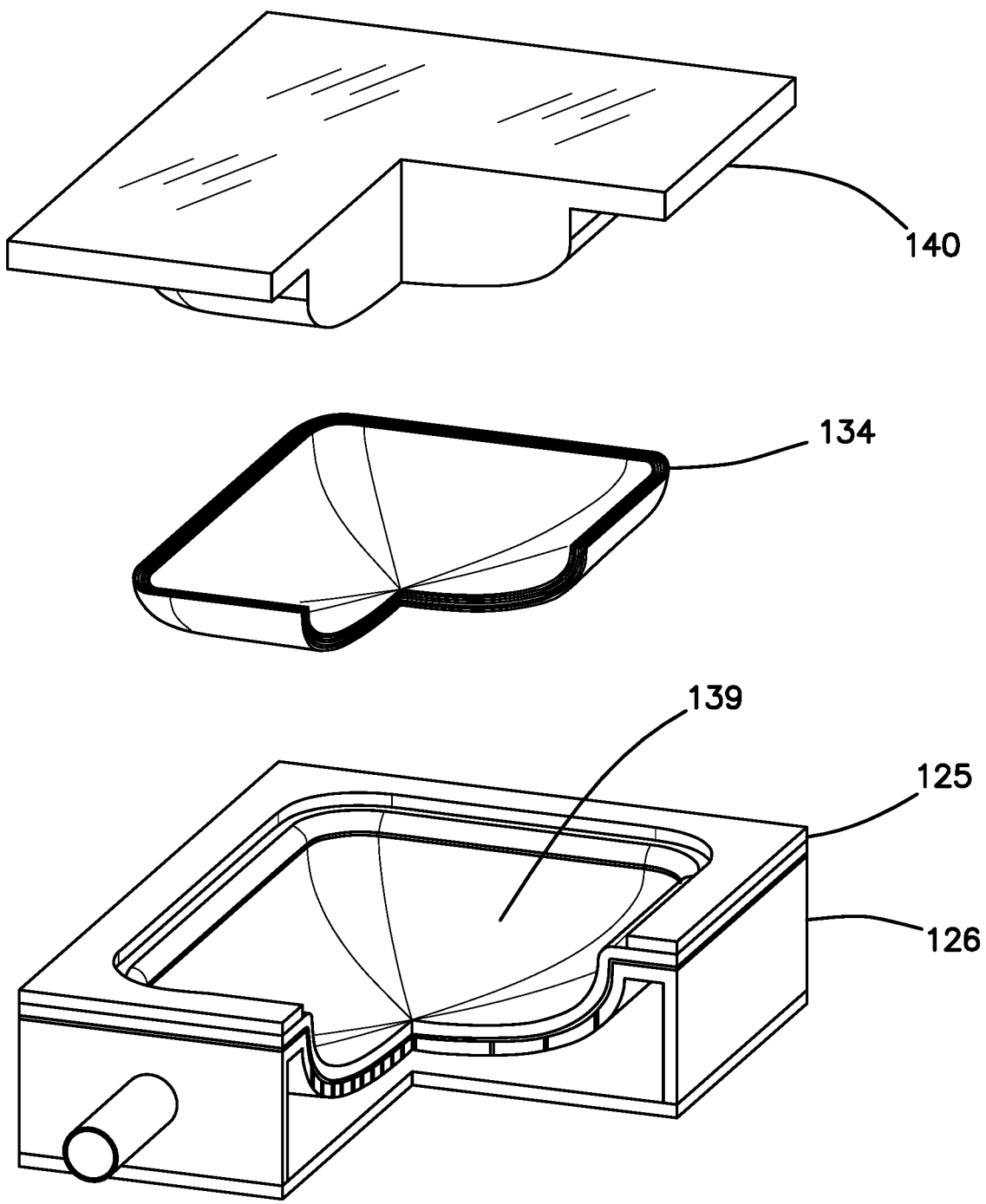
FIG. 19B is a top perspective, exploded section view of a weighted plug, a plurality of adhered foam layers after forming, and a skin layer after forming in place under a frame and on a vacuum mold according to the present invention.
Figure 19C:
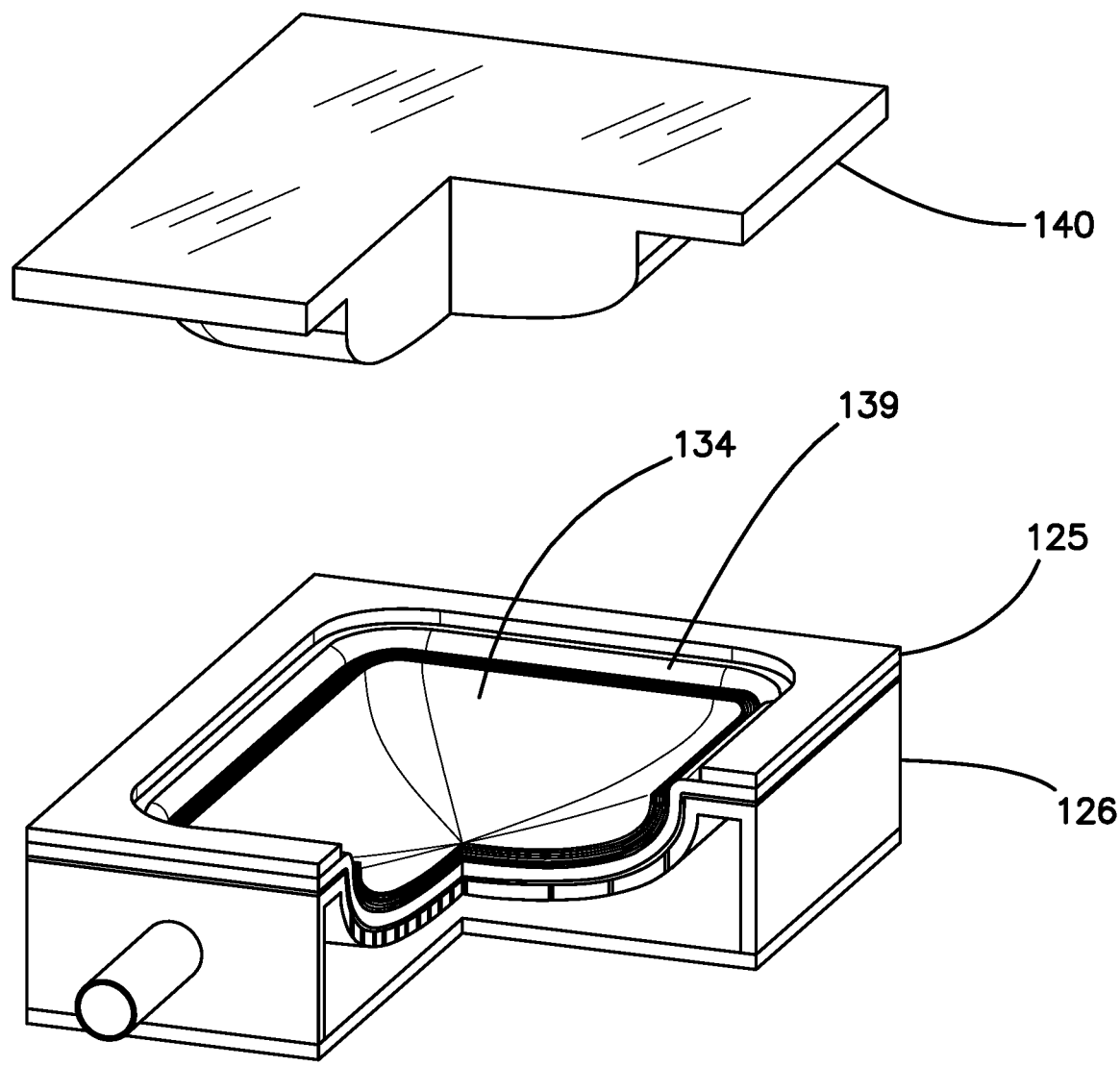
FIG. 19C is a top perspective, exploded section view of a weighted plug, a plurality of adhered foam layers after forming, and a skin layer after forming in place under a frame and on a vacuum mold according to the present invention.
Figure 19D:
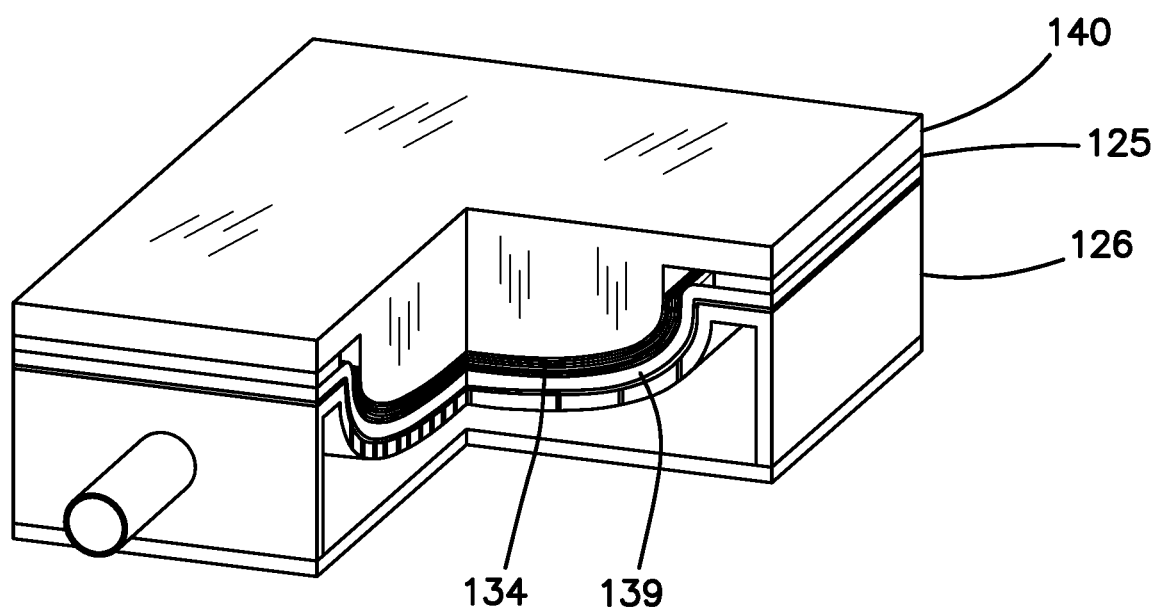
FIG. 19D is a top perspective, section view of a weighted plug, a plurality of adhered foam layers after forming, and a skin layer after forming in place under a frame and on a vacuum mold according to the present invention.

FIG. 18 shows an exploded view of the vacuum mold main body 126, the trimmed skin layer 139 with the silicone side facing the main body 126, the frame 125, the pre-made foam layers 134 and a weighted plug 140 used to press the layers together. FIG. 19A shows the trimmed skin layer 139 held in place on the vacuum mold's main body 126 by the frame 125, prior to evacuation of air in the mold. FIG. 19B shows the trimmed skin layer 139 pulled into the cavity of the vacuum mold, with the pre-made foam layers 134 with or without adhesive applied and ready to be pressed down into the cavity by the weighted plug 140. FIG. 19C shows the pre-made foam inserts 134 placed into the cavity on top of the trimmed skin layer 139. FIG. 19D shows the final step of the process, the placement of the weighted plug 140 on top of the pre-made foam insert 134.

Figure 20A:
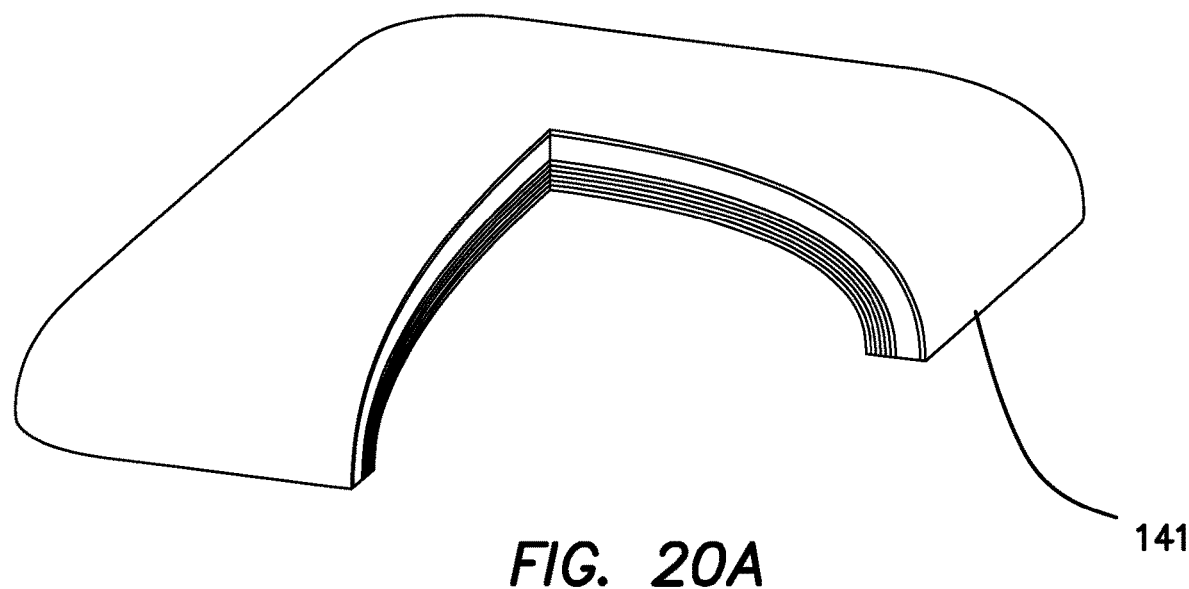
FIG. 20A is a top perspective view of a simulated abdominal wall according to the present invention.
Figure 20B:
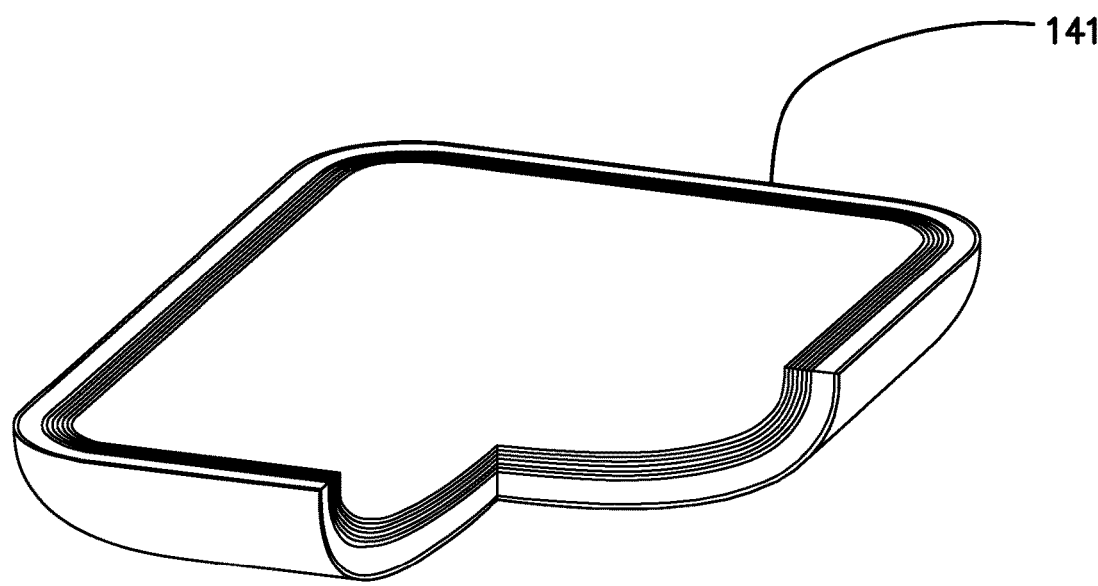
FIG. 20B is a bottom perspective view of a simulated abdominal wall according to the present invention.

FIGS. 20A and 20B show right side up and upside down section views of the final simulated abdominal wall 141 in its finished state, prior to having its edges bound by the simulated abdominal wall frame top and bottom halves 143, 144. The simulated abdominal wall 141 is approximately 12-15 centimeters wide by approximately 15-18 centimeters long and the area of the domed simulated abdominal wall is between approximately 250-280 square inches. The large area permits not only multiple trocar ports to be placed, but also, they can be placed anywhere on the simulated abdominal wall. The simulated abdominal wall is also interchangeable with other simulated abdominal walls including ones configured for obese and pediatric patients. Furthermore, the large simulated abdominal wall is not limited to practicing laparoscopic, minimally invasive procedures, but also, advantageously permits open procedures to be performed through the simulated abdominal wall.

Figure 21:
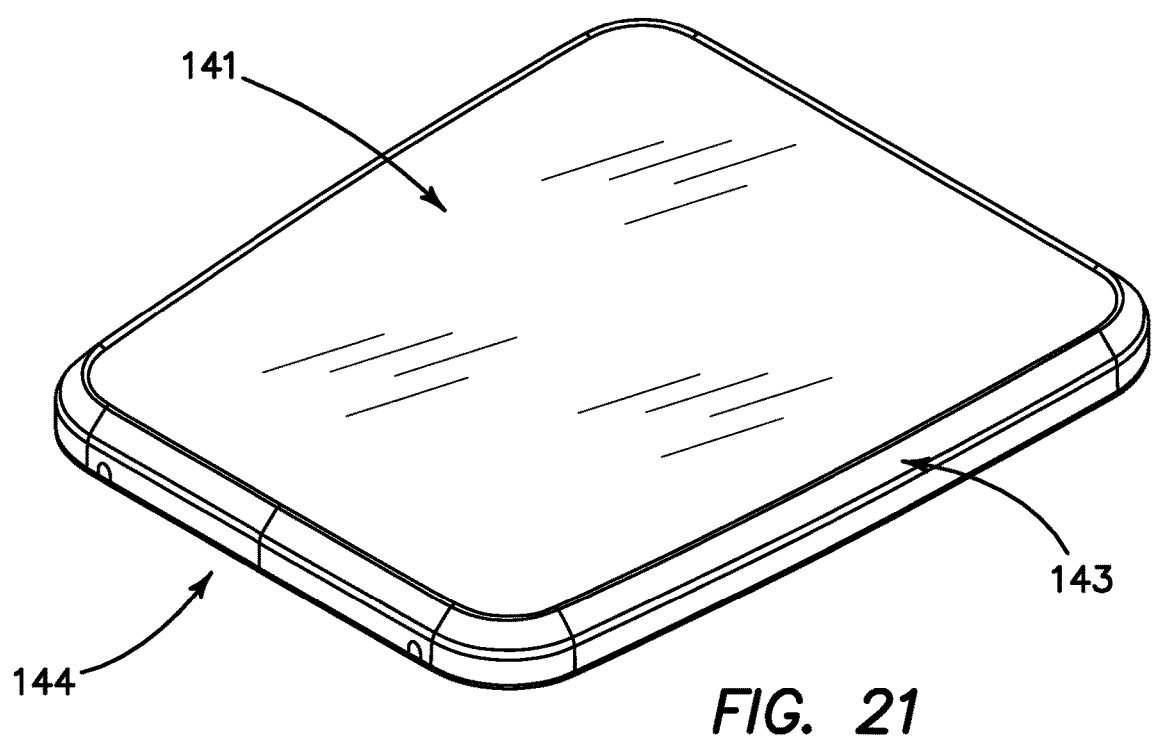
FIG. 21 is a top perspective view of a simulated abdominal wall and frame according to the present invention.
Figure 22:
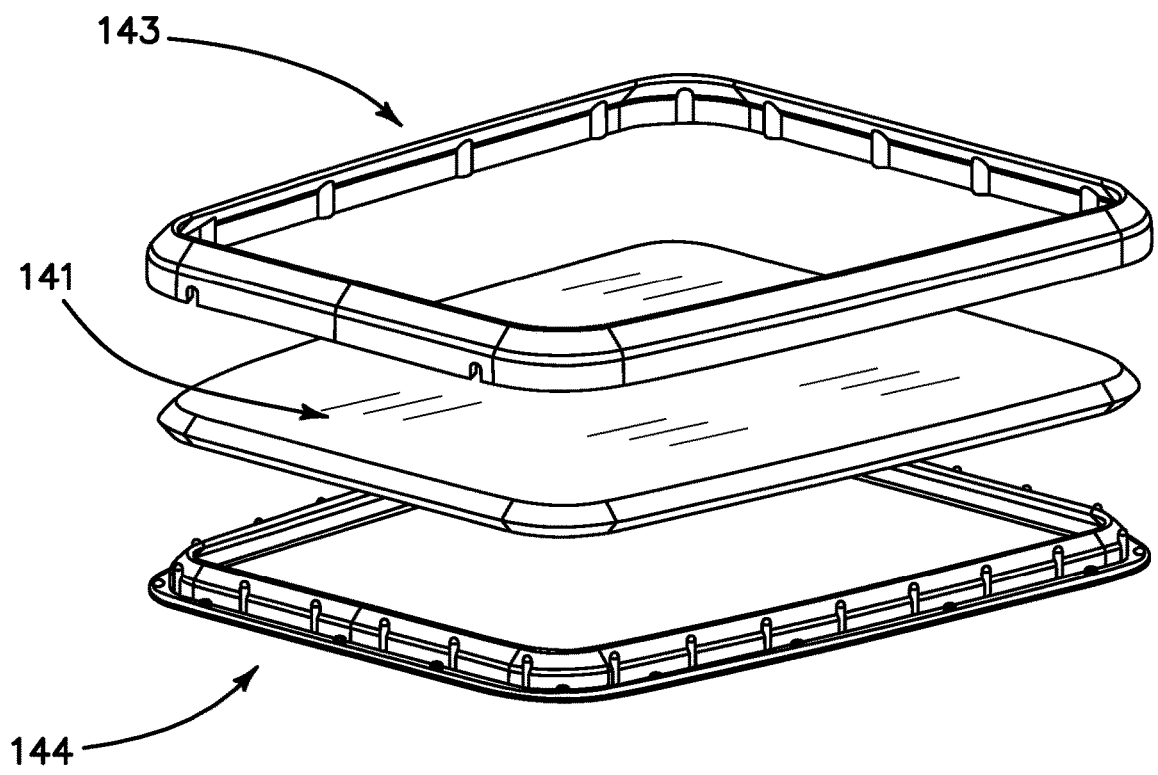
FIG. 22 is a top perspective, exploded view of a simulated abdominal wall between two frame halves according to the present invention.

FIG. 21 shows the simulated abdominal wall 141 set into the simulated abdominal wall frame 143, 144. This unit is then fixed into a laparoscopic trainer. FIG. 22 shows the exploded view of the simulated abdominal wall 141 and frame assembly which includes a top frame 143, and a bottom frame 144. The top frame 143 and bottom frame 144 can be assembled together via screws in the case of a re-usable frame system, or snapped together via heat staking or other low-cost assembly method.

Figure 23:
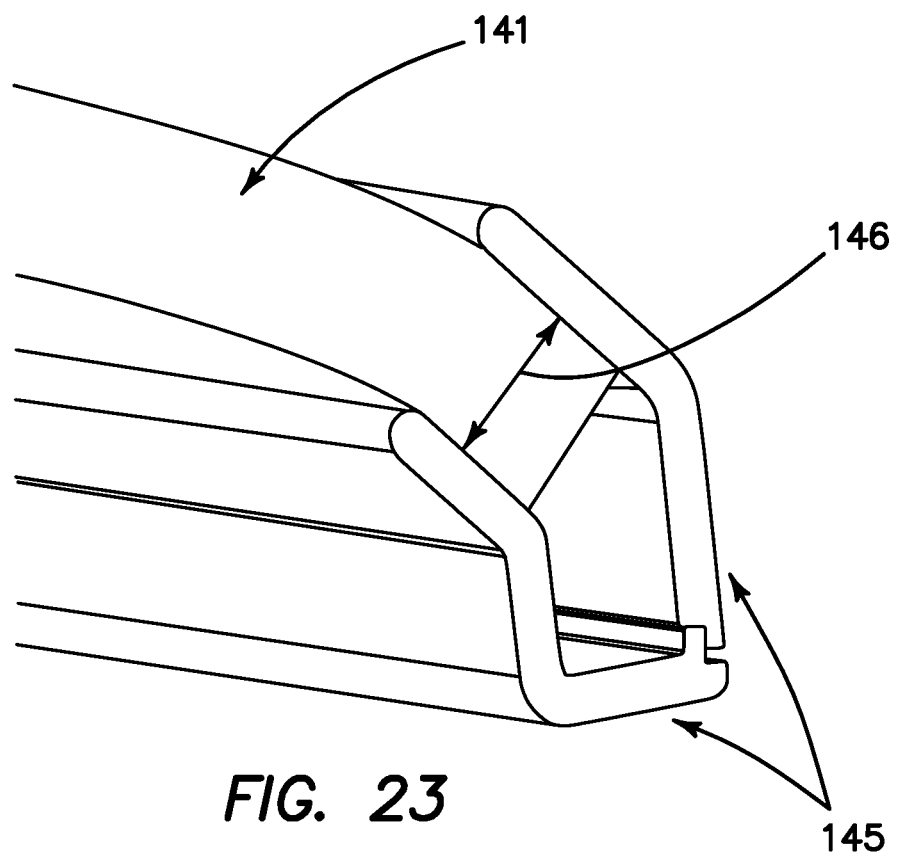
FIG. 23 is a perspective, section view of a simulated abdominal and two frame halves showing an angled channel.

With reference to FIG. 23, one of the key features in the simulated abdominal wall frame 145 is the angled channel 146 in which the simulated abdominal wall 141 is compressed. The angle of the channel 146 follows the contour of the simulated abdominal wall 141 and significantly increases the support and form of the convex simulated abdominal wall 141. In contrast, a simulated abdominal wall 141 that is compressed and retained between two flat frames is relatively weaker and more likely to invert/collapse during use.

Figure 24A:
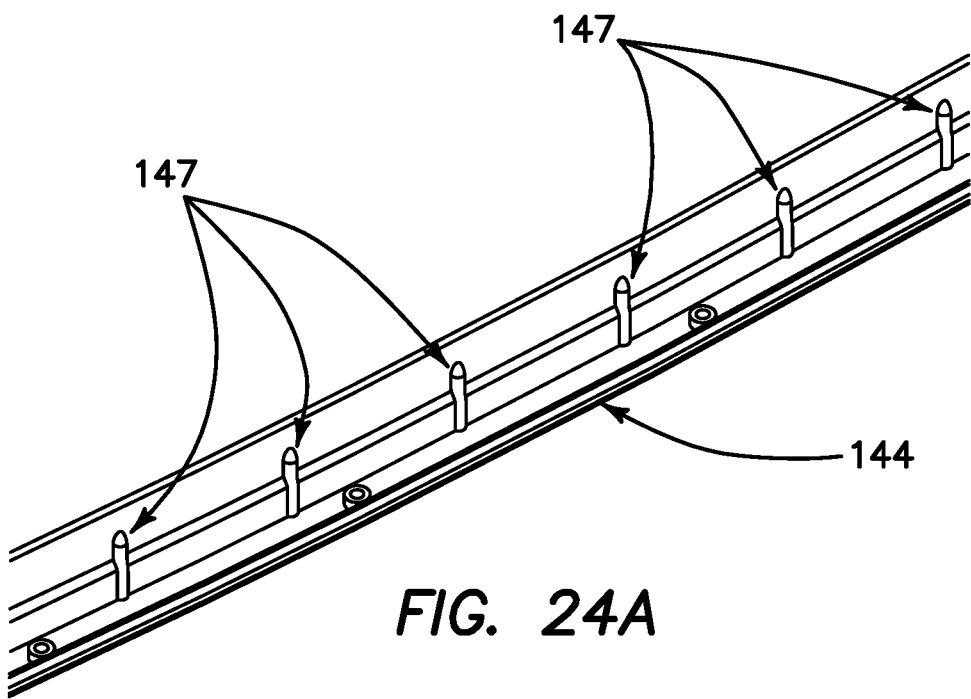
FIG. 24A is a top perspective, section view of a bottom frame half showing retention protrusions according to the present invention.
Figure 24B:
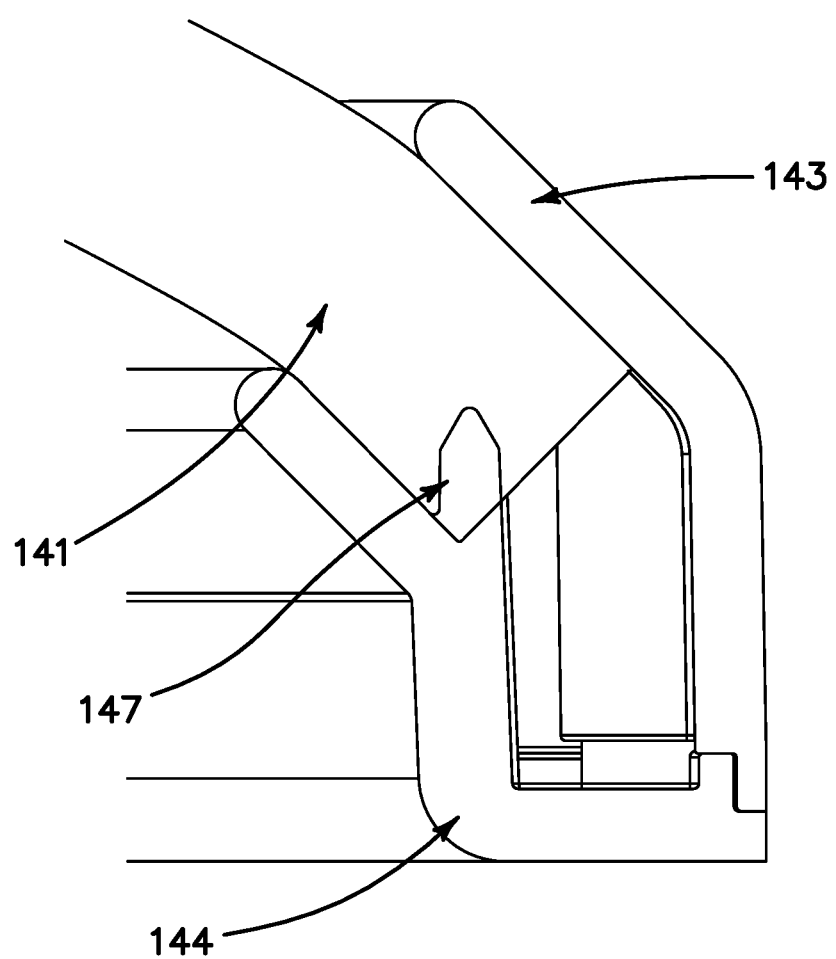
FIG. 24B is a cross-sectional view of a simulated abdominal wall and frame according to the present invention.

FIG. 24A shows the protrusions 147 that are spaced around the perimeter of the bottom frame 144. These retaining protrusions 147 can also be present on the top frame 143, or both frame halves 143, 144. These retaining protrusions 147 provide additional retention of the simulated abdominal wall 141 within the simulated abdominal wall frame 145 by pressing or biting into the simulated abdominal wall as it is compressed between the frame top 143 and frame bottom 144. With reference to FIG. 24B, a simulated abdominal wall 141 is compressed between the two frame halves 143, 144 and is pierced by a retaining protrusion 147.

It should be noted that although one method is described here for layering pre-made foam sheets in order to create a curved surface with structural integrity, other methods are also within the scope of the present invention, including a casting mold that allows the user to sequentially build up a multitude of curved layers that are adhered to one another across their entire surface.

After the surgical training device 10 is assembled with the simulated abdominal instrument in place atop the trainer, laparoscopic or endoscopic instruments are used to perform mock surgeries using the surgical training device 10 of the present invention. Generally, artificial tissue structures and organs sized and configured to represent actual anatomical features, skill-specific models or one or more skill practice stations are placed inside the trainer 10. Surgical simulators, such as the surgical training device 10 of the present invention, are especially useful when they include feedback for the user. In the mock procedure, the performance of the user is monitored, recorded and interpreted in the form of user feedback through integration of various sensing technologies into the simulated environment. The present invention provides low-cost sensorized instruments that are capable of monitoring the motion and force applied by a user to the simulated tissue and the like located inside the trainer cavity. The sensorized instruments are connected to a microprocessor, memory and video display and configured to receive data from various sensors including but not limited to sensors located on the surgical instruments, analyze the data and provide appropriate feedback to assist in teaching and training the user. The present invention can be employed with multiple surgical instruments and accessories, including but not limited to graspers, dissectors, scissors, and needle drivers. Data gathered from a mock surgery can be used to compare a trainee's performance to that of an experienced surgeon or that of other trainees to provide appropriate feedback. Such a system may improve the rate of skill acquisition of trainees and, as a result, improve surgical outcomes, and skills.

The present invention utilizes a number of sensing systems making use of a variety of fundamental sensing principles and technologies such as strain gauges. For example, a strain gauge commonly consists of a metallic foil pattern supported by a flexible backing. When applied properly to a structure of interest, stresses and strains experienced by the structure are transferred to the strain gauge as tension, compression or torsion on the metallic foil pattern. These mechanical stimuli alter the geometry of the foil pattern and, as a result, cause a change in the electrical resistance of the foil pattern, which can be measured. An additional aspect that is important to the use of strain gauges is the configuration in which they are utilized. Strain gauges are typically wired into an electrical circuit, commonly known as the Wheatstone bridge, which consists of two parallel voltage dividers. In this configuration, the difference between the electric nodes at the center of the voltage dividers of the circuit is amplified and measured. The configuration in which the strain gauges are both wired into the circuit and applied to an object of interest determines what loads the sensor system actually measures. For example, to measure axial strain, two strain gauges are aligned on opposite sides of a component and are also wired on opposite sides of the bridge circuit such that they do not share a node.

Figure 25:
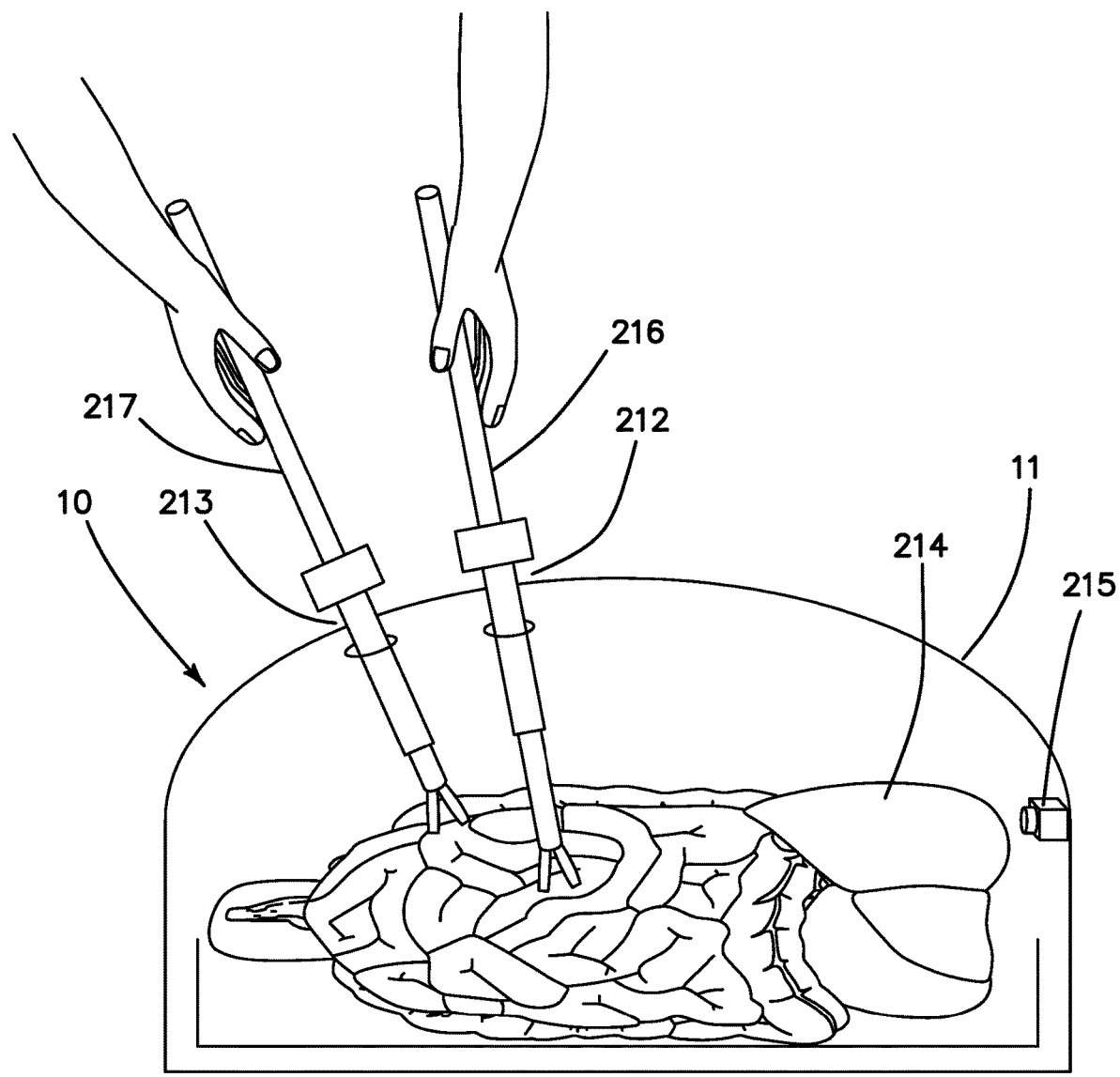
FIG. 25 is a side elevational view of a typical laparoscopic surgical procedure performed in a simulator according to the present invention.

Turning now to FIG. 25, surgical simulators 10 for laparoscopic procedures have been developed that allow a trainee to practice intricate surgical maneuvers in an environment that is safe and inexpensive. These simulators generally consist of a cavity 12 comprising an illuminated environment that can be accessed through surgical access devices commonly referred to as trocars 212 and 213. The enclosure is sized and configured to replicate a surgical environment, such as an insufflated abdominal cavity containing simulated organs 214 that are capable of being manipulated and "operated on" using real surgical instruments 216 and 217, such as but not limited to graspers, dissectors, scissors and even energy-based fusion and cutting devices. Laparoscopes/endoscopes or other cameras 215 are inserted into the cavity through the simulated abdominal wall. More advanced simulators may also make use of various sensors to record the user's performance and provide feedback. These advanced systems may record a variety of parameters, herein referred to as metrics, including but not limited to motion path length, smoothness of motion, economy of movement, force, etc.

In view of the forgoing, the present invention aims to monitor force applied by a trainee, interpret the collected information and use it to improve user performance through feedback and appropriate teaching. The present invention itself focuses on the methods for monitoring and collecting force applied by the user.

In reference to FIGS. 26A, 26B, and 26C, a variety of laparoscopic instruments are shown including a grasper 218, a dissector 219 and scissors 220, respectively. These devices, although different in function, generally share certain key features. Each instrument includes a handle 221 which controls the operable distal end of the instrument. Actuation of the handle opens and closes the jaw-like tip to perform grasping, dissecting or cutting based on the type of instrument used. Additionally, the instrument is configured to permit rotation of the shaft 227 by way of an adjustable component 222 in reach of the user's fingers. A locking mechanism 223 is also provided at the handle to allow the surgeon/trainee to maintain the jaws of the instrument at a given position.

Figure 27:
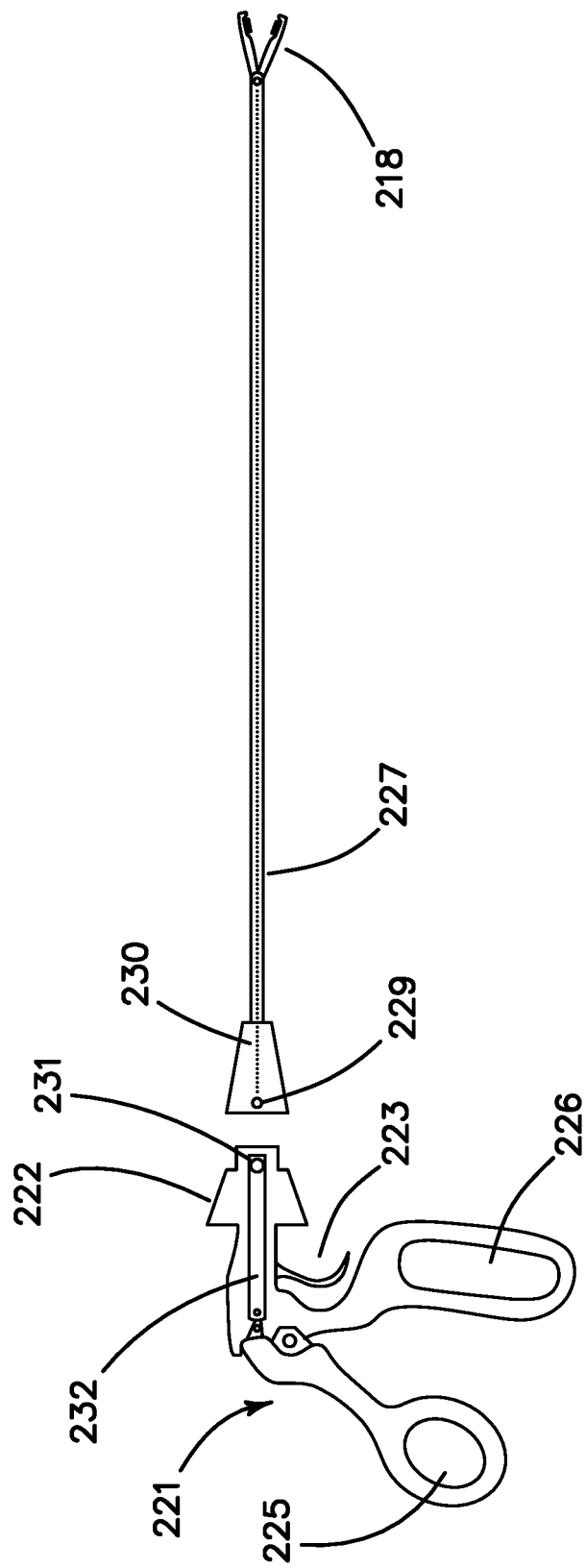
FIG. 27 is a side elevational view of a laparoscopic dissector instrument shaft detached from a handle according to the present invention.

With further reference to FIG. 27, the present invention makes use of a scissor type handle 221 that can be reused after each surgical procedure. The handle 221 is designed such that a variety of disposable shafts 227, each with a different tip element 218-220, can be fixed to the same handle 221. In the present system, the disposable shafts 227 have a ball end 229 connected to a rod 230 which articulates with the instrument's tips 218. This piece fits into a spherical slot 231 at the end of a movement arm 232 inside of the handle 221 that connects to the grips 225 and 226. Movement of the thumb grip 225 actuates the rod 232 which opens or closes the instrument tips 218. The ability of such a system to swap out shafts 227 advantageously permits a single handle 221 to house the necessary electronics while being interchangeable with a variety of different instrument shafts and tips.

Figure 28:
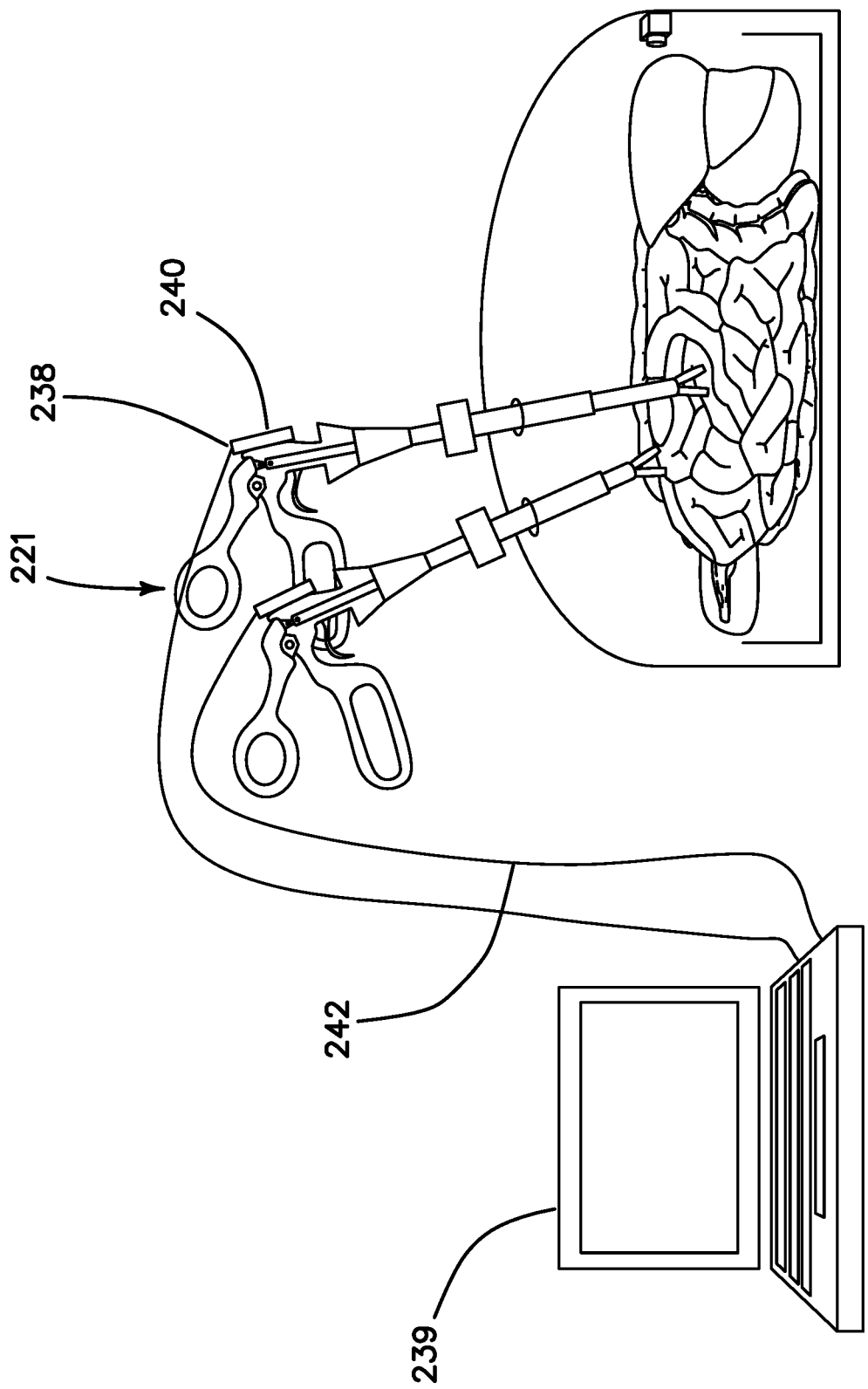
FIG. 28 is a schematic of a laparoscopic trainer containing artificial organs and two laparoscopic surgical instruments connected to an external microprocessor during use according to the present invention.

As shown in FIG. 28, the electronics such as the circuit board and sensors for force sensing are enclosed in a housing 240 and connected to the handle 221 of the instrument. The electronics are electronically connected via a USB cord 238, 242 to an external computer 239. The following descriptions reference a reposable system 221. Previously the instruments with sensors located on the shaft were disposable and very difficult to sterilize if needed. However, with the sensors on the handle, the shaft assembly can be interchanged and discarded as needed. The reposable handle 221 is modified to incorporate housing 240 for a custom circuit board 241.

Figure 29:
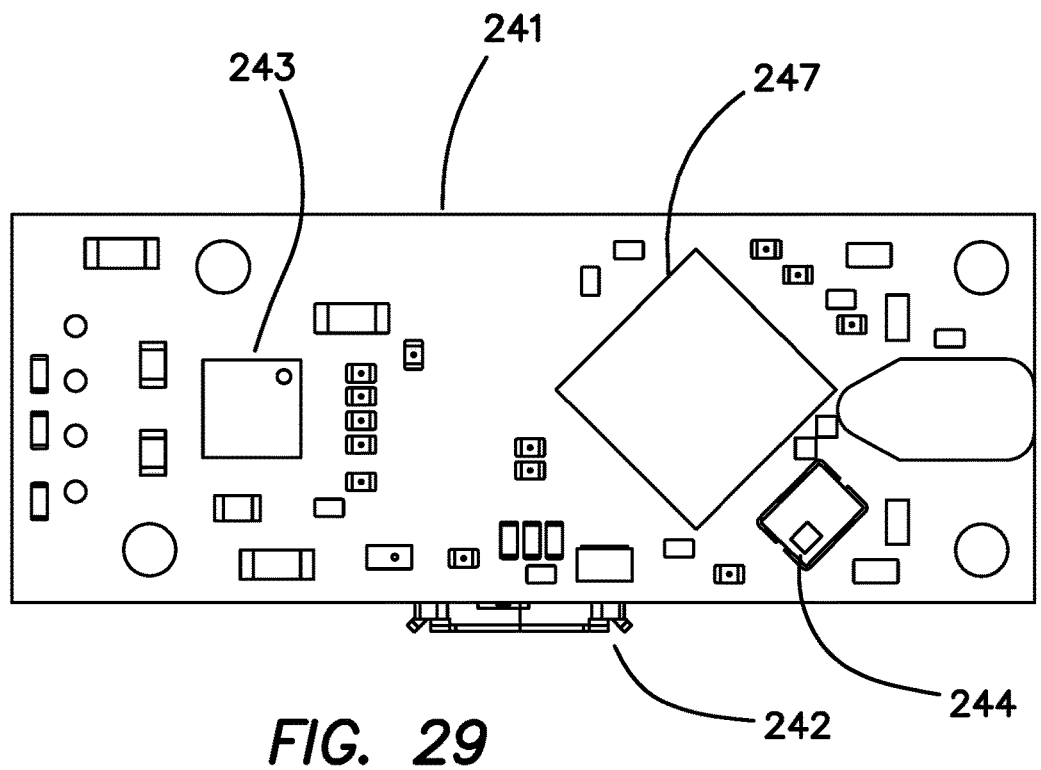
FIG. 29 is a top view of a circuit board according to the present invention.

The circuit board 241 is shown in FIG. 29. The board 241 includes sensors 244, microprocessor 247 and a communication port 242 configured for communication with an external computer 239. The board 241 includes a 9-degree-of-freedom inertial measurement unit (9-DOF IMU) 244 and a high-resolution analog-to-digital converter (ADC) 243. The IMU 244 is comprised of a 3-axis accelerometer, 3-axis gyroscope, and 3-axis magnetometer. There are electrostatic discharge (ESD) diodes located between the ADC and ground to prevent electrical failure when the device is exposed to an electrical shock. When utilized together along with appropriate calculations, information regarding the user's movement can be determined.

Figure 30:
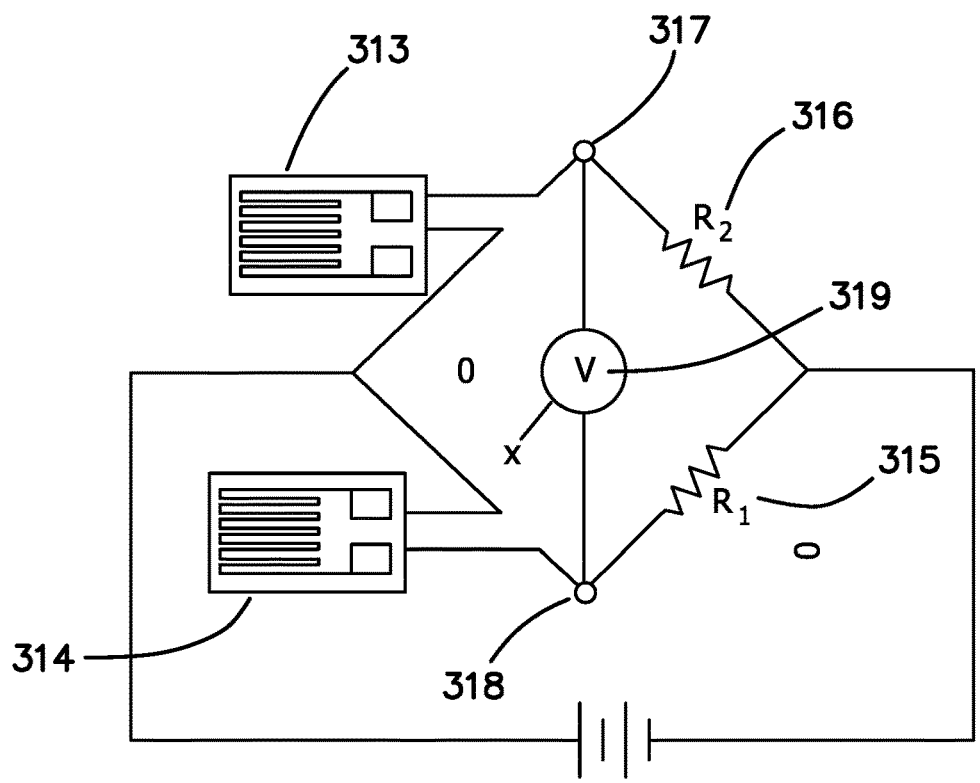
FIG. 30 is an electrical schematic of a strain gauge configuration according to the present invention.

The ADC 243 compares the voltages of the strain gauge bridge circuit seen in FIG. 30. As can be seen in FIG. 30, the strain gauges 313 and 314 are configured such that axially applied loads stress the gauges 313 and 314 resulting in a change in resistance between the gauges and the accompanying resistors 315 and 316 which form each node 317 and 318. Each strain gauge is connected to a resistor 315 and 316 such that this change in resistance results in a measurable difference between the resistive components forming each node 317 and 318 and, as a result, the voltage 319 measured between the nodes 317 and 318. The ADC 243 measures this difference and, through the use of appropriate calculations, the force applied at the instrument tip can be determined. In regards to communication with an external computer, as can be seen in FIG. 28, the board 241 located inside the housing 240 is connected to an external computer 239 and powered by way of a micro-USB type 2.0 connector 238, 242.

Figure 31A:
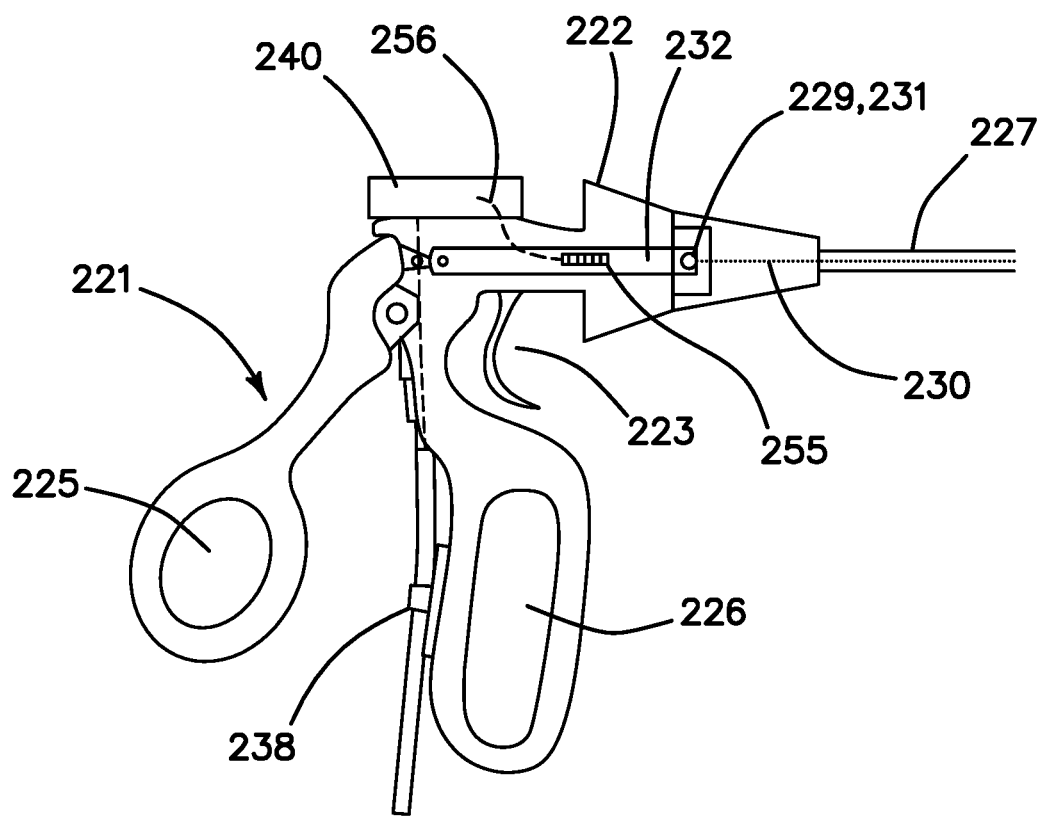
FIG. 31A is a side elevational, section view of an instrument handle assembly and shaft assembly according to the present invention.

Turning now to FIG. 31A, force sensing technologies coupled to the handle 221 that make use of strain gauges 255 are provided. The present invention positions the strain gauges 255 on the movement arm 232 inside the handle 221. Wires 256 connected to the strain gauges pass through the handle 221 to the circuit board 241 inside the housing 240. It is worth noting that the present invention places the strain gauges on the movement arm in a half-bridge configuration. With the strain gauge on the handle assembly, the longevity of the instrument is increased because when the shaft is interchanged with the handle there are no stresses placed on the gauge and connecting wires. During interchanging of the shaft, the wires remain advantageously concealed and protected inside handle assembly and are not exposed or stretched inadvertently as would be the case if the sensors were placed on the shaft. Placement of the sensors in the handle assembly advantageously allows for shorter wires. However, moving parts inside the handle may rub and wear out the wires. Accordingly, the wires are coated in polyetheretherketone (PEEK) to protect and prevent wear from abrasion encountered inside the handle. The small gauge of the wires and the PEEK coating prevent the lead wires from wearing and provide a longer lifetime and more accurate data.

As can be seen in FIG. 31B-31C, strain gauges 255 are applied on opposite sides of the movement arm 232 such that a half-bridge may be formed by connecting the strain gauges 255 in the appropriate manner. In this fashion, applied force is monitored as a function of the axial deformation of the movement arm 232 during use. The sensitivity of this sensing setup is controllable, in part, by changing the material that the movement arm 232 is made of. A larger sensing range is implemented by making the movement arm 232 out of materials with low elastic moduli such as hardened steel. On the other hand, use of materials with higher elastic moduli, such as aluminum, result in a lower overall sensing range and a higher sensitivity as the movement arm 232, and as a result the strain gauges 255, deform more under axially loading. Use of aluminum also increases the likelihood of a failure of the movement arm at the rear webbing and at the socket when exposed to high grasping forces. To mitigate the deformation, the thickness of the rear tabs was increased and the thickness of the front of the socket was also increased.

With reference to FIGS. 31D-31E, the strain gauges 255 on the movement arm 232 are not only sensitive to axial loads produced while interacting with an object at the tips, but are also sensitive to bending stress 257 transferred from the force 258 applied to the instrument shaft 227 to the movement arm 232. The movement arm 232 is preferably made of aluminum 775. The strain gauge is calibrated for outputting force at the tip of the instrument. This output is compared against a force value pre-determined to harm or damage tissue for a particular procedure. Such information as to the appropriate use of force and level of respect for tissue is provided to the user as feedback at the end of the procedure as will be discussed later herein.

In addition to measuring the force applied by the user, a user's motion and instrument position may also be monitored in a mock surgical procedure or practice. Systems and methods for tracking instrument position and user movement while training with simulated organ models are provided. Feedback to the user is provided based on the collected and analyzed data to assist in teaching and training the user. Various and multiple surgical instruments and accessories, including but not limited to graspers, dissectors, scissors, needle drivers, etc. can be employed with the systems described herein for motion tracking. Data gathered from the sensorized surgical instruments can be used to compare an inexperienced trainee's performance to that of an experienced surgeon and provide appropriate feedback. The skills gained in this manner may improve the rate of skill acquisition of trainees and, as a result, improve surgical outcomes.

Figure 32:
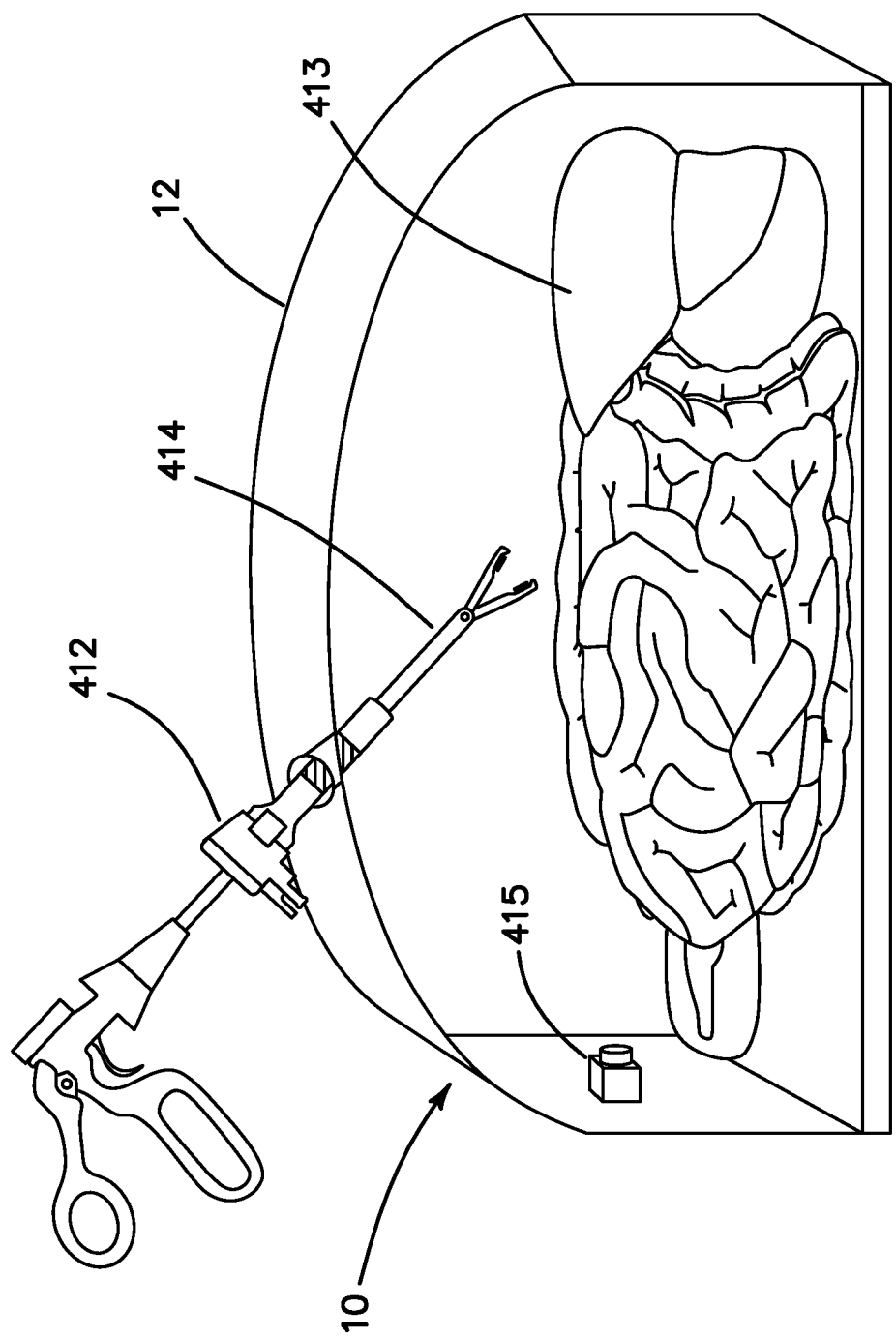
FIG. 32 is a top perspective view of a laparoscopic surgical instrument, trocar and simulated organs inside a laparoscopic trainer according to the present invention.

With reference to FIG. 32, a surgical simulator 10 is shown for laparoscopic procedures that permit a trainee to practice intricate surgical maneuvers in an environment that is safe and inexpensive. The simulator 10 generally consists of a cavity 12 comprising an illuminated environment that can be accessed through surgical access devices commonly referred to as trocars 412. The enclosure is sized and configured to replicate a surgical environment. For instance, the simulator may appear to be an insufflated abdominal cavity and may contain simulated organs 413 capable of being manipulated and "operated on" using real surgical instruments 414, such as but not limited to graspers, dissectors, scissors and even energy based fusion and cutting devices. Additionally, the enclosure often makes use of an internal camera 415 and external video monitor.

More advanced simulators may also make use of various sensors to record the user's performance and provide feedback. These advanced systems may record a variety of parameters, herein referred to as metrics, including but not limited to motion path length, smoothness of motion, economy of movement, force, etc. The present invention is configured to track the user's movements and the position of utilized instruments, interpret the collected information and use it to improve user performance through feedback and appropriate teaching instructions. Different methods for monitoring and collecting motion and position data will be now described.

Figure 33:
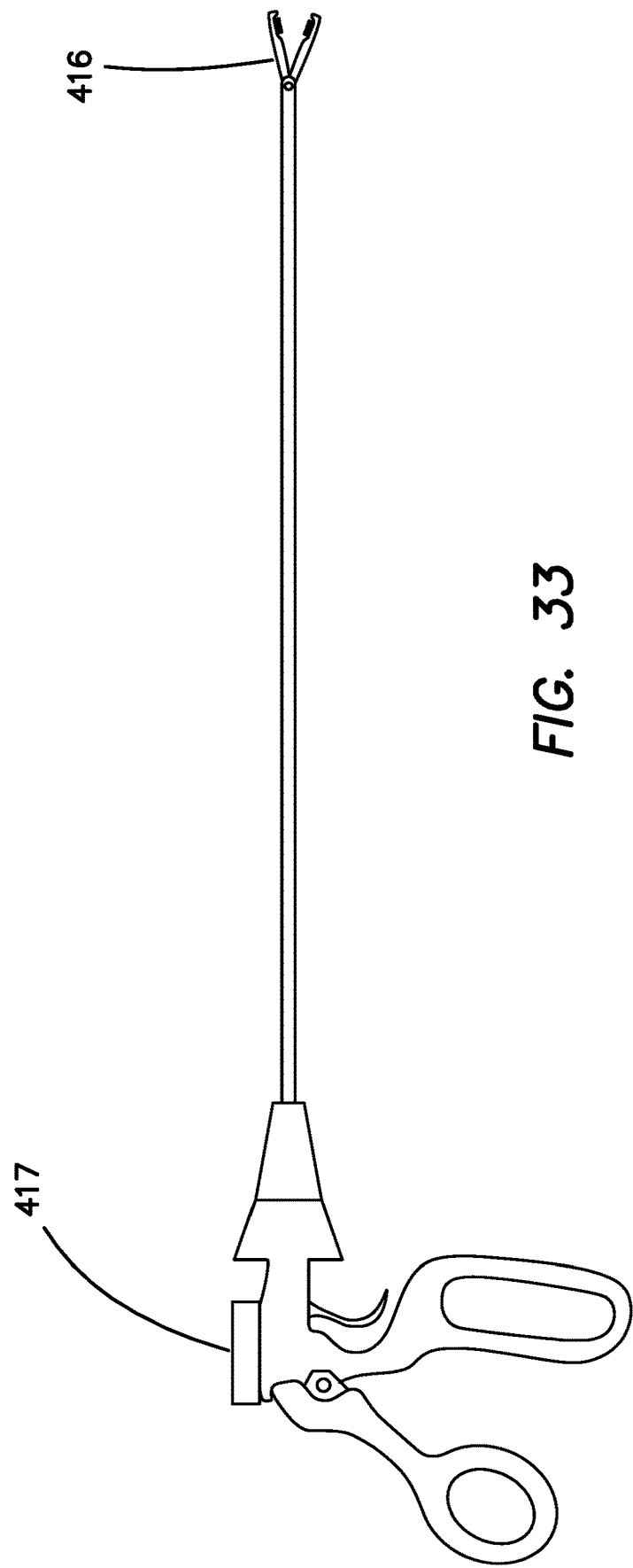
FIG. 33 is a side elevational view of a laparoscopic instrument having an inertial motion unit on a handle assembly according to the present invention.

In reference to FIG. 33, a laparoscopic grasper 416 that includes an inertial motion unit (IMU) 417 consisting of a magnetometer, gyroscope and accelerometer is shown. Data collected from the IMU 417, such as acceleration, angle, etc., is utilized to determine metrics such as, but not limited to, motion smoothness, economy of motion and path length. This information is obtained by collecting the raw IMU data (such as acceleration, angular velocity, and azimuth) in real time and analyzing it on a connected computer.

After various data is collected from the one or more sensors described above, the data is processed to extract meaningful surgical laparoscopic skills assessment metrics for providing constructive user feedback. User feedback can be tailored to identify strengths and weaknesses without relying on the subjective assistance of a third party. Users can view their feedback after completing a module, task or procedure on the training system. Some examples of metrics that are computed for performance feedback include but are not limited to (i) the total time it takes for the procedure to be completed, (ii) the average smoothness of motion of tool tips, (iii) the average economy of motion (i.e. efficiency), (iv) the average speed of motion at the tool tips, (v) the average work done, and (vi) the average energy efficiency at the tool tips.

A nine degree-of-freedom (DOF) inertial measurement unit (IMU) is used as the means for motion tracking. The IMU consists of a combination of sensors including an accelerometer, a magnetometer, and a gyroscope. Raw analog voltage measurement is converted into raw digital values in units pertinent to their specific sensor. The accelerometer measures the acceleration of the device on x, y, and z axis (in both positive and negative directions) in reference to gravitational force converted into units of acceleration ($m/s^2$). The magnetometer measures the earth's magnetic field in gauss units. The gyroscope measures the angular velocity of the device about all three axes in radians per second (rad/s). A total of nine values are collected from the IMU per sample. For force measurement, 2 strain gauges are attached to a metal strut situated within the grasper, which is primarily used to translate the grasper actuation to the grasper tips. Each type of sensor is calibrated before data is collected. Samples are received approximately every 20 milliseconds, saved into a database upstream, and passed into the data analysis utility. The data analysis utility includes data pre-processing, orientation analysis, and metrics analysis.

Figure 34:
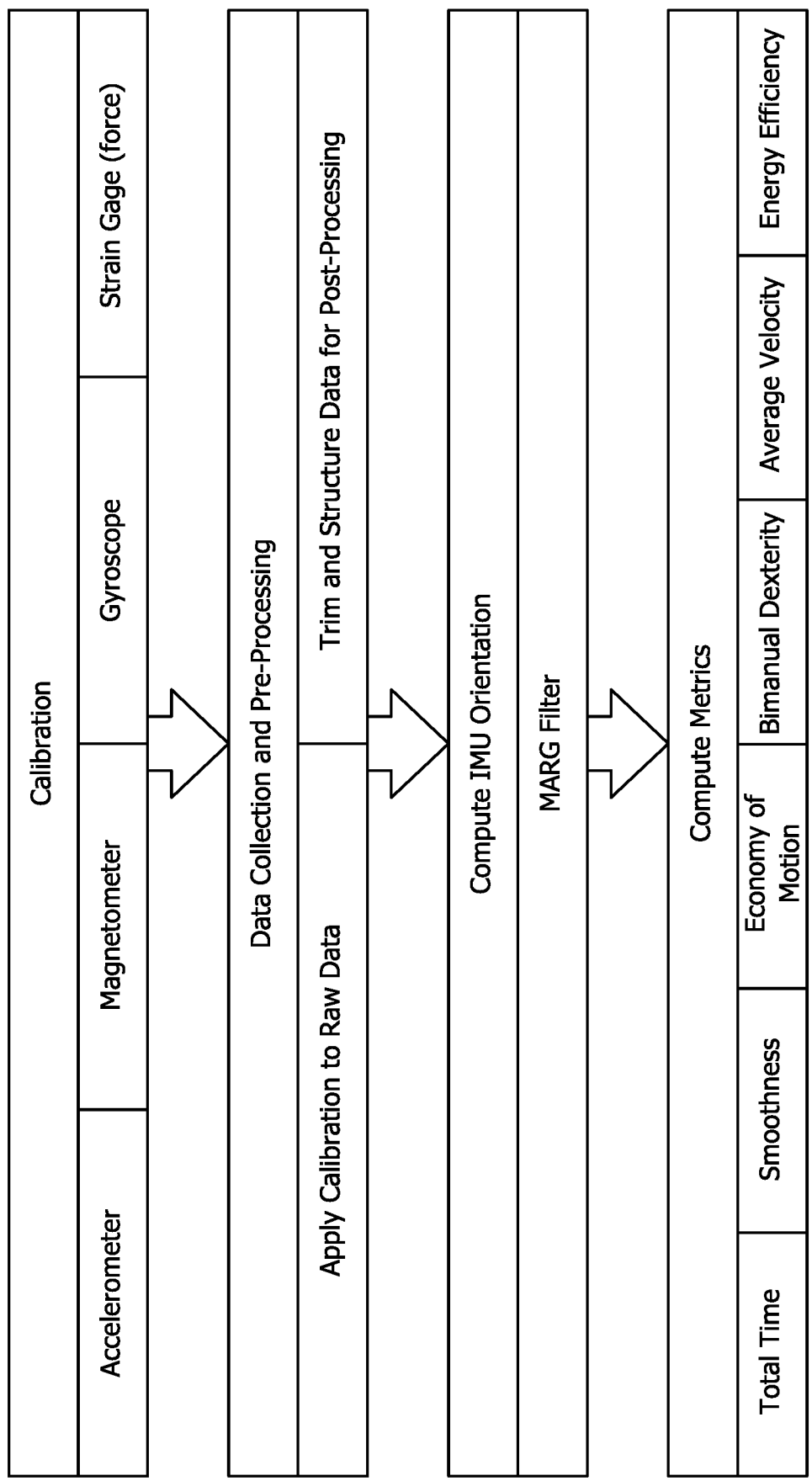
FIG. 34 is a flow chart of steps taken by a system according to the present invention.

Once raw data has been collected and calibrated, data is pre-processed, and some preliminary analysis is performed before metrics are calculated. The three reliable and well-tested metrics to measure a user's performance in simulators are (1) the time taken to complete the task, (2) smoothness of motion, and (3) economy of motion. Data analysis algorithms aim to quantify these metrics as will be detailed hereinbelow. Other metrics, such as average velocity of the tool tips, and energy efficiency will also be added into the analysis. Once metrics computation is complete, the results are graphically conveyed to the user for performance feedback. This overview of data processing and analysis is illustrated in FIG. 34.

Before any type of analysis is done with the data, the data is pre-processed to ensure the data itself reflects as closely to the true value as possible. No two sensors are completely identical, and their signal responses will always present a slight margin of error due to inherent hardware variability. By calibrating the sensors, the difference between the raw sensor signal output and the true value is characterized as a constant or a function depending on whether the relationship is linear or nonlinear. Each sensor will have a unique calibration constant or set of coefficients that are used to compensate for errors in all the signals generated from each specific sensor. For this invention, there are a total of four types of sensors (accelerometer, magnetometer, gyroscope, strain gauge) that need to be calibrated, each requiring a different calibration method.

Figure 35:
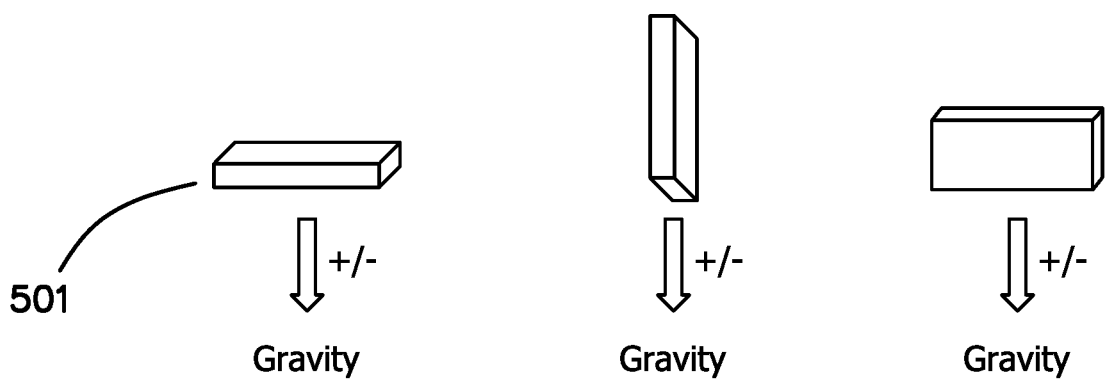
FIG. 35 is a schematic of an accelerometer calibration method and equations for all axes in both positive and negative directions according to the present invention.

Turning now to FIG. 35, the accelerometer 501 is calibrated using gravity as its reference. The IMU device is oriented with one of its 3 axes perpendicular to the ground and held at that orientation before the signal is recorded and averaged over a span of a few seconds. The same is done on the opposite orientation (same axis). This is repeated for all three axes. A total of 6 gravity acceleration values are measured, 2 for each x, y, and z axes. The average 518 of the two values will be the offset for each axis.

$$Acc_{calibrated\_x} = Acc_{raw\_x} - (Acc_{x\_positive} + Acc_{x\_negative})*0.5$$

$$Acc_{calibrated\_y} = Acc_{raw\_y} - (Acc_{x\_positive} + Acc_{x\_negative})*0.5$$

$$Acc_{calibrated\_z} = Acc_{raw\_z} - (Acc_{x\_positive} + Acc_{x\_negative})*0.5$$

The magnetometer is calibrated using the earth's magnetic field as its reference. Magnetic measurements will be subjected to distortions. These distortions fall in one of two categories: hard or soft iron. Hard iron distortions are magnetic field offsets created by objects that are in the same reference frame as the object of interest. If a piece of ferrous or metallic material is physically attached to the same referencing frame as the sensor, then this type of hard iron distortion will cause a permanent bias in the sensor output. This bias is also caused by the electrical components, the PCB board, and the grasper handle that the circuit board is mounted on. Soft iron distortions are considered deflections or alterations in the existing magnetic field. These distortions will stretch or distort the magnetic field depending upon which direction the field acts relative to the sensor.

Figure 36:
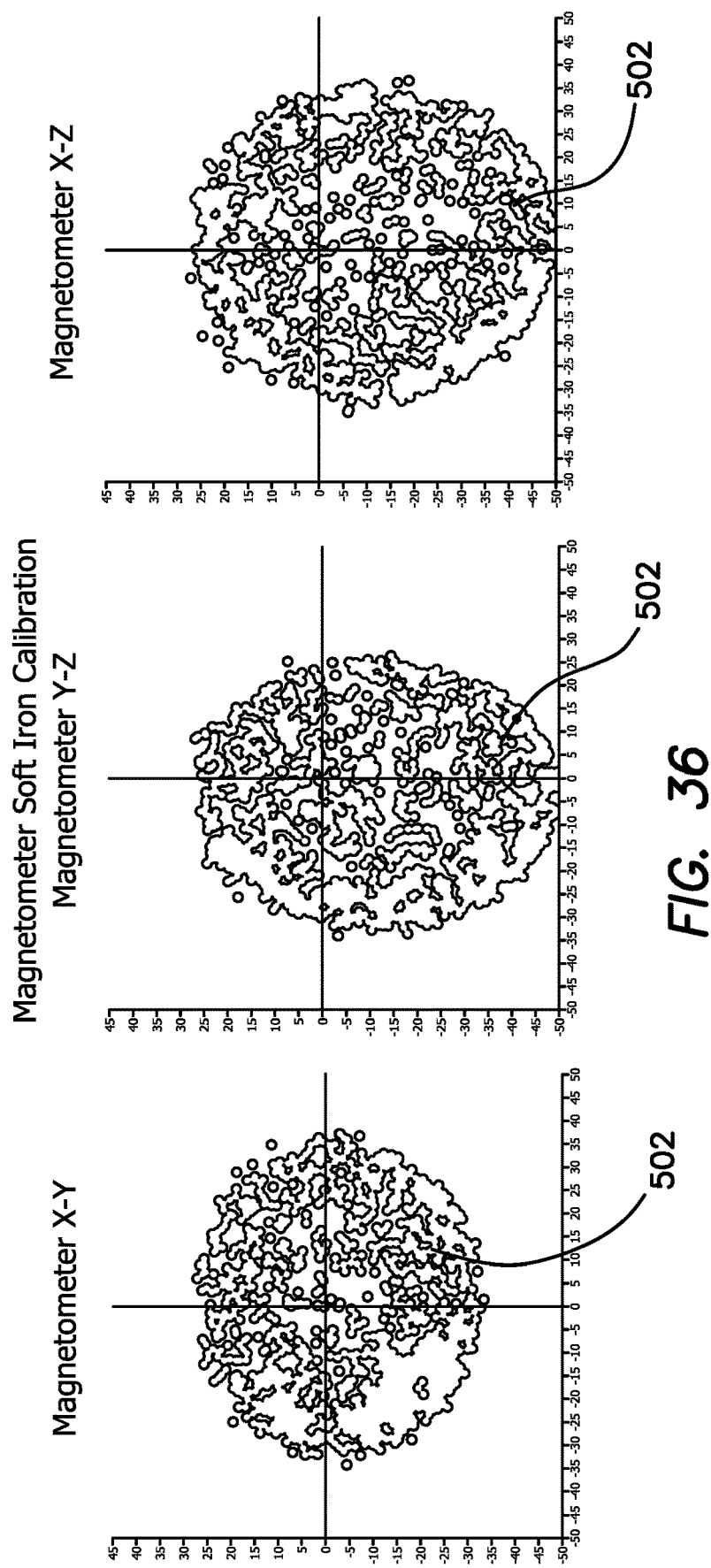
FIG. 36 is a schematic of a magnetometer calibration model according to the present invention.

Referring now to FIG. 36, to calibrate the IMU, the IMU is oriented at as many angles and directions as possible to attain an even amount of data points to model a spherical representation of the earth's magnetic field. Once the raw magnetometer data 502 is recorded, it is fit into an ellipsoid using a fitting algorithm. The ellipsoid center and coefficients are calculated. The center values reflect the hard iron bias of the device, while the coefficients characterize the soft iron distortion (i.e. the shape of the distorted magnetic field surrounding the device). Assuming that the earth's magnetic field is at the origin, and is perfectly spherical, the center offset and the transformation matrix can be calculated as follows:

$$Mag_{center} = [m_{center\_x}, m_{center\_y}, m_{center\_z}]$$

$$Mag_{transform} = \begin{bmatrix} m_{xx} & m_{xy} & m_{xz} \\ m_{yx} & m_{yy} & m_{yz} \\ m_{zx} & m_{zy} & m_{zz} \end{bmatrix}$$

$$Mag_{calibrated} = (Mag_{raw} - Mag_{center}) \times Mag_{transform}$$

The gyroscope measures angular acceleration, which means that when the device is perfectly still, a perfect gyroscope's signal output will be 0 rad/s. To calibrate the gyroscope, the device is laid completely still while raw gyroscope signals are recorded. A total of 3 values are measured and used to compensate for the error and noise.

$$Gyro_{calibrated} = Gyro_{raw} - Gyro_{atRest}$$

Figure 37:
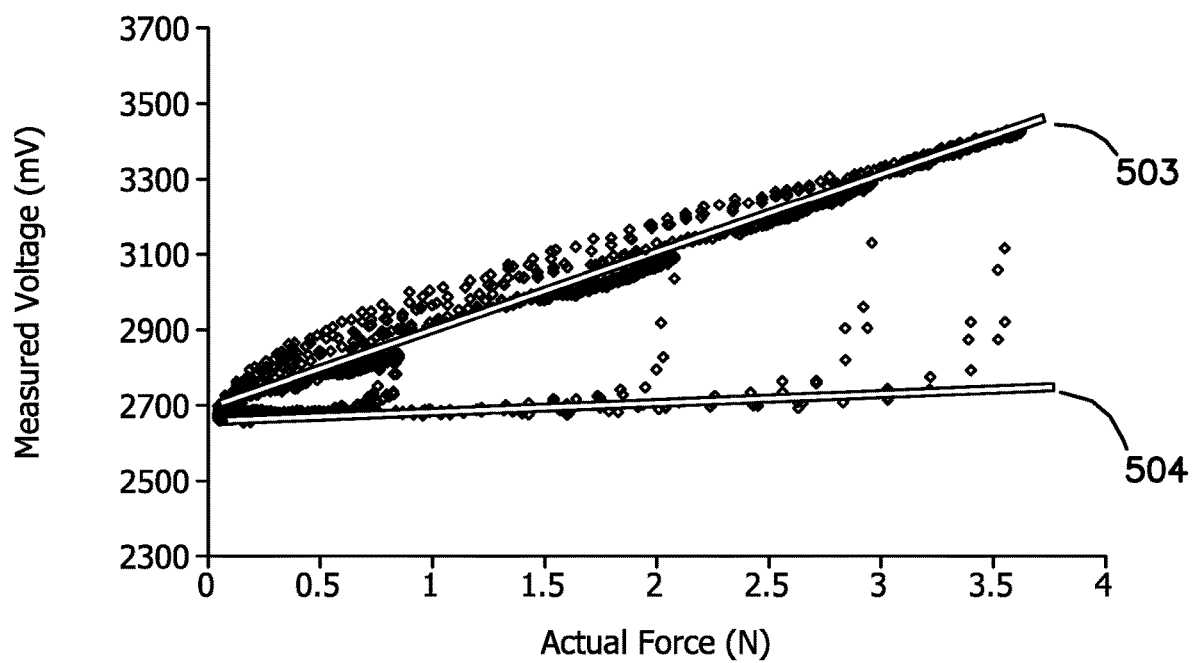
FIG. 37 is a strain gauge calibration plot of measured voltage against actual force measured by a load cell for calibration according to the present invention.

The strain gauges are calibrated using a load cell as a reference. Each grasper handle has two strain gauges placed on opposite sides of the metal strut as shown in FIG. 31B. The strut is loaded axially, and the strain gauges are each interconnected to a Wheatstone bridge, which measures the change in resistance of the strain gauges due to the compression or elongation of the metal bar. Traditionally, a load cell can be used to directly characterize the strain gauge signal in response to load. The manner in which the bar is assembled into the handle is important because it can introduce complications that prevent accurate force measurements using the load cell. One end of the metal bar is connected to the actuator where the grasper is held, and the other end is connected to a rod that in turn actuates the grasper tips. Between each end of the bar and their respective sites of actuation are many joining parts that work together to transfer force from the handle to the grasper tips. These joining parts, in order to allow movement, are designed with clearance. When there is a change in direction of load (e.g. closing the grasper as soon as it has been opened), the separate parts will have to travel through this void before they make contact with their adjacent parts again. This phenomenon causes different force readings on the same load applied in opposite directions (i.e. compression or tension), and is known as backlash. Calibration is done by observing the difference in response of the strain gauge and the load cell when the grasper is loaded (gripped), and when it is being released. FIG. 37 shows that the strain gauge response will follow a different trend line when force is being loaded and when it is being released due to backlash. An algorithm is written to automatically estimate the closest polynomial fits to both the upper 503 and lower 504 trend lines, resulting in two sets of polynomial coefficients. It separates the two lines by first fitting all the data points to create a single trend line that passes between the top and bottom trend lines of interest, which acts as a threshold line to separate data points that belong to the top line from those that belong to the bottom line. It then sweeps through the data over time and estimates whether the grasper is being loaded in one direction or the other. The algorithm then applies the corresponding polynomial coefficients to solve for true force being applied at the grasper tips.

Figure 38:
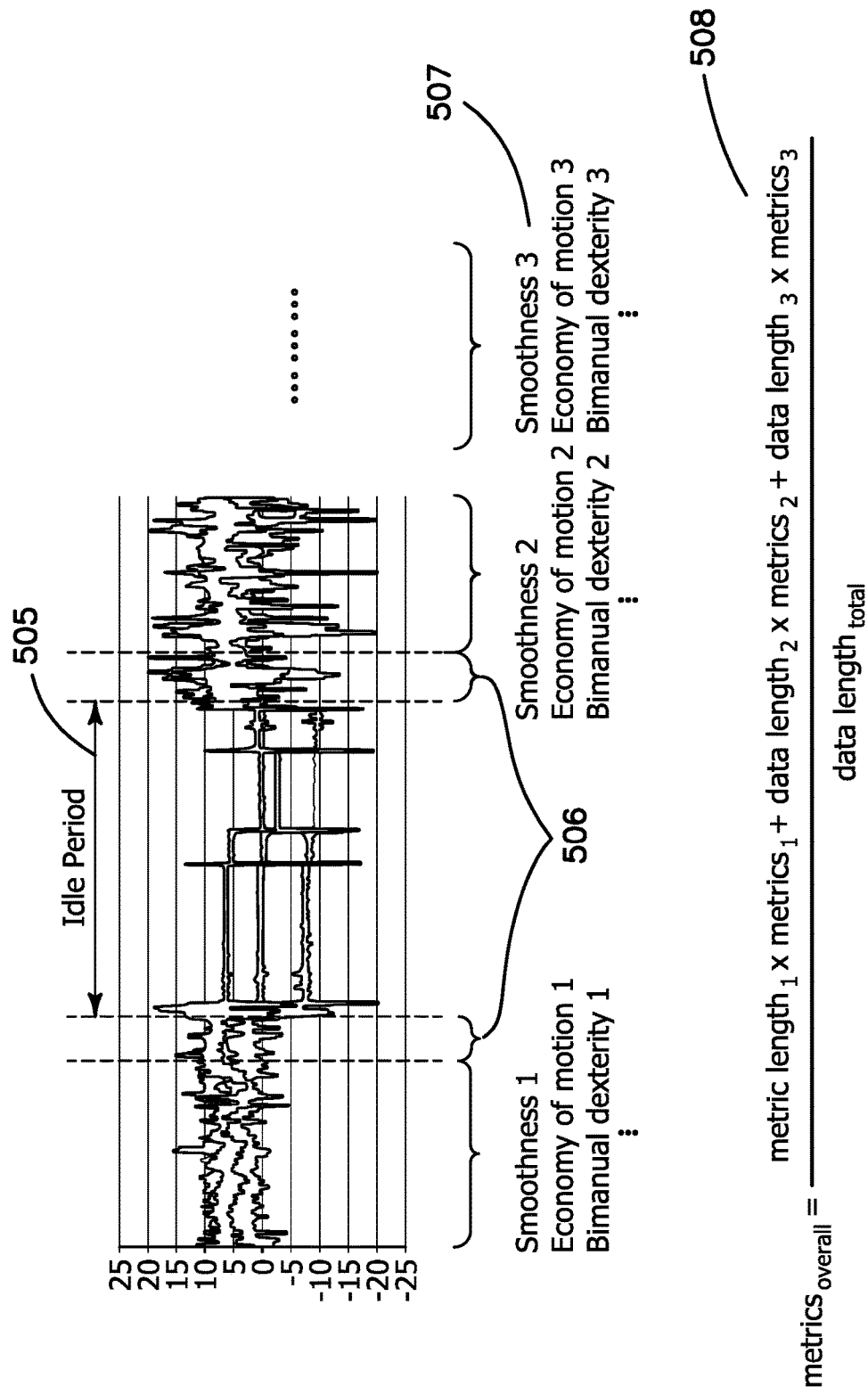
FIG. 38 illustrates a trimming and segmentation method for calculating the timing according to the present invention.

To ensure analysis is as relevant to actual surgery as possible, both the user's dominant and non-dominant hand movements are tracked simultaneously. After each of the sensors is calibrated correctly, and prior to performing any analysis, time is one metric that can be obtained. Unfortunately, due to the nature of certain surgical simulation procedures, the user is occasionally required to put down the device mid-session. Since the length of time in which the device stays inactive in this form does not directly reflect on the skill of the user, this idle factor is eliminated from the analysis in one variation. An algorithm to trim off these idle portions 505 is shown in FIG. 38. It does so by sweeping through each of the axes of the accelerometer data, and calculating the derivative over time. When derivative is zero or close to zero, it is assumed that there is no motion along that axis. If the derivative remains to be zero or close to zero for more than 6 seconds, it is considered to be set aside. A buffer 506 of approximately 3 seconds is added to each of the ends of the idle start and end times 505 to account for movements relating to the picking up or putting down of the device. The final start and end idle time is used as a reference for downstream processing to identify the locations at which the data is to be segmented at. Useful data separated by intermediate idle regions, is segmented and stored into an array list separated by order 507 (i.e. a data set with 3 idle periods will have 4 data segments). Segments that belong to a single data set will be individually analyzed successively 507 and be added to find total active time to complete the task. The total active time to complete the task is when at least one of the tools is not idle, and then the user is considered to be actively performing the task. Once data has been segmented, and calibration has been applied to the raw data, this information can be used to calculate orientation of the device over time. A sensor fusion algorithm that has been developed to combine accelerometer, magnetometer, and gyroscopic data to estimate the orientation of the device over time is the Magnetic, Angular Rate, and Gravity (MARG) filter developed by Sebastian Madgwick illustrated in FIG. 39.

In order to understand how the algorithm is implemented, one must first understand how each component in the IMU contributed to the overall estimation of orientation of the device. Since the gyroscope measures angular velocity in all three axes, theoretically, these values can be integrated to obtain angular displacement. Unfortunately, as with the case for most sensors and discrete digital signals, integration and quantization error are almost always unavoidable. The result is that these small errors in the estimated displacement will quickly accumulate over time until the estimated orientation "drifts" significantly and no longer estimates the orientation correctly. The accelerometer and magnetometer is therefore present to provide reference for the gyroscope. Since the accelerometer measures acceleration along all three axis, it is also able to detect the direction gravity is pointed relative to its own orientation. When the device is tilted slightly at an angle, the direction of gravity relative to the orientation of the device also tilts slightly at an angle identical but opposite the tilting motion. With some basic trigonometry, the roll and pitch of the device can be estimated. The roll and pitch are the angles at which the device is rotated about the axis on a plane parallel to the ground. There are several limitations to exclusively using the accelerometer to estimate orientation. Firstly, since accelerometers are also sensitive to acceleration forces other than gravity, data is susceptible to error if there is linear motion of the device. Secondly, yaw, which is the angle of rotation about the axis perpendicular to the ground, cannot be estimated since the direction of gravity with relation to orientation of the device will not change if the device is oriented north or east for example. Yaw is, instead, estimated using the magnetometer. The magnetometer is essentially a digital compass that provides information about the magnetic heading of the device, which can be converted into yaw angles. The accelerometer and magnetometer estimations, when combined with the gyroscope orientation estimations by an algorithm, acts as a filter that helps dampen the effects of integration errors in the gyroscopes.

Figure 39:
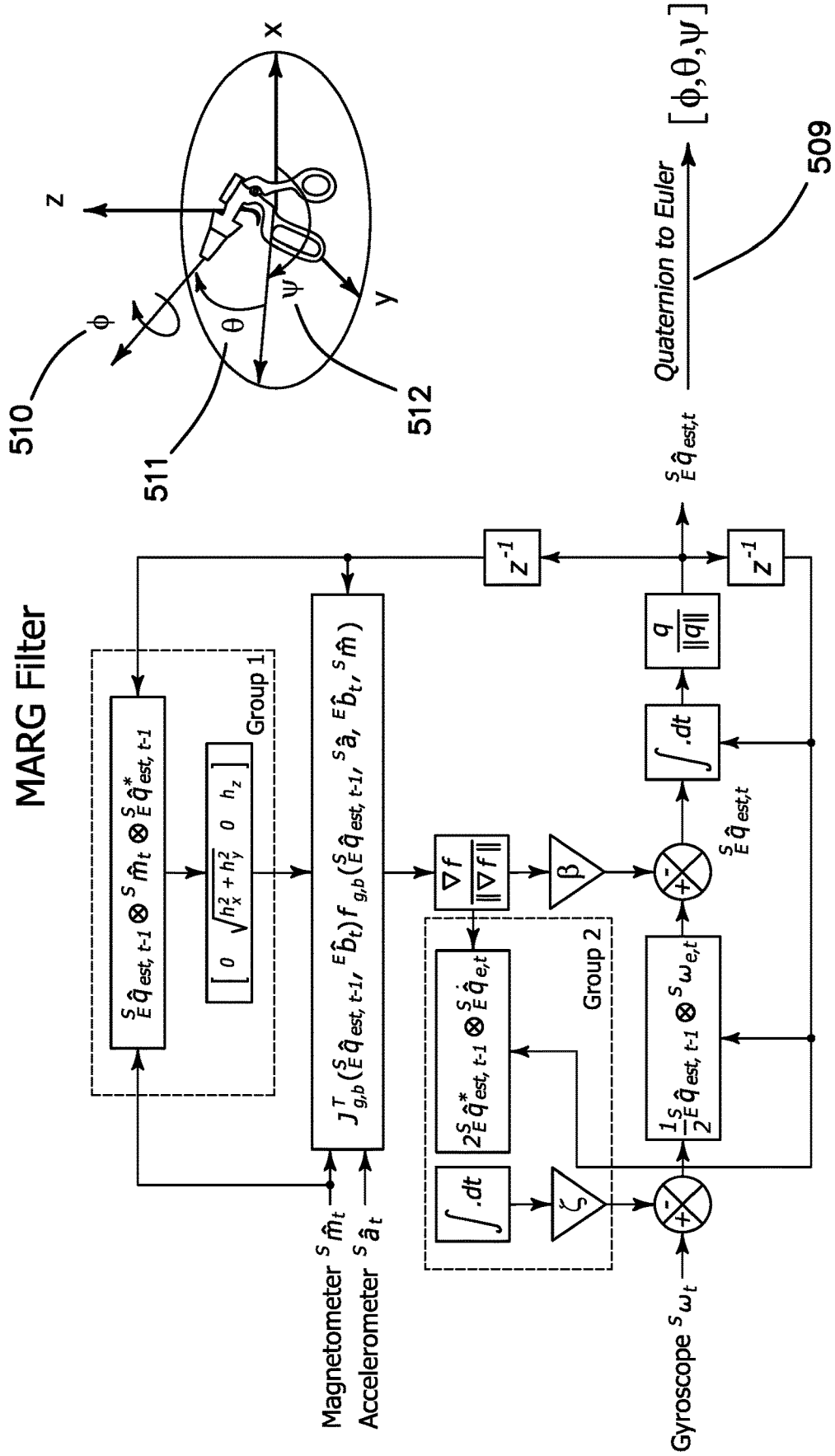
FIG. 39 is a flow chart of data in a MARG algorithm, an IMU orientation estimation algorithm according to the present invention.

When dealing with orientations in algorithms, some common mathematical representations include Euler angles and the quaternion representation. Referring to FIG. 39, the MARG filter uses the quaternion representation, and applies gradient-decent to optimize accelerometer and magnetometer data to the gyroscope data and estimate the measurement error of the gyroscope as a quaternion derivative. Quaternion results are converted back into Euler angles 509 for more intuitive post-processing of the orientation data.

Still referencing FIG. 39, the Euler angles (roll 510, pitch 511, and yaw 512) represent the angle traveled on the x, y, and z axes respectively from the original orientation. Each Euler angle representation can be converted to a unit vector notation that represents orientation. Once the orientation vector is computed, analysis will proceed to metrics computation.

Figure 41:
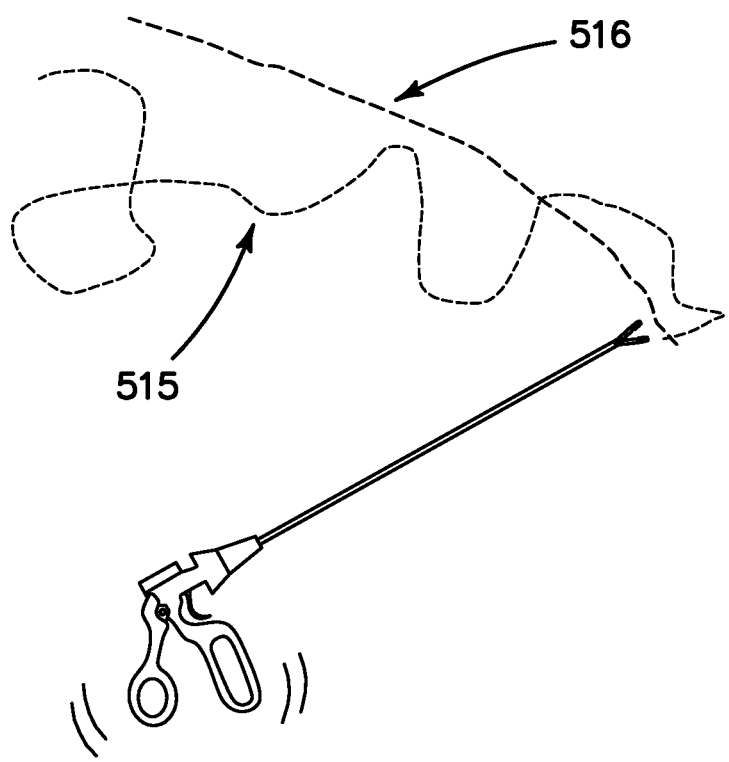
FIG. 41 is a schematic illustrating an economy of motion algorithm and equation according to the present invention.

Total active time has already been estimated prior the beginning of orientation analysis. Other metrics to consider include economy of motion and smoothness. With reference to FIG. 41, the economy of motion metric measures how well the user chooses the path of the tool tip to complete a specific procedure. In theory, the most optimal path is the shortest path possible to complete the procedure, and economy of motion is the ratio of the shortest, most efficient path to the measured path length of the user. In reality, the optimal path is very difficult to estimate as it depends largely on the type of procedure and the varying approaches that may exist even among the best of surgeons. To solve this problem, instead of estimating and comparing the measured path length to the shortest path length, the measured path length 515 is compared to the average path length of a pool of expert surgeons 516. Path length is calculated, first, by taking the dot product of adjacent orientation vectors in the data sequence, which gives the angle of change in orientation. Each angle in the data sequence multiplied by the length of the tool gives the arc length that the tip traveled. The total path length is the sum of this series of arc lengths. The path length calculated using this method is not the absolute path length, as this method assumes that there is no travel along the depth axis (i.e. grasper moving in and out axially through the trocar). The reason for this limitation comes inherently from the IMU's inability to track 3D position. IMUs are only able to accurately track orientation information. The only means to estimate 3D position is through integrating the accelerometer data twice. Although this may be a mathematically correct approach, in reality, accelerometers are very noisy. Even after filtering, the noise will be amplified each time it is integrated. Integrating each data point twice sequentially along the data series allows for error to accumulate exponentially. In other words, three dimensional position tracking can only be achieved for several seconds before the estimation drifts far away from its true 3D position. Nevertheless, the ratio of the expert path length to the user path length 517, though with an error, is assumed to be proportional to the actual ratio using their true path lengths, and is used to measure economy of motion.

With reference to FIG. 40, smoothness measures the frequency and variance of motion. It is assumed that expert data would typically show smoother motion paths than less experienced surgeons. Factors that may affect smoothness of motion include hesitation, misjudgment of lateral and depth distance of tip to target, collision of the tool tips, and lack of speed and/or force control, all of which are more apparent in novices. To begin, the position of the tool tip is estimated. As described in the previous section, absolute 3D position tracking is not possible while using an IMU. Instead, a pseudo-2D position is projected by the lateral sweeping motion of a grasper pivoting at the entry point, and assumes that there is no movement in depth. This 2D position coordinate represents the path the tip travels. The curvature K of the path over time is first calculated over time using the equation 513. Curvature gives a measure of the abruptness of change in path. The smoother the motion, the smaller the change from one curvature value to the next. Smoothness can then be quantified statistically in relation to the standard deviation of curvature change to mean of change 514. The smaller the resulting smoothness value, the less variability there is in motion, the smoother the motion path, the more skilled the user.

Other smoothness algorithms that have been tested or considered include one that applied the smoothness equation on each of the accelerometer data series separately and took the average of all the smoothness values; one that applied the smoothness values of each of the position coordinates and took the average of the resultant smoothness values; and one that performed an auto correlation of curvature. Auto-correlation is a way of calculating similarity of a signal with itself at an offset time. This is useful to find whether there is a smooth transition from one sample point to the next by offsetting by only a seconds time or even a single data point by determining how similar the offset signal is to the original signal.

Other metrics that are explored include average velocity of tool tips and energy efficiency. Average velocity is simply the distance travelled over time. Average velocity can be used in combination with other metrics to gauge confidence and familiarity with the procedure. Path length from one sample to the next has already been computed while determining the overall path length the tip of the tool travelled. Time increment between each sample increment is recorded in the raw data and can be calculated by subtracting the previous time stamp from the most current time stamp along the sequential analysis. A velocity is calculated between each sample increment and the average is taken.

Lastly, energy efficiency is computed using the force data collected from the strain gauge. Force information is important in determining if the user is using excessive forces in accomplishing the task, and hence, causing unnecessary tissue damage. Due to the fact that each data set was segmented, each of these algorithms are implemented to each segment sequentially, yielding the same number of metrics as there are segments in the data set. These individual metrics are averaged to determine the overall metric for that data set. Each individual device involved in the simulation session will have computed metrics associated to it, and these metrics will be combined for analysis overall.

The data is collected and analyzed via an interactive application installed on a computer or other microprocessing device. The application is present via a graphical user interface that is interactive offering various learning modules such as on specific laparoscopic procedures and providing user feedback on collected metrics from the sensorized instruments. The software application guides users through selecting a learning module and provides users with constructive feedback helping users increase surgical instrument handling skills and build manual dexterity.

The software can employ a variety of technologies, languages and frameworks to create an interactive software system. In particular, JavaFX® software platform, that has cross-platform support, can be used to create the desktop application. JavaFX® applications are written in Java and can use Java® API libraries to access native system capabilities. JavaFX® also supports the use of cascading styling sheets for styling of the user interface. SQLite® software library can also be used in the present invention as a self-contained, serverless, transactional SQL database engine. This database engine is used to create and insert data pertaining to each learning module into a database, as well as data collected from the user to later be analyzed. Each screen of the application is populated with learning module data stored in the SQL database. The JavaFX® embedded browser WebKit® which is an open source web browser engine may also be employed. This browser supports most web browser technologies including HTML5, JavaScript®, Document Object Module, and Cascading Style Sheets. Each step of a laparoscopic procedure is displayed in an embedded web browser in the learning module screen. The Data Driven Documents (D3) JavaScript® library may also be utilized to provide dynamic interactive visualizations of data. D3 binds data to the web browser technology, Document Object Model, to which then D3 transformations can be applied. D3 visualizations using analyzed data collected during the learning module can then be displayed in an embedded browser in the feedback screen. The Webcam Capture Java® API can also be employed to capture images from the connected laparoscope to display to the user. The live feed from the laparoscope is embedded into the learning module screen.

Figure 42:
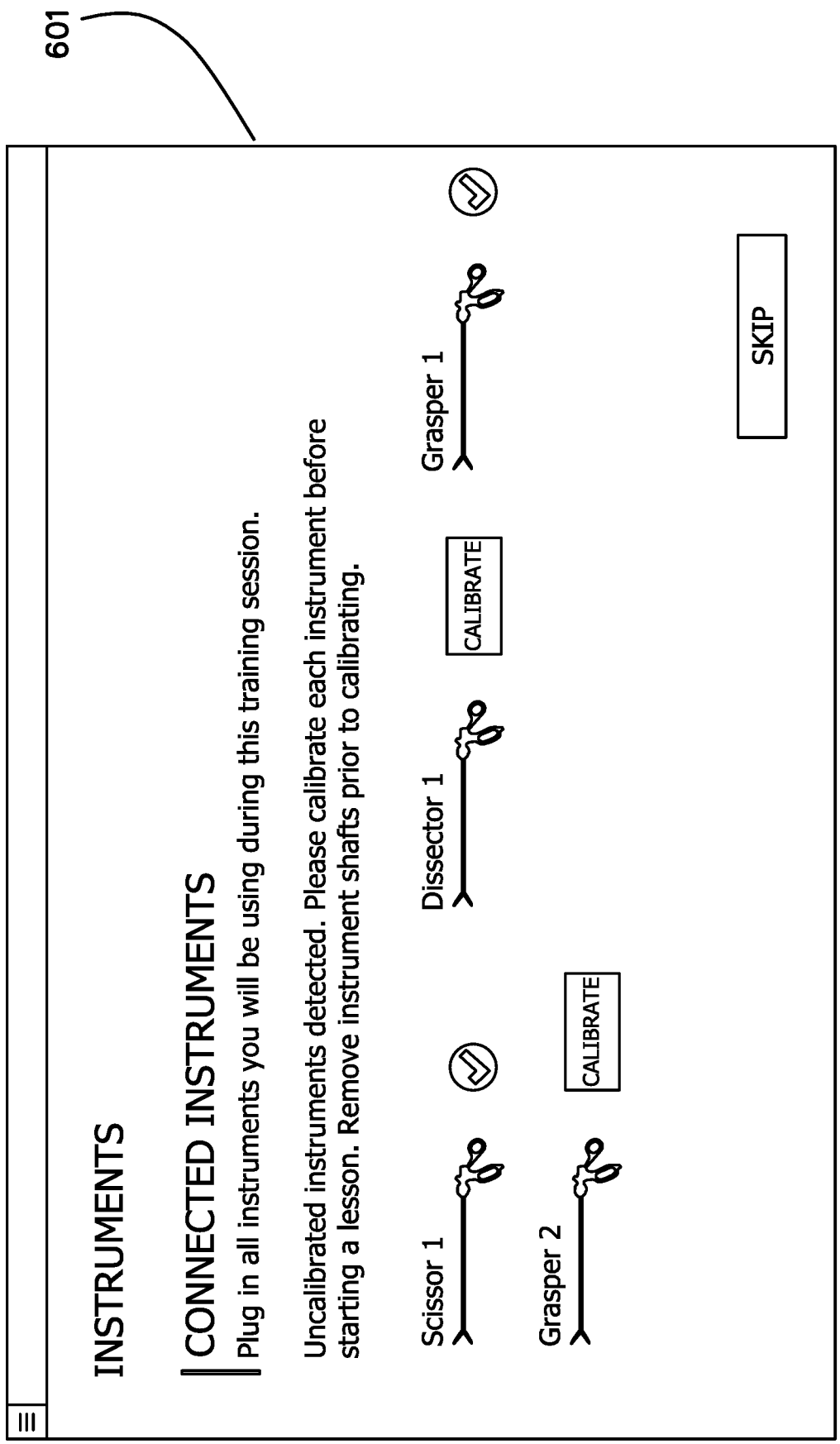
FIG. 42 is a computer screen shot view of a user interface starting page according to the present invention.
Figure 43A:
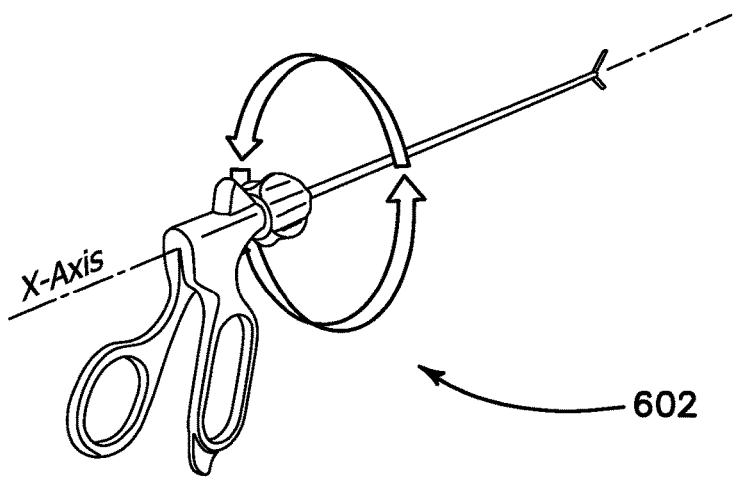
FIG. 43A is a computer screen shot view of a user interface calibration screen according to the present invention.
Figure 43B:
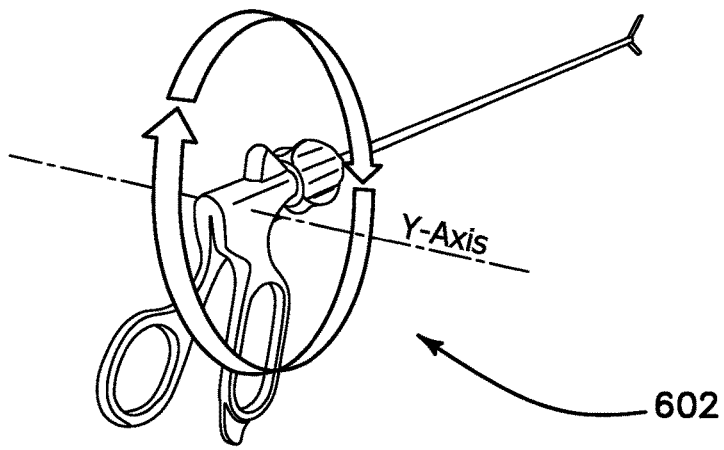
FIG. 43B is a computer screen shot view of a user interface calibration screen according to the present invention.
Figure 43C:
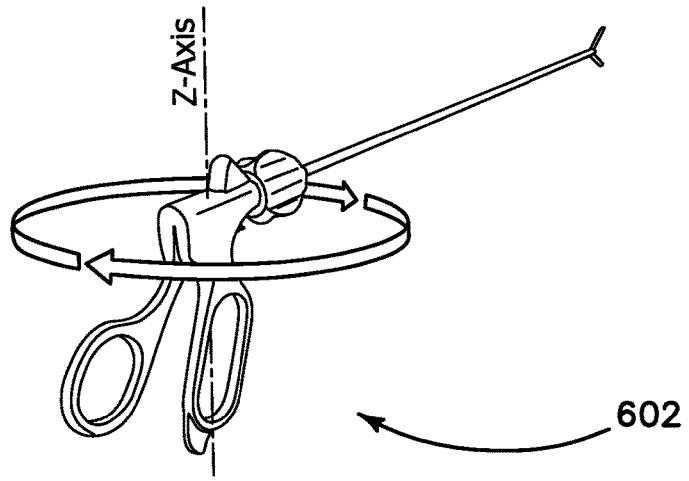
FIG. 43C is a computer screen shot view of a user interface calibration screen according to the present invention.
Figure 43D:
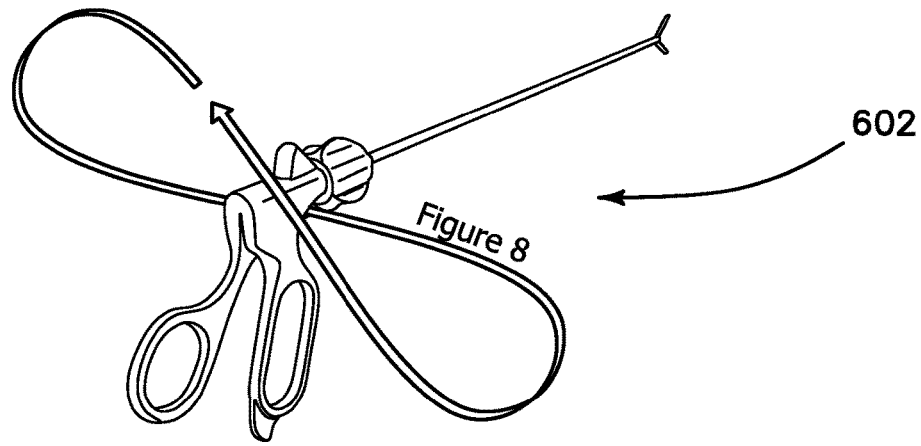
FIG. 43D is a computer screen shot view of a user interface calibration screen according to the present invention.

With reference now to FIG. 42, the module devices screen page of the user interface displays all of the connected devices 601. The graphical user interface includes virtual buttons displaying whether the magnetometers on each instrument have been calibrated. Selecting the "calibrate" button adjacent to each specific instrument will take the user to the calibration screen page where magnetometer data from that instrument will be actively recorded and stored for calibration.

Turning to FIGS. 43A-43D, the device calibration screen page is shown. The calibration screen page displays the three steps 602 of the magnetometer calibration process 602. The steps 602 include orientation about the three axes to obtain plot magnetometer data on XY, XZ, YZ planes. The application displays an animation that guides the user through the steps to properly calibrate the magnetometer for their specific sensor. In particular, the user is instructed by the calibration screen to rotate the instrument. Once the application has collected a sufficient amount of magnetometer data based on the number of points plotted on a plane in a given number of quadrants, the magnetometer data is then stored in the database 630, to be used in the analytics algorithms. The analytics algorithms correct for magnetometer bias due to encountering sources of magnetic field using an ellipsoid fit algorithm. The other sensors are also calibrated at step 600 of the flow chart shown in FIG. 49.

Figure 44:
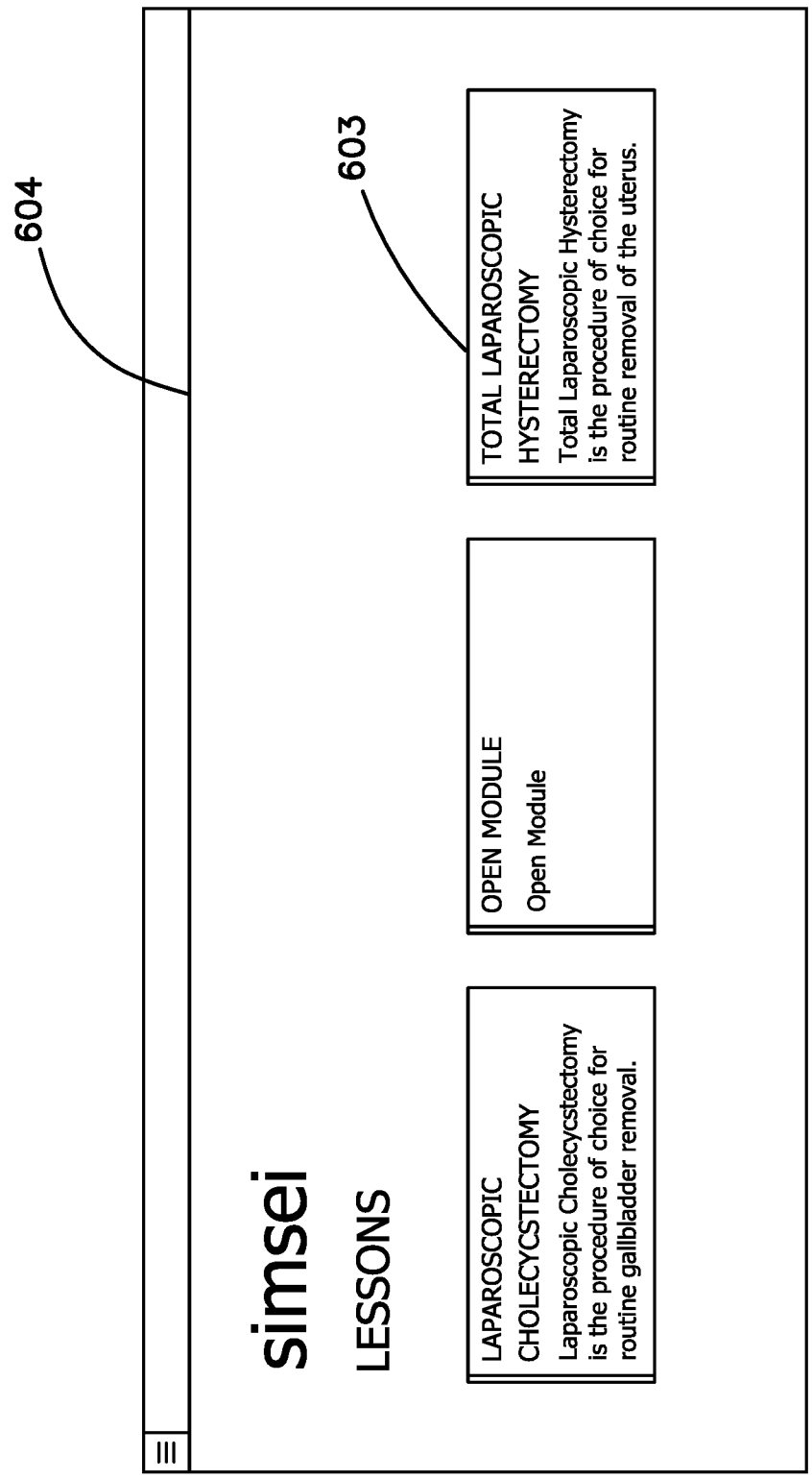
FIG. 44 is a computer screen shot view of a user interface lesson selection screen according to the present invention.
Figure 49:
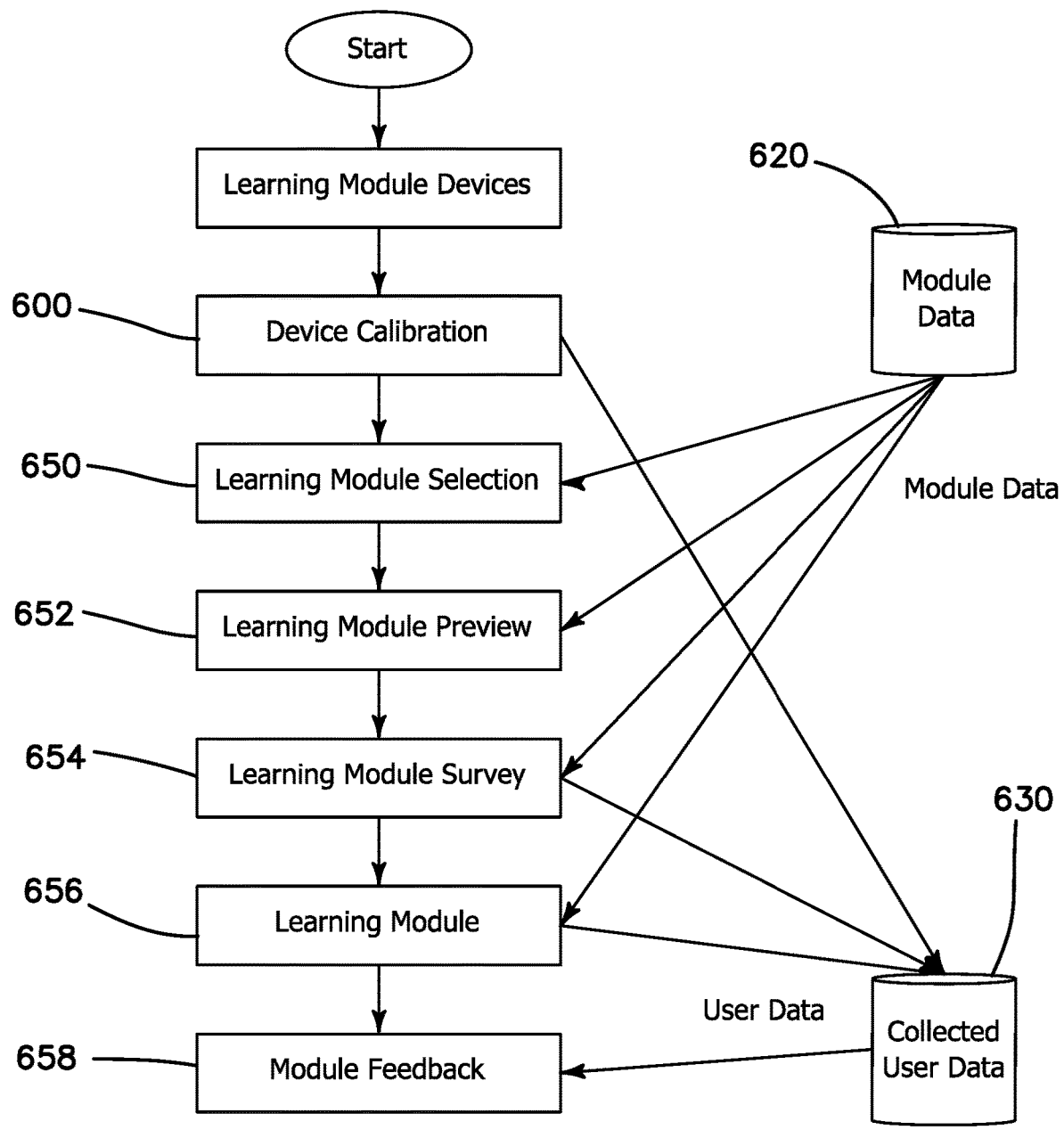
FIG. 49 is a flowchart illustrating the path of data flow according to the present invention.

With reference now to FIGS. 44 and 49, in the next step 650 the type of training module is selected on the module selection screen page using a virtual button. This screen displays available learning modules for the user to select. On the module selection screen 604, a selectable lesson 603, for example, entitled "Total Laparoscopic Hysterectomy" is displayed and includes the title and short description of the learning module. The lesson module screen is populated by querying the SQL database for stored learning modules titles and descriptions. Examples of training modules include the following surgical procedures: laparoscopic cholecystectomy, laparoscopic right colectomy, and total laparoscopic hysterectomy.

Figure 45:
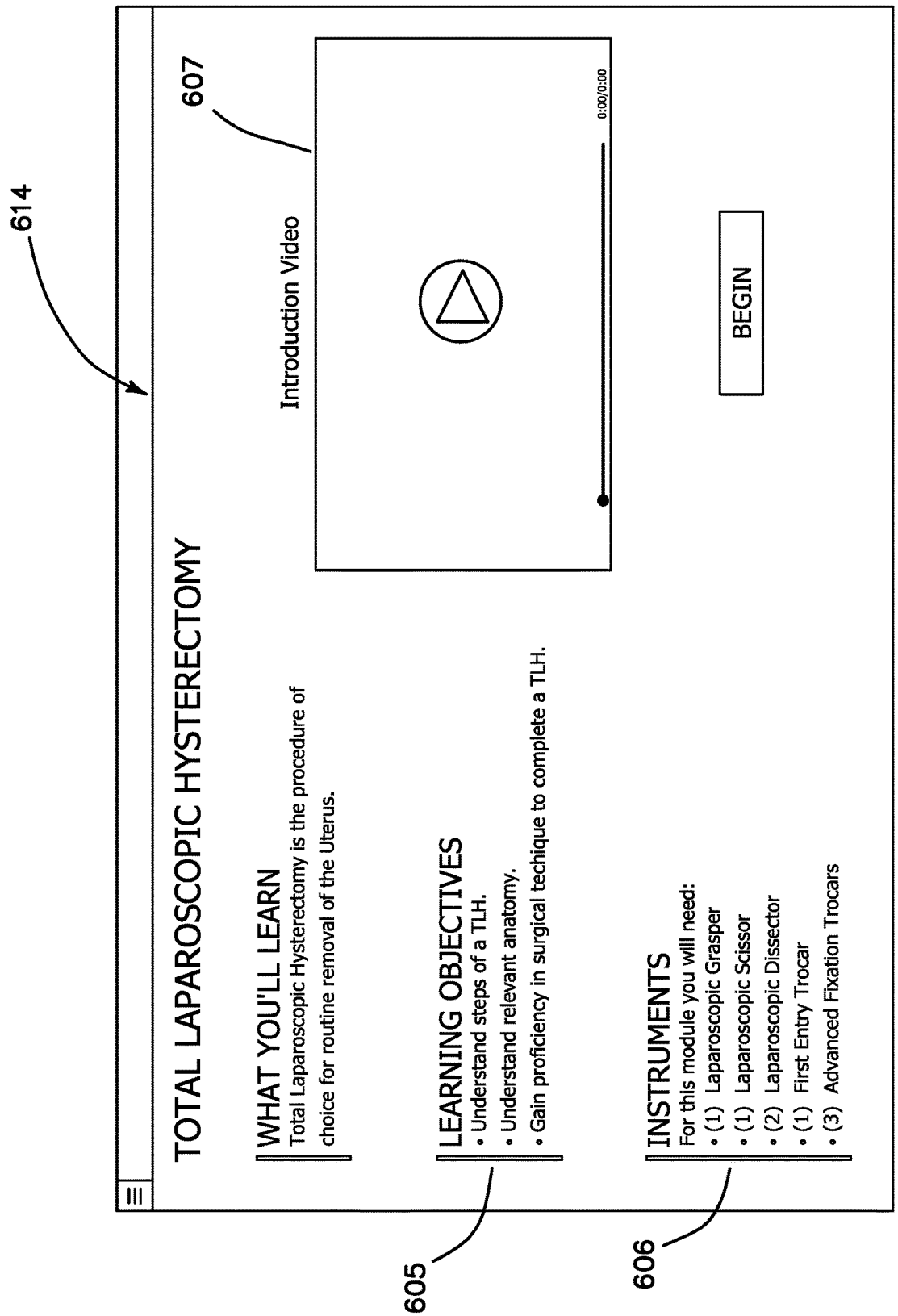
FIG. 45 is a computer screen shot view of a user interface preview screen according to the present invention.

Turning to FIGS. 45 and 49, in the next step 652, after a learning module is selected on the module selection page 604, the module preview screen page 614 that corresponds to the selected a learning module is displayed. The module learning objectives 605 and required instruments 606 are included on the screen and displayed to the user. A preview video 607 of the selected module is also embedded into the screen page. Information for each part of the module preview screen is populated by querying the SQL database for the selected module's description, objectives, required devices and preview video. For example, if a laparoscopic cholecystectomy module is selected, the video 607 at step 652 will explain what a laparoscopic cholecystectomy is and its advantages over other non-laparoscopic procedures. The video will provide a brief overview of major anatomical regions involved, and key techniques and skills required to complete the procedure. The required instruments 606 are displayed, for this example, to be four trocars, one grasper, two dissectors, one scissor, and may further include one clip applier and one optional retrieval bag. Step-by-step instructions are provided via the imbedded video 607. Examples of other learning modules include laparoscopic right colectomy, and total laparoscopic hysterectomy.

Each practice module is configured to familiarize the practitioner with the steps of the procedure and the relevant anatomy. It also permits the user to practice the surgical technique and strive for proficiency in completing the procedure safely and efficiently. To aid in tracking performance, metrics measuring operative efficiency are also computed and displayed at the end of the procedure.

Turning to FIGS. 46 and 49, in the next step 654, a demographics questionnaire is presented to the user. Each question with their corresponding set of answers is populated by querying the SQL database 620 for the selected module's survey questions and answers 608. The selected answer is then stored in a SQL database 630. Questions include user's title, level of experience, number of procedures performed, number of procedures assisted, and user's dominant hand.

Figure 47:
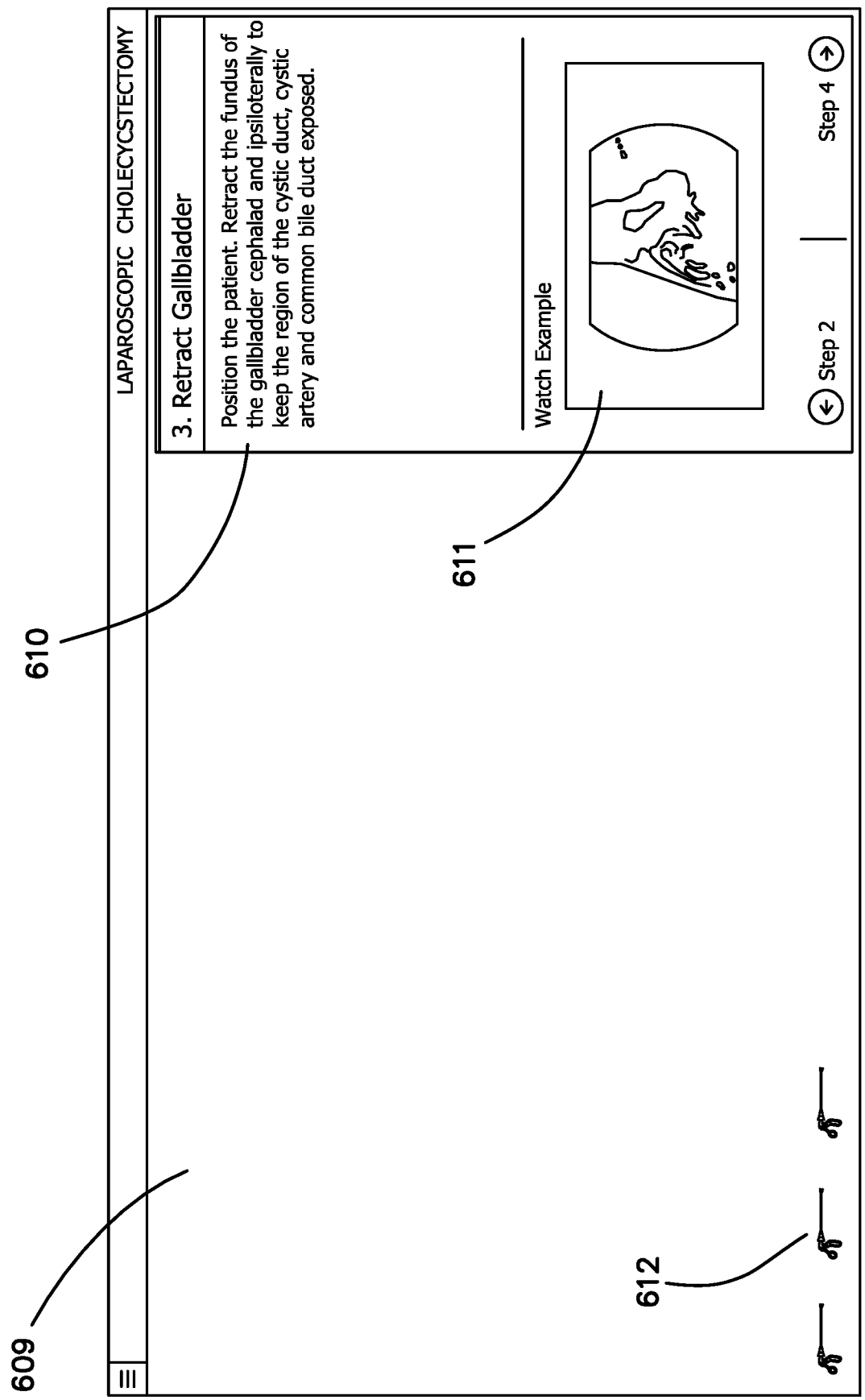
FIG. 47 is a computer screen shot view of a user interface learning module screen according to the present invention.

With reference to FIGS. 47 and 49, in the next step 656, the learning module screen for the selected module is presented to the user. With particular reference to FIG. 47, the left side 609 of the graphical user interface is an embedded video of a live laparoscope image feed of the cavity of the trainer displayed to the user. On the right side each surgical step 610 of the laparoscopic procedure is sequentially displayed to user accompanied by a brief instruction of the surgical step and an embedded instructional video 611 showing an example of a successful performance of the step. Laparoscopic instruments being used during the learning module are shown on the bottom 612 of the live laparoscope image feed. Data from laparoscopic instruments is streamed through serial ports and stored in the SQL database 630. For example, if a laparoscopic cholecystectomy is selected as the learning module, the surgical steps 610 that are displayed to the user include: (1) First entry: place your first port and survey the abdominal cavity for abnormalities and relevant anatomy; (2) Place ancillary ports: under direct visualization, place your ancillary ports; (3) Retract gallbladder: position the patient with your grasper grasp the fundus of the gallbladder and retract cephalad and ipsilaterally to keep the region of the cystic duct, cystic artery and common bile duct exposed; (4) Dissect the Triangle of Calot: with your grasper, grasp the infundibulum of the gallbladder and retract inferio-laterally to expose Calot's Triangle and use your dissector to bluntly dissect the triangle of Calot until the Critical View of Safety is achieved and only two structures are visible entering the gallbladder; (5) Ligate and divide cystic duct and artery: ligate the cystic duct and artery by using your clip applier to place three clips on each structure, two proximally and one distally, and use your scissors to divide the cystic duct and cystic artery; (6) Dissect gallbladder from liver bed: retract the gallbladder in the superio-lateral direction using your grasper holding the infundibulum and scissors with or without electrosurgery; alternatively, a dedicated energy device may be used to carefully dissect the gallbladder entirely from the liver bed; (7) Specimen Extraction: Extract the specimen through one of your ports; and (8) Port Removal: survey the abdominal cavity one last time before removing your ports.

Figure 48:
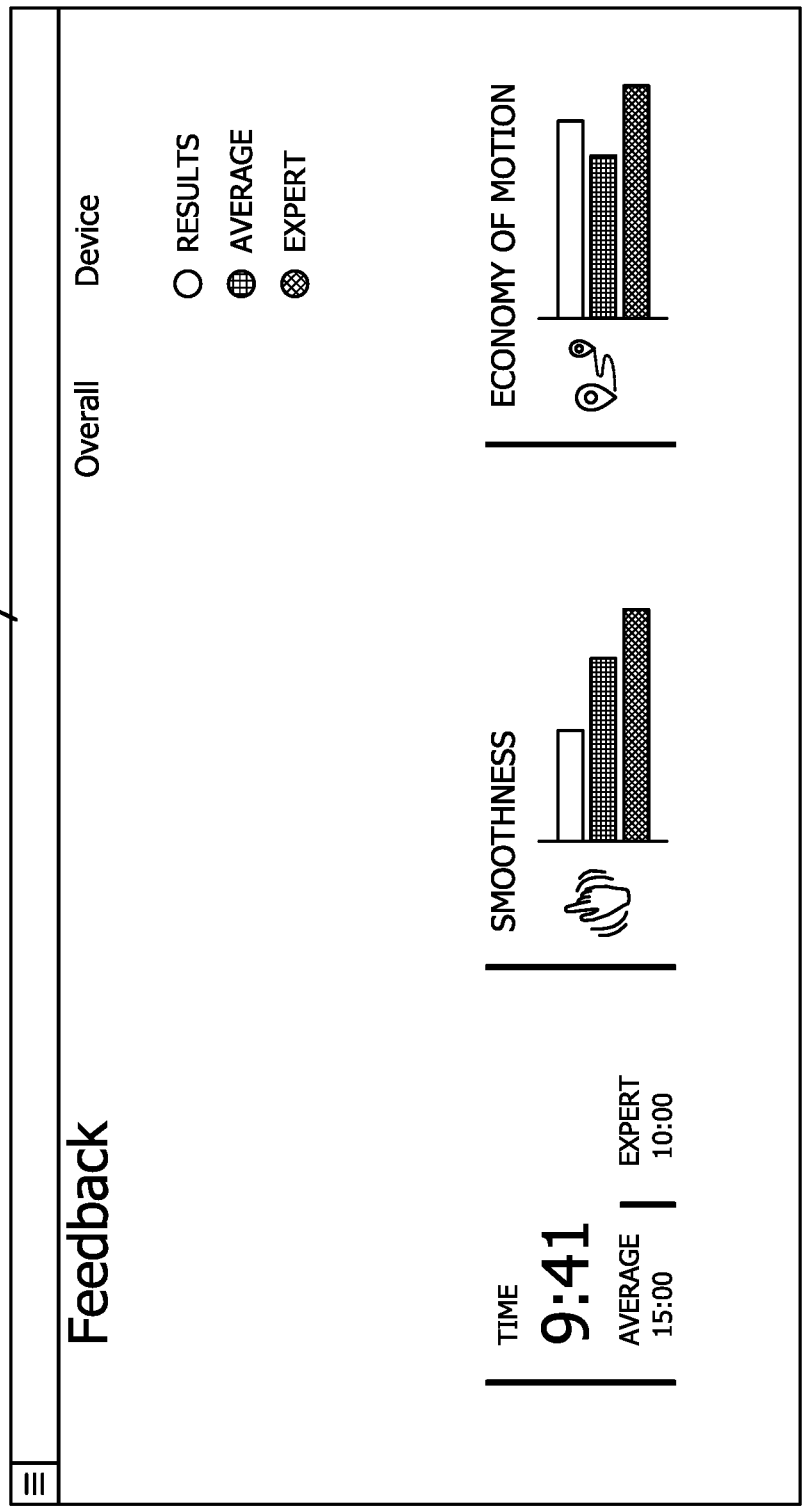
FIG. 48 is a computer screen shot view of a user interface user feedback screen according to the present invention.

Turning now to FIGS. 48 and 49, in the next step 658 data that is collected and stored during the learning module from the connected laparoscopic instruments is queried from the database 630, and run through analytics algorithms to output resulting metrics data. Resulting metrics data from the analytics is then displayed to the user on the screen 613 using D3 visualizations in a web browser embedded in the feedback screen 613. As shown in FIG. 48, the user's time is displayed together with the average time and an expert's time to complete the module providing comparative performance analysis to the user. Smoothness of motion and economy of motion are also displayed and compared with the average and expert results. Based on the information collected in the survey at step 654, module results are categorized accordingly as expert or non-expert data. The results are averaged for expert and non-experts and presented as shown.

It is understood that various modifications may be made to the embodiments disclosed herein. Therefore, the above description should not be construed as limiting, but merely as exemplifications of preferred embodiments. Those skilled in the art will envision other modifications within the scope and spirit of the present disclosure.

We claim:

1. An instrument for surgical training comprising:
   a shaft assembly removably connected to a handle assembly; the handle assembly including a movement arm having a distal end and a proximal end operably connected to a handle; the shaft assembly including a tool element at a distal end of the shaft assembly, a lumen, and a rod having a proximal end and a distal end connected to the tool element; the rod being disposed inside the lumen; the proximal end of the shaft assembly being removably connected to the handle assembly such that the proximal end of the rod is connected to the distal end of the movement arm; wherein actuation at the handle moves the movement arm and rod to operate the tool element;
   at least one sensor attached directly to the handle assembly and configured to acquire and transmit at least one relational data of the instrument with respect to a training environment during a training procedure, wherein the at least one sensor is configured to track user movements of the instrument during the training procedure; and
   a computer system connected to the at least one sensor configured to receive, store and process the at least one relational data and to output at least one feedback to a user after the training procedure based on processing of the at least one relational data, wherein the at least one relational data includes calculating a path length of a tip of the instrument divided by an average path length of other users for the training procedure, the path length being calculated by the computer system via:
  taking dot products of adjacent orientation vectors in a data sequence thereby providing a plurality of angles of changes in orientation,
  multiplying each angle of the plurality of angles of changes in the dot product data sequence by a length of the tool element thereby providing an arc length that the tool element traveled, and
  calculating a total path length based on a sum series of the arc lengths, the sum series of the arc lengths corresponding to how far the tool element traveled.

2. The instrument of claim 1 wherein the at least one sensor includes a strain gauge located on the movement arm.

3. The instrument of claim 2 wherein the strain gauge is configured to measure force applied by the user at the tool element in relation to the training environment.

4. The instrument of claim 1 wherein the at least one sensor includes an accelerometer, gyroscope, and magnetometer.

5. The instrument of claim 1 wherein the proximal end of the rod includes a ball end configured to be connected with a spherical slot located at the distal end of the movement arm.

6. The instrument of claim 1 wherein the tool element is configured as a scissor, grasper, or dissector.

7. The instrument of claim 1 wherein the training environment includes a laparoscopic trainer defining an interior and at least one simulated tissue disposed in the interior of the laparoscopic trainer.

8. The instrument of claim 1 wherein the at least one feedback is also based on the processing of additional relational data acquired from the at least one sensor, the processing of the additional relational data being selected from the group consisting of:
  a time to complete the training procedure by the user;
  a time to complete the training procedure by an expert;
  an average time to complete the training;
  an economy of motion of the user for the training procedure;
  an economy of motion of an expert for the training procedure;
  an average economy of motion of all users for the training procedure;
  a smoothness of motion of the user for the training procedure;
  a smoothness of motion of an expert for the training procedure; and
  an average smoothness of motion of all users for the training procedure.

9. The instrument of claim 1 wherein the at least one feedback is a time to complete the training procedure by the user excluding idle time of the instrument.

10. The instrument of claim 1 wherein the training procedure is selected by the user from a plurality of pre-defined training procedures displayed on the computer.

11. The instrument of claim 1, wherein the at least one sensor is calibrated for an output of force at a tip of the instrument, and wherein the output of force corresponds to a pre-determined value associated with harming or damaging tissue during a particular procedure.

12. The instrument of claim 7, wherein the training environment further comprises an internal camera that records actions performed by the user and an external video monitor that displays the actions captured by the internal camera.

13. The instrument of claim 1, wherein the user is provided the at least one feedback as a graphical result.

14. The instrument of claim 1, wherein the computer system further performs pre-processing on the at least one relational data provided by the at least one sensor, wherein the pre-processing performed by the computer system comprises identifying and calibrating for errors specific with the at least one sensor.

15. The instrument of claim 14, wherein the calibration for errors specific with the at least one sensor includes generating a calibration constant or a set of coefficients that are used to compensate for errors for relational data obtained from that specific sensor.

16. The instrument of claim 9, wherein the idle time of the instrument is identified via the computer system by identifying a set aside state for the instrument, and wherein the computer system identifies the set aside state by calculating a derivative over time of data obtained from the at least one sensor, and detecting when the derivative of the data remains zero for more than a pre-determined period of time, the data being accelerometer data.

17. The instrument of claim 16, wherein the identifying of the set aside state for the instrument further includes a buffer period to correspond to when the user is picking up and putting down the instrument.

18. The instrument of claim 4, wherein relational data from the accelerometer, the gyroscope, and the magnetometer allows the computer system to process an orientation of the instrument during the training procedure.

19. The instrument of claim 8, wherein the smoothness of motion is calculated by the computer system via:
  determining a position of the tool element,
  projecting a pseudo-2D position associated with a lateral sweeping motion of the instrument, wherein the pseudo-2D position corresponds to a travel path of the tool element,
  calculating a curvature value where the curvature value $$(k) = \frac{|x'y'' - y'x''|}{(x'^2 - y'^2)^{3/2}},$$

and
  calculating a smoothness value quantifying the smoothness of motion where $$\text{smoothness} = \frac{stdev(diff(k))}{|mean(diff(k))|}.$$

20. The instrument of claim 1, wherein the at least one relational data includes a smoothness of motion during the training procedure, and wherein the smoothness of motion is calculated by the computer system via:
  determining a position of the tool element,
  projecting a pseudo-2D position associated with a lateral sweeping motion of the instrument, wherein the pseudo-2D position corresponds to a travel path of the tool element,
  calculating a curvature value, and
  calculating a smoothness value quantifying the smoothness of motion.

21. An instrument for surgical training comprising:
  a shaft assembly removably connected to a handle at a proximal end and having a tool element at a distal end, wherein actuation at the handle operates the tool element;

at least one sensor attached directly to the handle and configured to acquire and transmit relational data of the instrument with respect to a training environment during a training procedure; and a computer system connected to the at least one sensor configured to receive, store, and process the relational data from the at least one sensor, wherein computer system calculates a path length of a tip of the instrument and further divides with an average path length of other users performing the same training procedure, wherein computer system calculates the path length from the relational data by:

taking dot products of adjacent orientation vectors in a data sequence thereby providing a plurality of angles of changes in orientation, multiplying each angle of the plurality of angles of changes in the dot product data sequence by a length of the tool element thereby providing an arc length that the tool element traveled, and calculating a total path length based on a sum series of the arc lengths, the sum series of the arc lengths corresponding to how much the tool element traveled.

22. An instrument for surgical training comprising:

a shaft assembly removably connected to a handle at a proximal end and having a tool element at a distal end, wherein actuation at the handle operates the tool element;

at least one sensor attached directly to the handle and configured to acquire and transmit relational data of the instrument with respect to a training environment during a training procedure; and a computer system connected to the at least one sensor configured to receive, store, and process the relational data from the at least one sensor, wherein computer system calculates smoothness of motion of the instrument during the training procedure, and wherein the computer system calculates smoothness by:

determining a position of the tool element, projecting a pseudo-2D position associated with a lateral sweeping motion of the instrument, wherein the pseudo-2D position corresponds to a travel path of the tool element, calculating a curvature value, and calculating a smoothness value quantifying the smoothness of motion.

23. The instrument of claim 22, wherein the curvature value $$(k) = \frac{|x'y'' - y'x''|}{(x'^2 - y'^2)^{3/2}}.$$

24. The instrument of claim 23, wherein the $$\text{smoothness} = \frac{stdev(\textit{diff}(k))}{|mean(\textit{diff}(k))|}.$$

25. The instrument of claim 24, wherein the handle of the shaft assembly includes a movement arm having a distal end and a proximal end operably connected to the handle, wherein the shaft assembly also includes a lumen and a rod having a proximal end and a distal end connected to the tool element, wherein the rod is disposed inside the lumen, wherein the proximal end of the shaft assembly is removably connected to the handle such that the proximal end of the rod is connected to the distal end of the movement arm, and wherein the actuation at the handle moves the movement arm and the rod to operate the tool element.

26. The instrument of claim 25, wherein the computer system further processes additional relational data acquired from the at least one sensor, the processing of the additional relational data being selected from the group consisting of:

a time to complete the training procedure by the user;
a time to complete the training procedure by an expert;
an average time to complete the training;
an economy of motion of the user for the training procedure;
an economy of motion of an expert for the training procedure;
an average economy of motion of all users for the training procedure;
a path length of the instrument tip of an expert divided by a path length of the user for the training procedure; and
a path length of the instrument tip of one or more expert users divided by an average path length of all users for the training procedure.

27. The instrument of claim 22, wherein the handle of the shaft assembly includes a movement arm having a distal end and a proximal end operably connected to the handle, wherein the shaft assembly also includes a lumen and a rod having a proximal end and a distal end connected to the tool element, wherein the rod is disposed inside the lumen, wherein the proximal end of the shaft assembly is removably connected to the handle such that the proximal end of the rod is connected to the distal end of the movement arm, and wherein the actuation at the handle moves the movement arm and the rod to operate the tool element.

* * * * *